US008470313B2

(12) United States Patent
Guo et al.

(10) Patent No.: US 8,470,313 B2
(45) Date of Patent: *Jun. 25, 2013

(54) RAS MUTATION AND COMPOSITIONS AND METHODS RELATED THERETO

(75) Inventors: Zhimin Guo, Louisville, CO (US); Yingnian Lu, Denver, CO (US); Donald Bellgrau, Highlands Ranch, CO (US); Alex Franzusoff, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 385 days.

This patent is subject to a terminal disclaimer.

(21) Appl. No.: 12/775,267

(22) Filed: May 6, 2010

(65) Prior Publication Data

US 2010/0215678 A1    Aug. 26, 2010

Related U.S. Application Data

(63) Continuation of application No. 11/684,290, filed on Mar. 9, 2007, now Pat. No. 7,745,128.

(60) Provisional application No. 60/786,568, filed on Mar. 27, 2006.

(51) Int. Cl.
*A61K 39/00* (2006.01)
*C12N 1/16* (2006.01)

(52) U.S. Cl.
USPC ............... 424/93.51; 424/185.1; 424/277.1; 424/278.1; 435/254.2

(58) Field of Classification Search
None
See application file for complete search history.

(56) References Cited

U.S. PATENT DOCUMENTS

| | | | |
|---|---|---|---|
| 4,725,550 A | 2/1988 | Perucho et al. | |
| 4,775,622 A | 10/1988 | Hitzeman et al. | |
| 4,871,838 A | 10/1989 | Bos et al. | |
| 5,830,463 A * | 11/1998 | Duke et al. | 424/93.51 |
| 5,847,095 A | 12/1998 | Bos et al. | |
| 5,858,378 A | 1/1999 | Bostwick | |
| 5,919,651 A | 7/1999 | Hitzeman et al. | |
| 5,945,306 A | 8/1999 | Bandman et al. | |
| 5,961,978 A | 10/1999 | Gaudernack et al. | |
| 6,090,546 A | 7/2000 | Breivik et al. | |
| 6,103,477 A | 8/2000 | Hillman et al. | |
| 7,465,454 B2 | 12/2008 | Franzusoff et al. | |
| 7,563,447 B2 | 7/2009 | Franzusoff et al. | |
| 2002/0044948 A1 | 4/2002 | Khleif et al. | |
| 2003/0035810 A1 | 2/2003 | Caplan | |
| 2007/0224208 A1 | 9/2007 | Guo et al. | |
| 2009/0098154 A1 | 4/2009 | Franzusoff et al. | |
| 2009/0142366 A1 | 6/2009 | Franzusoff et al. | |
| 2009/0142367 A1 | 6/2009 | Franzusoff et al. | |
| 2010/0034840 A1 | 2/2010 | Apelian et al. | |
| 2010/0111912 A1 | 5/2010 | Apelian et al. | |

FOREIGN PATENT DOCUMENTS

| | | |
|---|---|---|
| FR | 2486400 | 1/1982 |
| WO | WO 99/68677 | * 11/1999 |
| WO | WO 00/66153 | 11/2000 |
| WO | WO 02/39951 | 5/2002 |
| WO | WO 2007/008780 | 1/2007 |
| WO | WO 2008/097863 | 8/2008 |

OTHER PUBLICATIONS

Guilliam et al (Molecular and Cellular Biology, 1994, vol. 14, pp. 1113-1121).*
Mosteller et al (Molecular and Cellular Biology, 1994, vol. 14, pp. 1104-1112).*
English Translation of Official Action for Chinese Patent Application No. 200780018381.4, issued May 10, 2011 6 pages.
Fenton et al. "Induction of T-Cell Immunity Against Ras Oncoproteins by Soluble Protein or Ras-Expressing *Escherichia coli*," Journal of the National Cancer Institute, Dec. 20, 1995, vol. 87, No. 24, pp. 1853-1861.
Lemoine et al. "High frequency of ras oncogene activation in all stages of human thyroid tumorigenesis." Oncogene, Feb. 1989, vol. 4, No. 2, pp. 159-164 (Abstract only) 1 page.
Official Action for Australia Patent Application No. 2007249639, dated Sep. 8, 2011 2 pages.
English translation of Official Action for China Patent Application No, 200780018381.4, dated Nov. 14, 2011 4 pages.
Official Action for European Patent Application No. 07797163,8, dated Jan. 16, 2012 5 pages.
Abrams et al., "Mutant ras Epitopes as Targets for Cancer Vaccines", Feb. 1996, vol. 23, abstract only.
Akagi et al., "Characterization of a Novel Oncogenic K-ras Mutation in Colon Cancer", Biochemical and Biophysical Research Communications, 2007, vol. 352, pp. 728-732 D.
Bos, "ras Oncogenes in Human Cancer: A Review", Cancer Research, Sep. 1, 1989, vol. 49, pp. 4682-4689.
Chen et al., "Comparison of the Average Structures, from Molecular Dynamics, of Complexes of GTPase Activating Protein (GAP) with Oncogenic and Wild-Type ras-p21: Identification of Potential Effector Domains", Journal of Protein D Chemistry, Jul. 2002, vol. 21, pp. 349-359.
Downward, "Targeting Ras Signalling Pathways in Cancer Therapy", Nature Reviews, Jan. 2003, vol. 3, pp. 11-22.
Franzusoff et al., "Yeasts encoding tumour antigens in cancer immunotherapy" Expert Opin. Bio. Ther. (2005) 5(4), pp. 565-575.
Friday, "K-ras as a Target for Cancer Therapy", Biochemica et Biophysica Acta, 2005, vol. 1756, pp. 127-144.
Huncharek et al., "K-ras as a Prognostic Marker in Non-small Cell Lung Cancer: a Combined Analysis of 881 Cases", Carcinogenesis, 1999, vol. 20, pp. 1507-151.
Lu et al., "Mutation-Selective Tumor Remission with Ras-Targeted, Whole Yeast-Based Immunotherapy", Cancer Research, Aug. 1, 2004, vol. 64, pp. 5084-5088.

(Continued)

*Primary Examiner* — Karen Canella
(74) *Attorney, Agent, or Firm* — Angela Dallas Sebor; Sheridan Ross P.C.

(57) ABSTRACT

Disclosed are newly discovered Ras mutations and combinations of mutations, proteins and peptides and fusion proteins containing these mutations, nucleic acid molecules encoding such proteins, peptides, and fusion proteins, and a variety of tools and diagnostic, therapeutic, and screening methods associated with the use of such mutations.

20 Claims, 5 Drawing Sheets

OTHER PUBLICATIONS

Midgley and Kerr, "Ras as a Target in Cancer Therapy", Critical Reviews in Oncology/Hematology, 2002, vol. 44, pp. 109-112.

Nielsen et al., "Sensitivity of Wild Type and Mutant ras Alleles to Ras Specific Exchange Factors: Identification of Factor Specific Requirements", Oncogene, 2001, vol. 20, pp. 2091-2100.

Ricci et al., "A Case of Chronic Myelomonocytic Leukemia Progressing from Dysplastic to Proliferative Phenotype after Acquisition of a RAS Point Mutation," Blood, vol. 106, No. 11, Nov. 16, 2005, 320B.

Schleger et al., "The Role of Wild-Type and Mutated N-ras in the Malignant Transformation of Liver Cells", Molecular Carcinogenesis, 2000, vol. 28, pp. 31-41.

Sinai et al., "Enhancement of Resistance to Infectious Diseases by Oral Administration of Brewer's Yeast," Infection and Immunity, vol. 9 No. 5, pp. 781-787 (May 1974).

Stubbs et al. "Whole recombinant yeast vaccine activates dendric cells and elicits protective cell-mediated immunity", Nature Medicine May 2001, vol. 7, pp. 1-5.

Wittinghofer et al., "Three-Dimensional Structure of p21 in the Active Conformation and Analysis of an Oncogenic Mutant", Environmental Health Perspectives, 1991, vol. 93, pp. 11-15.

Wu, Database DISSABS, on STN, AN 2001:14790, "Structural Analysis of Oncogenic H-ras Mutants G12A and G13A", Masters Abstract International, 1999, vol. 38, p. 954, abstract.

Communication from the Examining Division for European Patent Application No. 07797163.8, mailed Jan. 28, 2010.

International Preliminary Report on Patentability, PCT Application No. PCT/US07/63711, filed Mar. 9, 2007.

International Search Report and The Written Opinion of the International Search Authority, PCT Application No. PCTI US07/63711, filed Mar. 9, 2007.

Supplementary European search report and Opinion for European Patent Application No. 07797163.8, mailed Oct. 19, 2009.

Notice of Allowance for U.S. Appl. No. 11/684,290, mailed Apr. 15, 2010.

Official Action for U.S. Appl. No. 11/684,290, mailed Sep. 21, 2009.

Esteller et al. "The Clinicopathological Significance of K-RAS Point Mutation and Gene Amplification in Endometrial Cancer," European Journal of Cancer, 1997, vol. 33, No. 10, pp. 1572-1577.

Freitas et al. "Bracken fern-induced malignant tumors in rats: absence of mutations in p53, H-ras and K-ras and no microsatellite instability," Mutation Research, 2002, 499, pp. 189-196.

Han "*Schistosoma japonicum* SJCHGC09408 protein mRNA, complete cds," GenBank:AY813082, Sep. 23, 2005, retrieved from the Internet (www.ncbi.nlm.nih.gov/nuccore/AY813082.1?report=girevhist).

Kreimer-Erlacher et al. "High Mutation Frequency at Ha-ras Exons 1-4 in Squamous Cell Carcinomas from PUVA-treated Psoriasis Patients," Photochemistry and Photobiology, 2001, vol. 74, No. 2, pp. 323-330.

Liu et al. "New Perspectives on Host-Parasite Interplay by Comparative Transcriptomic and Proteomic Analyses of *Schistosoma japonicum*," PLo5 Pathogens, Apr. 2006, vol. 2, No. 4, pp. 268-281.

Manam et al. "MultiPlex Polymerase Chain Reaction Amplification and Direct Sequencing of Homologous Sequences: Point Mutation Analysis of the ras Genes," Analytical Biochemistry, 1991, vol. 199, pp. 106-111.

Tao et al. "Uptake, Intracellular Distribution, and Stability of Oligodeoxynucleotide Phosphorothioate by *Schistosoma mansoni*," Antisense Research and Development, 1995, vol. 5, pp. 123-129.

Notice of Acceptance for Australia Patent Application No. 2007249639, dated May 17, 2012 3 pages.

English Translation of Official Action for China Patent Application No. 200780018381.4, dated Oct. 24, 2012 4 pages.

English Translation of Official Action for Japan Patent Application No. 2009-503126, mailed May 29, 2012 9 pages.

Official Action with English translation for Taiwan Patent Application No. 096108338, dated Jul. 13, 2012 13 pages.

Official Action for European Patent Application No. 07797163.8, dated Oct. 30, 2012 3 pages.

* cited by examiner

Negative
BALB/3T3 cells - untransfected

Positive
BALB/3T3 cells - G12V + E76G Ras transfected

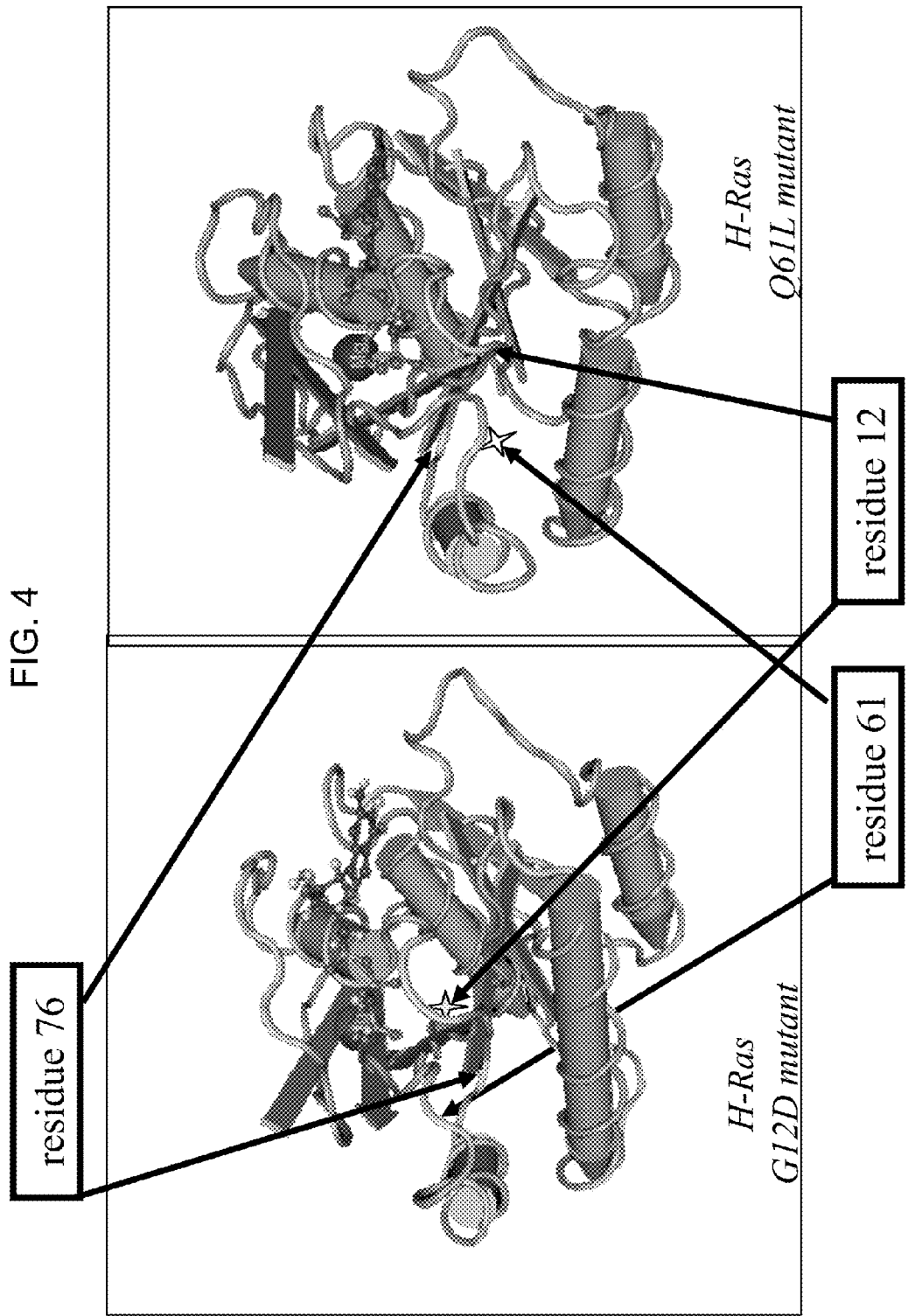

SEQUENCE LISTING

<160> NUMBER OF SEQ ID NOS: 46

<210> SEQ ID NO 1
<211> LENGTH: 6
<212> TYPE: PRT
<213> ORGANISM: artificial
<220> FEATURE:
<223> OTHER INFORMATION: synthetic

<400> SEQUENCE: 1

Met Ala Asp Glu Ala Pro
1               5

<210> SEQ ID NO 2
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 2 atg act gaa tat aaa ctt gtg gta gtt gga gct ggt ggc gta ggc aag      48
Met Thr Glu Tyr Lys Leu Val Val Val Gly Ala Gly Gly Val Gly Lys
1               5                   10                  15 agt gcc ttg acg ata cag cta att cag aat cat ttt gtg gac gaa tat      96
Ser Ala Leu Thr Ile Gln Leu Ile Gln Asn His Phe Val Asp Glu Tyr
            20                  25                  30 gat cca aca ata gag gat tcc tac agg aag caa gta gta att gat gga     144
Asp Pro Thr Ile Glu Asp Ser Tyr Arg Lys Gln Val Val Ile Asp Gly
        35                  40                  45 gaa acc tgt ctc ttg gat att ctc gac aca gca ggt caa gag gag tac     192
Glu Thr Cys Leu Leu Asp Ile Leu Asp Thr Ala Gly Gln Glu Glu Tyr
    50                  55                  60 agt gca atg agg gac cag tac atg agg act ggg gag ggc ttt ctt tgt     240
Ser Ala Met Arg Asp Gln Tyr Met Arg Thr Gly Glu Gly Phe Leu Cys
65                  70                  75                  80 gta ttt gcc ata aat aat act aaa tca ttt gaa gat att cac cat tat     288
Val Phe Ala Ile Asn Asn Thr Lys Ser Phe Glu Asp Ile His His Tyr
                85                  90                  95 aga gaa caa att aaa aga gtt aag gac tct gaa gat gta cct atg gtc     336
Arg Glu Gln Ile Lys Arg Val Lys Asp Ser Glu Asp Val Pro Met Val
            100                 105                 110 cta gta gga aat aaa tgt gat ttg cct tct aga aca gta gac aca aaa     384
Leu Val Gly Asn Lys Cys Asp Leu Pro Ser Arg Thr Val Asp Thr Lys
        115                 120                 125 cag gct cag gac tta gca aga agt tat gga att cct ttt att gaa aca     432
Gln Ala Gln Asp Leu Ala Arg Ser Tyr Gly Ile Pro Phe Ile Glu Thr
    130                 135                 140 tca gca aag aca aga cag aga gtg gag gat gct ttt tat aca ttg gtg     480
Ser Ala Lys Thr Arg Gln Arg Val Glu Asp Ala Phe Tyr Thr Leu Val
145                 150                 155                 160 agg gag atc cga caa tac aga ttg aaa aaa atc agc aaa gaa gaa aag     528
Arg Glu Ile Arg Gln Tyr Arg Leu Lys Lys Ile Ser Lys Glu Glu Lys
                165                 170                 175 act cct ggc tgt gtg aaa att aaa aaa tgc att ata atg taa              570
Thr Pro Gly Cys Val Lys Ile Lys Lys Cys Ile Ile Met
            180                 185

<210> SEQ ID NO 3
<211> LENGTH: 189
<212> TYPE: PRT

-continued

<213> ORGANISM: Homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 4
<211> LENGTH: 567
<212> TYPE: DNA
<213> ORGANISM: Mus musculus
<220> FEATURE:
<221> NAME/KEY: CDS
<222> LOCATION: (1)..(567)

<400> SEQUENCE: 4 atg act gag tat aaa ctt gtg gtg gtt gga gct ggt ggc gta ggc aag    48
Met Thr Glu Tyr Lys Leu Val Val Val Gly Ala Gly Gly Val Gly Lys
1               5                   10                  15 agc gcc ttg acg ata cag cta att cag aat cac ttt gtg gat gag tac    96
Ser Ala Leu Thr Ile Gln Leu Ile Gln Asn His Phe Val Asp Glu Tyr
            20                  25                  30 gac cct acg ata gag gac tcc tac agg aaa caa gta gta att gat gga   144
Asp Pro Thr Ile Glu Asp Ser Tyr Arg Lys Gln Val Val Ile Asp Gly
        35                  40                  45 gaa acc tgt ctc ttg gat att ctc gac aca gca ggt caa gag gag tac   192
Glu Thr Cys Leu Leu Asp Ile Leu Asp Thr Ala Gly Gln Glu Glu Tyr
    50                  55                  60 agt gca atg agg gac cag tac atg aga act ggg gag ggc ttt ctt tgt   240
Ser Ala Met Arg Asp Gln Tyr Met Arg Thr Gly Glu Gly Phe Leu Cys
65                  70                  75                  80 gta ttt gcc ata aat aat act aaa tca ttt gaa gat att cac cat tat   288
Val Phe Ala Ile Asn Asn Thr Lys Ser Phe Glu Asp Ile His His Tyr
                85                  90                  95 aga gaa caa att aaa aga gta aag gac tct gaa gat gtg cct atg gtc   336
Arg Glu Gln Ile Lys Arg Val Lys Asp Ser Glu Asp Val Pro Met Val
            100                 105                 110 ctg gta ggg aat aag tgt gat ttg cct tct aga aca gta gac acg aaa   384
Leu Val Gly Asn Lys Cys Asp Leu Pro Ser Arg Thr Val Asp Thr Lys

```
Leu Val Gly Asn Lys Cys Asp Leu Pro Ser Arg Thr Val Asp Thr Lys
        115                 120                 125 cag gct cag gag tta gca agg agt tac ggg att ccg ttc att gag acc      432
Gln Ala Gln Glu Leu Ala Arg Ser Tyr Gly Ile Pro Phe Ile Glu Thr
130                 135                 140 tca gca aag aca aga cag ggt gtt gac gat gcc ttc tat aca tta gtc      480
Ser Ala Lys Thr Arg Gln Gly Val Asp Asp Ala Phe Tyr Thr Leu Val
145                 150                 155                 160 cga gaa att cga aaa cat aaa gaa aag atg agc aaa gat ggg aag aag      528
Arg Glu Ile Arg Lys His Lys Glu Lys Met Ser Lys Asp Gly Lys Lys
                165                 170                 175 aag aag aag aag tca agg aca agg tgt aca gtt atg tga                  567
Lys Lys Lys Lys Ser Arg Thr Arg Cys Thr Val Met
            180                 185

<210> SEQ ID NO 5
<211> LENGTH: 188
<212> TYPE: PRT
<213> ORGANISM: Mus musculus

<400> SEQUENCE: 5

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185

<210> SEQ ID NO 6
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 6 atg acg gaa tat aag ctg gtg gtg gtg ggc gcc ggc ggt gtg ggc aag      48
Met Thr Glu Tyr Lys Leu Val Val Val Gly Ala Gly Gly Val Gly Lys
1               5                   10                  15 agt gcg ctg acc atc cag ctg atc cag aac cat ttt gtg gac gaa tac      96
Ser Ala Leu Thr Ile Gln Leu Ile Gln Asn His Phe Val Asp Glu Tyr
```

```
                    20                  25                  30
gac ccc act ata gag gat tcc tac cgg aag cag gtg gtc att gat ggg      144
Asp Pro Thr Ile Glu Asp Ser Tyr Arg Lys Gln Val Val Ile Asp Gly
         35                  40                  45 gag acg tgc ctg ttg gac atc ctg gat acc gcc ggc cag gag gag tac      192
Glu Thr Cys Leu Leu Asp Ile Leu Asp Thr Ala Gly Gln Glu Glu Tyr
 50                  55                  60 agc gcc atg cgg gac cag tac atg cgc acc ggg gag ggc ttc ctg tgt      240
Ser Ala Met Arg Asp Gln Tyr Met Arg Thr Gly Glu Gly Phe Leu Cys
 65                  70                  75                  80 gtg ttt gcc atc aac aac acc aag tct ttt gag gac atc cac cag tac      288
Val Phe Ala Ile Asn Asn Thr Lys Ser Phe Glu Asp Ile His Gln Tyr
                 85                  90                  95 agg gag cag atc aaa cgg gtg aag gac tcg gat gac gtg ccc atg gtg      336
Arg Glu Gln Ile Lys Arg Val Lys Asp Ser Asp Asp Val Pro Met Val
            100                 105                 110 ctg gtg ggg aac aag tgt gac ctg gct gca cgc act gtg gaa tct cgg      384
Leu Val Gly Asn Lys Cys Asp Leu Ala Ala Arg Thr Val Glu Ser Arg
        115                 120                 125 cag gct cag gac ctc gcc cga agc tac ggc atc ccc tac atc gag acc      432
Gln Ala Gln Asp Leu Ala Arg Ser Tyr Gly Ile Pro Tyr Ile Glu Thr
130                 135                 140 tcg gcc aag acc cgg cag gga gtg gag gat gcc ttc tac acg ttg gtg      480
Ser Ala Lys Thr Arg Gln Gly Val Glu Asp Ala Phe Tyr Thr Leu Val
145                 150                 155                 160 cgt gag atc cgg cag cac aag ctg cgg aag ctg aac cct cct gat gag      528
Arg Glu Ile Arg Gln His Lys Leu Arg Lys Leu Asn Pro Pro Asp Glu
                165                 170                 175 agt ggc ccc ggc tgc atg agc tgc aag tgt gtg ctc tcc tga              570
Ser Gly Pro Gly Cys Met Ser Cys Lys Cys Val Leu Ser
            180                 185
```

<210> SEQ ID NO 7
<211> LENGTH: 189
<212> TYPE: PRT
<213> ORGANISM: Homo sapiens

<400> SEQUENCE: 7

```
Met Thr Glu Tyr Lys Leu Val Val Val Gly Ala Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
130                 135                 140

Ser Ala Lys Thr Arg Gln Gly Val Glu Asp Ala Phe Tyr Thr Leu Val
145                 150                 155                 160
```

```
Arg Glu Ile Arg Gln His Lys Leu Arg Lys Leu Asn Pro Pro Asp Glu
            165                 170                 175

Ser Gly Pro Gly Cys Met Ser Cys Lys Cys Val Leu Ser
            180                 185
```

<210> SEQ ID NO 8
<211> LENGTH: 570
<212> TYPE: DNA
<213> ORGANISM: Mus musculus
<220> FEATURE:
<221> NAME/KEY: CDS
<222> LOCATION: (1)..(570)

<400> SEQUENCE: 8

```
atg aca gaa tac aag ctt gtg gtg gtg ggc gct gga ggc gtg gga aag      48
Met Thr Glu Tyr Lys Leu Val Val Val Gly Ala Gly Gly Val Gly Lys
1               5                   10                  15 agt gcc ctg acc atc cag ctg atc cag aac cac ttt gtg gac gag tat      96
Ser Ala Leu Thr Ile Gln Leu Ile Gln Asn His Phe Val Asp Glu Tyr
            20                  25                  30 gat ccc act ata gag gac tcc tac cgg aaa cag gtg gtc att gat ggg     144
Asp Pro Thr Ile Glu Asp Ser Tyr Arg Lys Gln Val Val Ile Asp Gly
        35                  40                  45 gag aca tgt cta ctg gac tac tta gac aca gca ggt caa gaa gag tat     192
Glu Thr Cys Leu Leu Asp Tyr Leu Asp Thr Ala Gly Gln Glu Glu Tyr
    50                  55                  60 agt gcc atg cgg gac cag tac atg cgc aca ggg gag ggc ttc ctc tgt     240
Ser Ala Met Arg Asp Gln Tyr Met Arg Thr Gly Glu Gly Phe Leu Cys
65                  70                  75                  80 gta ttt gcc atc aac aac acc aag tcc ttc gag gac atc cat cag tac     288
Val Phe Ala Ile Asn Asn Thr Lys Ser Phe Glu Asp Ile His Gln Tyr
                85                  90                  95 agg gag cag atc aag cgg gtg aaa gat tca gat gat gtg cca atg gtg     336
Arg Glu Gln Ile Lys Arg Val Lys Asp Ser Asp Asp Val Pro Met Val
            100                 105                 110 ctg gtg ggc aac aag tgt gac ctg gct gct cgc act gtt gag tct cgg     384
Leu Val Gly Asn Lys Cys Asp Leu Ala Ala Arg Thr Val Glu Ser Arg
        115                 120                 125 cag gcc cag gac ctt gct cgc agc tat ggc atc ccc tac att gaa aca     432
Gln Ala Gln Asp Leu Ala Arg Ser Tyr Gly Ile Pro Tyr Ile Glu Thr
    130                 135                 140 tca gcc aag acc cgg cag ggc gtg gag gat gcc ttc tat aca cta gtc     480
Ser Ala Lys Thr Arg Gln Gly Val Glu Asp Ala Phe Tyr Thr Leu Val
145                 150                 155                 160 cgt gag att cgg cag cat aaa ttg cgg aaa ctg aac cca ccc gat gag     528
Arg Glu Ile Arg Gln His Lys Leu Arg Lys Leu Asn Pro Pro Asp Glu
                165                 170                 175 agt ggt cct ggc tgc atg agc tgc aaa tgt gtg ctg tcc tga             570
Ser Gly Pro Gly Cys Met Ser Cys Lys Cys Val Leu Ser
            180                 185
```

<210> SEQ ID NO 9
<211> LENGTH: 189
<212> TYPE: PRT
<213> ORGANISM: Mus musculus

<400> SEQUENCE: 9

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
```

```
                35                  40                  45
Glu Thr Cys Leu Leu Asp Tyr Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 10
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 10 atg act gag tac aaa ctg gtg gtg gtt gga gca ggt ggt gtt ggg aaa      48
Met Thr Glu Tyr Lys Leu Val Val Val Gly Ala Gly Gly Val Gly Lys
 1               5                  10                  15 agc gca ctg aca atc cag cta atc cag aac cac ttt gta gat gaa tat      96
Ser Ala Leu Thr Ile Gln Leu Ile Gln Asn His Phe Val Asp Glu Tyr
                20                  25                  30 gat ccc acc ata gag gat tct tac aga aaa caa gtg gtt ata gat ggt     144
Asp Pro Thr Ile Glu Asp Ser Tyr Arg Lys Gln Val Val Ile Asp Gly
            35                  40                  45 gaa acc tgt ttg ttg gac ata ctg gat aca gct gga caa gaa gag tac     192
Glu Thr Cys Leu Leu Asp Ile Leu Asp Thr Ala Gly Gln Glu Glu Tyr
 50                  55                  60 agt gcc atg aga gac caa tac atg agg aca ggc gaa ggc ttc ctc tgt     240
Ser Ala Met Arg Asp Gln Tyr Met Arg Thr Gly Glu Gly Phe Leu Cys
 65                  70                  75                  80 gta ttt gcc atc aat aat agc aag tca ttt gcg gat att aac ctc tac     288
Val Phe Ala Ile Asn Asn Ser Lys Ser Phe Ala Asp Ile Asn Leu Tyr
                 85                  90                  95 agg gag cag att aag cga gta aaa gac tcg gat gat gta cct atg gtg     336
Arg Glu Gln Ile Lys Arg Val Lys Asp Ser Asp Asp Val Pro Met Val
            100                 105                 110 cta gtg gga aac aag tgt gat ttg cca aca agg aca gtt gat aca aaa     384
Leu Val Gly Asn Lys Cys Asp Leu Pro Thr Arg Thr Val Asp Thr Lys
        115                 120                 125 caa gcc cac gaa ctg gcc aag agt tac ggg att cca ttc att gaa acc     432
Gln Ala His Glu Leu Ala Lys Ser Tyr Gly Ile Pro Phe Ile Glu Thr
        130                 135                 140 tca gcc aag acc aga cag ggt gtt gaa gat gct ttt tac aca ctg gta     480
Ser Ala Lys Thr Arg Gln Gly Val Glu Asp Ala Phe Tyr Thr Leu Val
145                 150                 155                 160
```

```
aga gaa ata cgc cag tac cga atg aaa aaa ctc aac agc agt gat gat    528
Arg Glu Ile Arg Gln Tyr Arg Met Lys Lys Leu Asn Ser Ser Asp Asp
                165                 170                 175 ggg act cag ggt tgt atg gga ttg cca tgt gtg gtg atg taa            570
Gly Thr Gln Gly Cys Met Gly Leu Pro Cys Val Val Met
        180                 185

<210> SEQ ID NO 11
<211> LENGTH: 189
<212> TYPE: PRT
<213> ORGANISM: Homo sapiens

<400> SEQUENCE: 11

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 12
<211> LENGTH: 582
<212> TYPE: DNA
<213> ORGANISM: Mus musculus
<220> FEATURE:
<221> NAME/KEY: CDS
<222> LOCATION: (1)..(582)

<400> SEQUENCE: 12 atg act gag tac aaa ctg gtg gtg gtt gga gca ggt ggt gtt ggg aaa    48
Met Thr Glu Tyr Lys Leu Val Val Val Gly Ala Gly Gly Val Gly Lys
1               5                   10                  15 agc gcc ctg acg atc cag cta atc cag aac cac ttt gtg gat gaa tat    96
Ser Ala Leu Thr Ile Gln Leu Ile Gln Asn His Phe Val Asp Glu Tyr
            20                  25                  30 gat ccc acc ata gag gat tct tac cga aag caa gtg gtg att gat ggt    144
Asp Pro Thr Ile Glu Asp Ser Tyr Arg Lys Gln Val Val Ile Asp Gly
        35                  40                  45 gag acc tgc ctg ctg gac ata ctg gac aca gct gga caa gag gag tac    192
Glu Thr Cys Leu Leu Asp Ile Leu Asp Thr Ala Gly Gln Glu Glu Tyr
    50                  55                  60 agt gcc atg aga gac cag tac atg agg aca ggc gaa ggg ttc ctc tgt    240
Ser Ala Met Arg Asp Gln Tyr Met Arg Thr Gly Glu Gly Phe Leu Cys
```

```
Ser Ala Met Arg Asp Gln Tyr Met Arg Thr Gly Glu Gly Phe Leu Cys
 65                  70                  75                  80 gta ttt gcc atc aat aat agc aaa tca ttt gca gat att aac ctc tac    288
Val Phe Ala Ile Asn Asn Ser Lys Ser Phe Ala Asp Ile Asn Leu Tyr
                 85                  90                  95 agg gag caa att aag cgt gtg aaa gat tct gat gat gtc ccc atg gtg    336
Arg Glu Gln Ile Lys Arg Val Lys Asp Ser Asp Asp Val Pro Met Val
                100                 105                 110 ctg gta ggc aac aag tgt gac ttg cca aca agg aca gtt gac aca aag    384
Leu Val Gly Asn Lys Cys Asp Leu Pro Thr Arg Thr Val Asp Thr Lys
                115                 120                 125 caa gcc cac gaa ctg gcc aag agt tac gga att cca ttc att gag acc    432
Gln Ala His Glu Leu Ala Lys Ser Tyr Gly Ile Pro Phe Ile Glu Thr
130                 135                 140 tca gcc aag acc cga cag ggt gtg gag gat gcc ttt tac aca ctg gta    480
Ser Ala Lys Thr Arg Gln Gly Val Glu Asp Ala Phe Tyr Thr Leu Val
145                 150                 155                 160 agg gag ata cgc cag tac cga ttg aaa aag ctc aac agc agt gac gat    528
Arg Glu Ile Arg Gln Tyr Arg Leu Lys Lys Leu Asn Ser Ser Asp Asp
                165                 170                 175 ggc act caa ggt tgt atg ggg tcg ccc tgt gtg ctg atg tgt aag aca    576
Gly Thr Gln Gly Cys Met Gly Ser Pro Cys Val Leu Met Cys Lys Thr
                180                 185                 190 ctt tga                                                            582
Leu

<210> SEQ ID NO 13
<211> LENGTH: 193
<212> TYPE: PRT
<213> ORGANISM: Mus musculus

<400> SEQUENCE: 13

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
                 35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Leu Lys Lys Leu Asn Ser Ser Asp Asp
                165                 170                 175

Gly Thr Gln Gly Cys Met Gly Ser Pro Cys Val Leu Met Cys Lys Thr
                180                 185                 190

Leu
```

<210> SEQ ID NO 14
<211> LENGTH: 275
<212> TYPE: PRT
<213> ORGANISM: Artificial
<220> FEATURE:
<223> OTHER INFORMATION: synthetic

<400> SEQUENCE: 14

```
Met Ala Asp Glu Ala Pro Thr Glu Tyr Lys Leu Val Val Gly Ala
1               5                   10                  15

Cys Gly Val Gly Lys Ser Ala Leu Thr Ile Gln Leu Ile Gln Asn His
                20                  25                  30

Phe Val Asp Glu Tyr Asp Pro Thr Ile Glu Asp Ser Tyr Arg Lys Gln
                35                  40                  45

Val Val Ile Asp Gly Glu Thr Cys Leu Leu Asp Ile Leu Asp Thr Ala
        50                  55                  60

Gly Arg Glu Glu Tyr Ser Ala Met Arg Asp Gln Tyr Met Arg Thr Gly
65                  70                  75                  80

Glu Gly Phe Leu Cys Val Phe Ala Ile Asn Asn Thr Glu Tyr Lys Leu
                85                  90                  95

Val Val Val Gly Ala Asp Gly Val Gly Lys Ser Ala Leu Thr Ile Gln
                100                 105                 110

Leu Ile Gln Asn His Phe Val Asp Glu Tyr Asp Pro Thr Ile Glu Asp
        115                 120                 125

Ser Tyr Arg Lys Gln Val Val Ile Asp Thr Glu Tyr Lys Leu Val Val
    130                 135                 140

Val Gly Ala Val Gly Val Gly Lys Ser Ala Leu Thr Ile Gln Leu Ile
145                 150                 155                 160

Gln Asn His Phe Val Asp Glu Tyr Asp Pro Thr Ile Glu Asp Ser Tyr
                165                 170                 175

Arg Lys Gln Val Val Ile Asp Thr Glu Tyr Lys Leu Val Val Val Gly
                180                 185                 190

Ala Arg Gly Val Gly Lys Ser Ala Leu Thr Ile Gln Leu Ile Gln Asn
        195                 200                 205

His Phe Val Asp Glu Tyr Asp Pro Thr Ile Glu Asp Ser Tyr Arg Lys
    210                 215                 220

Gln Val Val Ile Asp Gly Glu Thr Cys Leu Leu Asp Ile Leu Asp Thr
225                 230                 235                 240

Ala Gly Gln Glu Glu Tyr Ser Ala Met Arg Asp Gln Tyr Met Arg Thr
                245                 250                 255

Gly Gly Gly Phe Leu Cys Val Phe Ala Ile Asn Asn Thr Lys Ser Phe
                260                 265                 270

Glu Asp Ile
        275
```

<210> SEQ ID NO 15
<211> LENGTH: 98
<212> TYPE: PRT
<213> ORGANISM: artificial
<220> FEATURE:
<223> OTHER INFORMATION: synthetic

<400> SEQUENCE: 15

```
Met Ala Asp Glu Ala Pro Thr Glu Tyr Lys Leu Val Val Gly Ala
1               5                   10                  15

Arg Gly Val Gly Lys Ser Ala Leu Thr Ile Gln Leu Ile Gln Asn His
                20                  25                  30
```

```
Phe Val Asp Glu Tyr Asp Pro Thr Ile Glu Asp Ser Tyr Arg Lys Gln
         35                  40                  45

Val Val Ile Asp Gly Glu Thr Cys Leu Leu Asp Ile Leu Asp Thr Ala
 50                  55                  60

Gly Gln Glu Glu Tyr Ser Ala Met Arg Asp Gln Tyr Met Arg Thr Gly
 65                  70                  75                  80

Gly Gly Phe Leu Cys Val Phe Ala Ile Asn Asn Thr Lys Ser Phe Glu
                 85                  90                  95

Asp Ile

<210> SEQ ID NO 16
<211> LENGTH: 20
<212> TYPE: DNA
<213> ORGANISM: Artificial
<220> FEATURE:
<223> OTHER INFORMATION: synthetic

<400> SEQUENCE: 16
aggtgagttt gtattaaaag                                              20

<210> SEQ ID NO 17
<211> LENGTH: 18
<212> TYPE: DNA
<213> ORGANISM: Artificial
<220> FEATURE:
<223> OTHER INFORMATION: synthetic

<400> SEQUENCE: 17
tcatgaaaat ggtcagag                                                18

<210> SEQ ID NO 18
<211> LENGTH: 38
<212> TYPE: DNA
<213> ORGANISM: Artificial
<220> FEATURE:
<223> OTHER INFORMATION: synthetic

<400> SEQUENCE: 18
taatacgact cactataggg tgtgtgacat gttctaat                          38

<210> SEQ ID NO 19
<211> LENGTH: 40
<212> TYPE: DNA
<213> ORGANISM: Artificial
<220> FEATURE:
<223> OTHER INFORMATION: synthetic

<400> SEQUENCE: 19
atttaggtga cactatagaa gaatggtcct gcaccagtaa                        40

<210> SEQ ID NO 20
<211> LENGTH: 18
<212> TYPE: DNA
<213> ORGANISM: Artificial
<220> FEATURE:
<223> OTHER INFORMATION: synthetic

<400> SEQUENCE: 20
tgagttgtat ataacacc                                                18

<210> SEQ ID NO 21
<211> LENGTH: 18
<212> TYPE: DNA
<213> ORGANISM: Artificial
<220> FEATURE:
```

<223> OTHER INFORMATION: synthetic

<400> SEQUENCE: 21
ggcattagca aagactca                                                       18

<210> SEQ ID NO 22
<211> LENGTH: 38
<212> TYPE: DNA
<213> ORGANISM: Artificial
<220> FEATURE:
<223> OTHER INFORMATION: synthetic

<400> SEQUENCE: 22
taatacgact cactataggg tgcactgtaa taatccag                                  38

<210> SEQ ID NO 23
<211> LENGTH: 39
<212> TYPE: DNA
<213> ORGANISM: Artificial
<220> FEATURE:
<223> OTHER INFORMATION: synthetic

<400> SEQUENCE: 23
atttaggtga cactatagaa attactcctt aatgtcagc                                 39

<210> SEQ ID NO 24
<211> LENGTH: 19
<212> TYPE: DNA
<213> ORGANISM: Artificial
<220> FEATURE:
<223> OTHER INFORMATION: synthetic

<400> SEQUENCE: 24
atggaaggtc acactaggg                                                      19

<210> SEQ ID NO 25
<211> LENGTH: 18
<212> TYPE: DNA
<213> ORGANISM: Artificial
<220> FEATURE:
<223> OTHER INFORMATION: synthetic

<400> SEQUENCE: 25
aagatgatcc gacaagtg                                                       18

<210> SEQ ID NO 26
<211> LENGTH: 40
<212> TYPE: DNA
<213> ORGANISM: Artificial
<220> FEATURE:
<223> OTHER INFORMATION: synthetic

<400> SEQUENCE: 26
taatacgact cactataggg agtactgtag atgtggctcg                                40

<210> SEQ ID NO 27
<211> LENGTH: 40
<212> TYPE: DNA
<213> ORGANISM: Artificial
<220> FEATURE:
<223> OTHER INFORMATION: synthetic

<400> SEQUENCE: 27
atttaggtga cactatagaa gagacaggat caggtcagcg                                40

<210> SEQ ID NO 28

```
<211> LENGTH: 19
<212> TYPE: DNA
<213> ORGANISM: Artificial
<220> FEATURE:
<223> OTHER INFORMATION: synthetic

<400> SEQUENCE: 28
tggcaatagc attgcattc                                                      19

<210> SEQ ID NO 29
<211> LENGTH: 18
<212> TYPE: DNA
<213> ORGANISM: Artificial
<220> FEATURE:
<223> OTHER INFORMATION: synthetic

<400> SEQUENCE: 29
ggtaacctca tttcccca                                                       18

<210> SEQ ID NO 30
<211> LENGTH: 41
<212> TYPE: DNA
<213> ORGANISM: Artificial
<220> FEATURE:
<223> OTHER INFORMATION: synthetic

<400> SEQUENCE: 30
taatacgact cactataggg ttgaacttcc ctccctccct g                             41

<210> SEQ ID NO 31
<211> LENGTH: 38
<212> TYPE: DNA
<213> ORGANISM: Artificial
<220> FEATURE:
<223> OTHER INFORMATION: synthetic

<400> SEQUENCE: 31
atttaggtga cactatagaa ttcagaacac aaagatca                                 38

<210> SEQ ID NO 32
<211> LENGTH: 20
<212> TYPE: DNA
<213> ORGANISM: Artificial
<220> FEATURE:
<223> OTHER INFORMATION: synthetic

<400> SEQUENCE: 32
ttggcaggtg gggcaggaga                                                     20

<210> SEQ ID NO 33
<211> LENGTH: 18
<212> TYPE: DNA
<213> ORGANISM: Artificial
<220> FEATURE:
<223> OTHER INFORMATION: synthetic

<400> SEQUENCE: 33
cctatcctgg ctgtgtcc                                                       18

<210> SEQ ID NO 34
<211> LENGTH: 37
<212> TYPE: DNA
<213> ORGANISM: Artificial
<220> FEATURE:
<223> OTHER INFORMATION: synthetic

<400> SEQUENCE: 34
```

```
taatacgact cactataggg aggagaccct gtaggag                               37

<210> SEQ ID NO 35
<211> LENGTH: 38
<212> TYPE: DNA
<213> ORGANISM: Artificial
<220> FEATURE:
<223> OTHER INFORMATION: synthetic

<400> SEQUENCE: 35
atttaggtga cactatagaa ctcgcccgca gcagctgc                              38

<210> SEQ ID NO 36
<211> LENGTH: 17
<212> TYPE: DNA
<213> ORGANISM: Artificial
<220> FEATURE:
<223> OTHER INFORMATION: synthetic

<400> SEQUENCE: 36
accagggaga ggctggc                                                     17

<210> SEQ ID NO 37
<211> LENGTH: 18
<212> TYPE: DNA
<213> ORGANISM: Artificial
<220> FEATURE:
<223> OTHER INFORMATION: synthetic

<400> SEQUENCE: 37
ctcccgggcc agcctcac                                                    18

<210> SEQ ID NO 38
<211> LENGTH: 40
<212> TYPE: DNA
<213> ORGANISM: Artificial
<220> FEATURE:
<223> OTHER INFORMATION: synthetic

<400> SEQUENCE: 38
taatacgact cactataggg tgaactcccc ccacggaagg                            40

<210> SEQ ID NO 39
<211> LENGTH: 39
<212> TYPE: DNA
<213> ORGANISM: Artificial
<220> FEATURE:
<223> OTHER INFORMATION: synthetic

<400> SEQUENCE: 39
atttaggtga cactatagaa gttcacctgt actggtgga                             39

<210> SEQ ID NO 40
<211> LENGTH: 43
<212> TYPE: DNA
<213> ORGANISM: Artificial
<220> FEATURE:
<223> OTHER INFORMATION: synthetic

<400> SEQUENCE: 40
gctcggctgc ggccgctcac tacataactg tacaccttgt cct                        43

<210> SEQ ID NO 41
<211> LENGTH: 37
<212> TYPE: DNA
<213> ORGANISM: Artificial
<220> FEATURE:
```

```
<223> OTHER INFORMATION: synthetic

<400> SEQUENCE: 41
ggaattcacc atgggcactg agtataaact tgtggtg                                37

<210> SEQ ID NO 42
<211> LENGTH: 20
<212> TYPE: DNA
<213> ORGANISM: Artificial
<220> FEATURE:
<223> OTHER INFORMATION: synthetic

<400> SEQUENCE: 42
tactcctctt gacctgctgt                                                   20

<210> SEQ ID NO 43
<211> LENGTH: 22
<212> TYPE: DNA
<213> ORGANISM: Artificial
<220> FEATURE:
<223> OTHER INFORMATION: synthetic

<400> SEQUENCE: 43
aagaaagccc cccccagttc tc                                                22

<210> SEQ ID NO 44
<211> LENGTH: 55
<212> TYPE: DNA
<213> ORGANISM: Artificial
<220> FEATURE:
<223> OTHER INFORMATION: synthetic

<400> SEQUENCE: 44
acggaattca ccatgactga gtataaactt gtggtggttg gagctgttgg cgtag            55

<210> SEQ ID NO 45
<211> LENGTH: 22
<212> TYPE: DNA
<213> ORGANISM: Artificial
<220> FEATURE:
<223> OTHER INFORMATION: synthetic

<400> SEQUENCE: 45
aagaaagccc ttcccagttc tc                                                22

<210> SEQ ID NO 46
<211> LENGTH: 18
<212> TYPE: DNA
<213> ORGANISM: Artificial
<220> FEATURE:
<223> OTHER INFORMATION: synthetic

<400> SEQUENCE: 46
ttgggtcgcg gttcttgt                                                     18
```

RAS MUTATION AND COMPOSITIONS AND METHODS RELATED THERETO

CROSS-REFERENCE TO RELATED APPLICATIONS

This application is a continuation of U.S. patent application Ser. No. 11/684,290, filed Mar. 9, 2007, now U.S. Pat. No. 7,745,128, which claims the benefit of priority under 35 U.S.C. §119(e) from U.S. Provisional Application No. 60/786,568, filed Mar. 27, 2006. The entire disclosure of each of U.S. patent application Ser. No. 11/684,290 and U.S. Provisional Application No. 60/786,568 is incorporated herein by reference.

REFERENCE TO SEQUENCE LISTING

This application contains a Sequence Listing submitted electronically as a text file by EFS-Web. The text file, named "3923-13-1_ST25", has a size in bytes of 36 KB, and was recorded on 6 May 2010. The information contained in the text file is incorporated herein by reference in its entirety pursuant to 37 CFR §1.52(e)(5).

BACKGROUND OF THE INVENTION

Neoplasia, or a process of rapid cellular proliferation resulting in new, abnormal growth, is a characteristic of many diseases which can be serious, and sometimes, life-threatening. Typically, neoplastic growth of cells and tissues is characterized by greater than normal proliferation of cells, wherein the cells continue to grow even after the instigating factor (e.g., tumor promoter, carcinogen, virus) is no longer present. The cellular growth tends to show a lack of structural organization and/or coordination with the normal tissue and usually creates a mass of tissue (e.g., a tumor) that may be benign or malignant.

Ras mutations are common in pulmonary adenocarcinomas of humans, mice, rats and hamsters. In fact, mutations in the ras proto-oncogene family are the most common oncogene-related mutations in human cancer and in tumors in experimental animals. It is known that there are several different mutations in the oncogenes of the ras gene family that can be associated with a tumor cell phenotype in nature. Mutations at the codon encoding amino acid 12 in the Ras protein are found in 78% of pancreatic cancers, 34% of colorectal cancers, 40% of non-small cell lung adenocarcinomas, and 24% of ovarian cancers. Ras mutations at amino acids 13, 59 and 61 are also found in a variety of cancers (e.g., see Lu et al., Cancer Res. 2004 Aug. 1; 64(15):5084-8; Abrams et al, Sem Oncol 1996 23, 118-134; Friday and Adjei, Biochim Biophys Acta 2005 1756, 127-144). Aberrant signaling through the Ras oncogene product pathway plays an important role in uncontrolled cell proliferation and tumorigenesis. These well-characterized mutations at codons 12, 13 and 61 cause constitutive Ras activation.

Malignant cellular growth, or malignant tumors, are a leading cause of death worldwide, and the development of effective therapy for neoplastic disease is the subject of a large body of research. Although a variety of innovative approaches to treat and prevent cancers have been proposed, many cancers continue to cause a high rate of mortality and may be difficult to treat or relatively unresponsive to conventional therapies. Therefore, there is a continuing need in the art for the identification of additional cancer risk factors and methods for early diagnosis and therapy for cancers.

BRIEF DESCRIPTION OF THE FIGURES

FIG. 4 is a schematic drawing illustrating the crystal structure from a codon 12 mutant form of H-Ras (G12D) (left) compared to the structure of a codon 61 mutant form of H-Ras (Q61L) (right). The arrows point to the estimated position of the amino acids 12, 61 and 76 in the represented tertiary structures.

SUMMARY OF THE INVENTION

Figure 1:
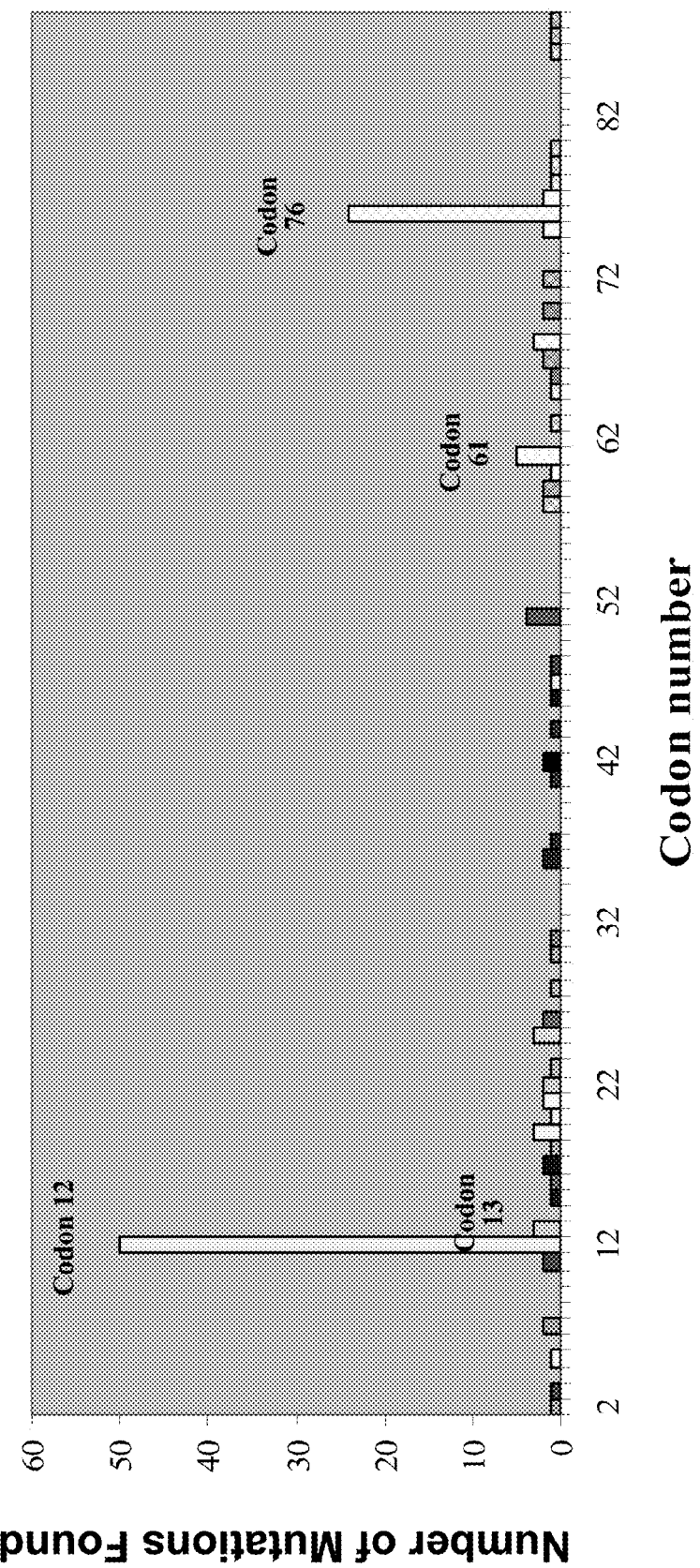
FIG. 1 is a chart showing the catalogue of Ras mutations found by genotyping tumors from patients with colorectal, pancreatic or non-small cell lung cancer.

One embodiment of the present invention relates to an isolated nucleic acid molecule comprising a nucleic acid sequence encoding an amino acid sequence comprising at least 5 contiguous amino acids of a mutant Ras protein. The amino acid sequence contains the amino acid position 76 with respect to a wild-type K-ras, N-ras or H-ras protein, and wherein the amino acid at position 76 is mutated as compared to the wild-type protein. In one aspect, the amino acid at position 76 is mutated from a glutamate to a non-glutamate amino acid residue selected from the group consisting of: glycine, lysine, and glutamine. In one aspect, the non-glutamate amino acid residue is glycine. In one aspect, the amino acid sequence differs from any one of SEQ ID NO:3, SEQ ID NO:5, SEQ ID NO:7, SEQ ID NO:9, SEQ ID NO:11, or SEQ ID NO:13 by a substitution of a non-glutamate amino acid for the glutamate at position 76 of said SEQ ID NO:3, SEQ ID NO:5, SEQ ID NO:7, SEQ ID NO:9, SEQ ID NO:11, or SEQ ID NO:13. In one aspect, the amino acid sequence further comprises at least 5 contiguous amino acid residues of a mutant Ras protein, wherein the amino acid sequence contains the amino acid position selected from the group consisting of 12, 13, 59 and 61 with respect to a wild-type K-ras, N-ras or H-ras protein, and wherein the amino acid at the position is mutated as compared to the wild-type protein.

In one aspect of this embodiment, the amino acid sequence further comprises at least 5 contiguous amino acids of a mutant Ras protein, wherein the amino acid sequence contains the amino acid at position 12 with respect to a wild-type K-ras, N-ras or H-ras protein, and wherein the amino acid at position 12 is mutated as compared to the wild-type protein. In one aspect, the amino acid at positions 12 or 13 are mutated from a glycine to a non-glycine amino acid residue. In one aspect, the non-glycine amino acid residue is selected from: valine, cysteine, aspartate, arginine, serine, and alanine.

In another aspect of this embodiment, the nucleic acid sequence encodes a fusion protein comprising two or more domains, wherein one of the domains comprises the at least 5 amino acids of the mutant Ras protein comprising the mutation at position 76, and wherein each additional domain consists of an immunogen. In one aspect, the immunogen is a tumor antigen. In one aspect, the tumor antigen is a Ras protein or immunogenic fragment thereof comprising at least one mutation relative to a wild-type Ras amino acid sequence. In one aspect, the tumor antigen is a Ras protein or immunogenic fragment thereof comprising positions 12 or 13 with respect to the wild-type Ras amino acid sequence, wherein the amino acid at positions 12 or 13 is mutated from a glycine residue to a non-glycine residue. In another aspect, the tumor antigen is selected from the group consisting of: (a) a peptide comprising at least from positions 8-16 of a Ras protein, wherein the amino acid residue at position 12 with respect to the wild-type Ras protein is mutated; (b) a peptide comprising at least from positions 9-17 of a Ras protein, wherein the amino acid residue at position 13 with respect to the wild-type Ras protein is mutated; (c) a peptide comprising at least from positions 55-63 of a Ras protein, wherein the amino acid residue at position 59 with respect to the wild-type Ras protein is mutated; (d) a peptide comprising at least from positions 57-65 of a Ras protein, wherein the amino acid residue at position 61 with respect to the wild-type Ras protein is mutated; (e) a peptide comprising at least from positions 69-77 of a Ras protein, wherein the amino acid residue at position 73 with respect to the wild-type Ras protein is mutated; (f) a peptide comprising at least from positions 70-78 of a Ras protein, wherein the amino acid residue at position 74 with respect to the wild-type Ras protein is mutated; (g) a peptide comprising at least from positions 71-79 of a Ras protein, wherein the amino acid residue at position 75 with respect to the wild-type Ras protein is mutated; (h) a peptide comprising at least from positions 73-81 of a Ras protein, wherein the amino acid residue at position 77 with respect to the wild-type Ras protein is mutated; and (i) a peptide comprising at least from positions 74-82 of a Ras protein, wherein the amino acid residue at position 78 with respect to the wild-type Ras protein is mutated.

In one aspect of this embodiment, the nucleic acid sequence encodes a fusion protein comprising the amino acid sequence of SEQ ID NO:14. In another aspect, the nucleic acid sequence encodes a fusion protein comprising the amino acid sequence of SEQ ID NO:15.

Another embodiment of the invention relates to an isolated nucleic acid molecule comprising at least 5 contiguous amino acids of a nucleic acid sequence encoding Ras (H-Ras, N-Ras or K-Ras), wherein the proline at position 73 of Ras (P73), the threonine at position 74 (T74), the glycine at position 75 (G75), the glycine at position 77 (G77), and/or the phenylalanine at position 78 (F78) of the Ras amino acid sequence is mutated. Also encompassed by the invention are nucleic acid molecules encoding any fragment of Ras comprising any one or more of these mutation, which nucleic acid molecule is useful in any screening, diagnostic or therapeutic application. Preferably, the amino acid at any one or more of these positions is substituted with a different amino acid than the one that occurs at this position in the wild-type sequence of Ras.

In another embodiment, the invention provides isolated nucleic acid molecules comprising a nucleic acid sequence encoding Ras proteins (H-ras, N-ras or K-ras) containing any one or more of the mutations at position 59, 61, 73, 74, 75, 76, 77 or 78 (or a portion thereof), and one or more additional mutations at a different position in Ras. A preferred combination of mutations is a G12 mutation and/or a G13 mutation with any one or more of the mutations at positions 59, 61, 73, 74, 75, 76, 77 or 78. In another embodiment, the invention provides a combination of different nucleic acid molecules, at least one of which encodes Ras (or a portion thereof) containing one or more mutations at a position selected from 59, 61, 73, 74, 75, 76, 77 or 78 (and preferably selected from any one of positions 73-78), and one or more additional nucleic acid molecules containing one or more additional mutations, including, but not limited to, a mutation at G12 and a mutation at G13.

In one embodiment of the invention, any of the above-described nucleic acid molecules can be an oligonucleotide probe or a primer.

Another embodiment of the invention relates to a recombinant nucleic acid molecule comprising any of the above-described nucleic acid molecules, operatively linked to at least one expression control sequence.

Yet another embodiment of the invention relates to a recombinant cell that has been transfected with any of the above-described recombinant nucleic acid molecules. In one aspect, recombinant cell of Claim 20, wherein the cell is a yeast.

Another embodiment of the present invention relates to an isolated protein or peptide encoded by the isolated nucleic acid molecule of any of the above-identified nucleic acid molecules. In one embodiment, the isolated protein or peptide is part of a fusion protein.

Another embodiment of the invention relates to an isolated nucleic acid molecule that is fully complementary to any of the above-described nucleic acid sequences.

Yet another embodiment of the invention relates to a vaccine comprising any of the above-described nucleic acid molecules.

Another embodiment of the invention relates to a vaccine comprising any of the above-described proteins or peptides. In one aspect, the vaccine further comprises a yeast vehicle. In another aspect, the yeast vehicle recombinantly expresses the protein or peptide. In one aspect, the vaccine further comprises a dendritic cell, wherein the dendritic cell has been loaded intracellularly with the yeast vehicle and the protein or peptide.

Yet another embodiment of the invention relates to a vaccine comprising: (a) a yeast vehicle; and (b) a fusion protein comprising a mutant Ras protein or fragment thereof, wherein the protein or fragment thereof contains the amino acid position 76 with respect to a wild-type K-ras, N-ras or H-ras protein, and wherein the amino acid at position 76 is mutated as compared to the wild-type protein, wherein expression of the fusion protein is under the control of the Cup1 promoter. The fusion protein is expressed by the yeast vehicle. In one aspect, the fusion protein further comprises a second mutant Ras protein or fragment thereof, wherein the second protein or fragment thereof contains the amino acid position 12 with respect to a wild-type K-ras, N-ras or H-ras protein, and wherein the amino acid at position 12 is mutated as compared to the wild-type protein.

In one aspect, the fusion protein comprises the following proteins or fragments, fused in frame: (i) a mutant Ras protein or fragment thereof, wherein the protein or fragment contains the amino acid position 12 with respect to a wild-type K-ras, N-ras or H-ras protein, and wherein the glycine at position 12 is substituted with a cysteine; (ii) a mutant Ras protein or fragment thereof, wherein the protein or fragment contains the amino acid position 61 with respect to a wild-type K-ras, N-ras or H-ras protein, and wherein the glutamine at position 61 is substituted with an arginine; (iii) a mutant Ras protein or fragment thereof, wherein the protein or fragment contains the amino acid position 12 with respect to a wild-type K-ras, N-ras or H-ras protein, and wherein the glycine at position 12 is substituted with an aspartate; (iv) a mutant Ras protein or fragment thereof, wherein the protein or fragment contains the amino acid position 12 with respect to a wild-type K-ras, N-ras or H-ras protein, and wherein the glycine at position 12 is substituted with a valine; (v) a mutant Ras protein or fragment thereof, wherein the protein or fragment contains the amino acid position 12 with respect to a wild-type K-ras, N-ras or H-ras protein, and wherein the glycine at position 12 is substituted with an arginine; and (vi) a mutant Ras protein or fragment thereof, wherein the protein or fragment contains the amino acid position 76 with respect to a wild-type K-ras, N-ras or H-ras protein, and wherein the glutamate at position 76 is substituted with a glycine.

In one aspect, the fusion protein comprises the following proteins or fragments, fused in frame: (i) a mutant Ras protein or fragment thereof, wherein the protein or fragment contains the amino acid position 12 with respect to a wild-type K-ras, N-ras or H-ras protein, and wherein the glycine at position 12 is substituted with an arginine; and (ii) a mutant Ras protein or fragment thereof, wherein the protein or fragment contains the amino acid position 76 with respect to a wild-type K-ras, N-ras or H-ras protein, and wherein the glutamate at position 76 is substituted with a glycine.

In one aspect, the fusion protein comprises the amino acid sequence of SEQ ID NO:14. In another aspect, the fusion protein comprises the amino acid sequence of SEQ ID NO:15.

Yet another embodiment of the invention relates to an antibody or antigen binding fragment thereof that selectively binds to any one of the above-described mutant Ras proteins or peptides.

Another embodiment of the invention relates to an aptamer that selectively binds to any one of the above-described mutant Ras proteins or peptides.

Yet another embodiment of the invention relates to an siRNA molecule that catalyzes the selective cleavage of RNA transcribed by any of the above-described nucleic acid molecules, or of RNA transcribed by a ras gene encoding any of the above-described mutant Ras proteins, and particularly, a mutant Ras protein comprising an amino acid sequence that differs from a wild-type K-ras, N-ras or H-ras amino acid sequence by at least a mutation at position 76 with respect to the wild-type amino acid sequence.

Another embodiment of the invention relates to a ribozyme that selectively catalyzes the inactivation of above-described nucleic acid molecules, or of a ras gene encoding any of the above-described mutant Ras proteins, and particularly, the mutant Ras protein comprising an amino acid sequence that differs from a wild-type K-ras, N-ras or H-ras amino acid sequence by at least a mutation at position 76 with respect to the wild-type amino acid sequence.

Yet another embodiment of the invention relates to an antisense nucleic acid molecule that hybridizes under very high stringency conditions to and inhibits the expression of any of the above-described nucleic acid molecules or of a ras gene encoding any of the above-described mutant Ras protein, and particularly the mutant Ras protein comprising an amino acid sequence that differs from a wild-type K-ras, N-ras or H-ras amino acid sequence by at least a mutation at position 76 with respect to the wild-type amino acid sequence.

Yet another embodiment of the invention relates to method to prevent or treat a cancer, comprising administering to an animal that has or is at risk of developing a cancer, any of the above-described vaccines.

Another embodiment of the invention relates to a method to prevent or treat a cancer, comprising administering to an animal that has or is at risk of developing a cancer, any of the above-described aptamers, any of the above-described siRNAs, any of the above-described ribozymes, or any of the above-described antisense nucleic acid molecules.

Another embodiment of the invention relates to a method to prevent or treat a cancer, comprising administering to an animal that has or is at risk of developing a cancer, a compound that inhibits the expression of a mutant Ras protein, wherein the mutant Ras protein comprises an amino acid sequence that differs from a wild-type K-ras, N-ras or H-ras amino acid sequence by at least a mutation at position 76 with respect to the wild-type amino acid sequence.

Yet another embodiment of the invention relates to a method to prevent or treat a cancer, comprising administering to an animal that has or is at risk of developing a cancer, a compound that initiates or triggers GTP hydrolysis of a mutant Ras protein, wherein the mutant Ras protein comprises an amino acid sequence that differs from a wild-type K-ras, N-ras or H-ras amino acid sequence by at least a mutation at position 76 with respect to the wild-type amino acid sequence.

Another embodiment of the invention relates to a method for the diagnosis of a tumor comprising detecting expression or activity of a mutant Ras protein or nucleic acid sequence encoding said Ras protein in a test sample from a patient to be diagnosed, wherein the Ras protein comprises a mutation at position 76 with respect to the wild-type Ras amino acid sequence. Detection of the mutant Ras protein or nucleic acid sequence encoding said Ras protein in the test sample indicates the presence of tumor cells or potential therefore in the test sample. In one aspect, the Ras protein comprises a substitution of a glycine for the glutamate at position 76 in wild-type protein. In one aspect, the method further comprises detecting whether the Ras protein also comprises a mutation at position 12 with respect to the wild-type Ras amino acid sequence, wherein detection of a mutation at position 76 and position 12 indicates the presence of tumor cells or potential therefore in the test sample, and further indicates a more aggressive tumor in the patient as compared to tumor cells harboring a Ras protein with only one mutation or no mutation at these positions. In one aspect, the step of detecting comprises detecting a nucleic acid sequence encoding the Ras mutation in the test sample. In one aspect, the step of detecting comprises PCR amplification of a genomic DNA template encoding the mutation or in situ PCR amplification of DNA sequences encoding the mutation. In one aspect, the step of detecting is by a method selected from the group consisting of polymerase chain reaction (PCR), reverse transcriptase-PCR (RT-PCR), in situ hybridization, Northern blot, sequence analysis, gene microarray analysis, and detection of a reporter gene. In one aspect, the level of nucleic acid sequence encoding the mutant Ras protein is determined by contacting nucleic acids isolated from the test sample with a primer or probe that selectively binds to the nucleic acid sequence encoding the mutant Ras protein, and detecting whether the nucleic acid sequence encoding the mutated Ras protein is bound by the primer or probe. In one aspect, the level of mutant Ras protein is determined by contacting the test sample with an antibody or a fragment thereof or an aptamer that selectively binds specifically to the mutant Ras protein, and detecting whether the antibody or fragment thereof or aptamer has bound to the mutant Ras protein. In one aspect, the test sample is from a patient being diagnosed for cancer and wherein the test sample is compared to a negative control sample. In one aspect, the test sample is immobilized on a substrate. In one aspect, the method is used to diagnose cancer in the patient. In one aspect, the method is used to determine the prognosis for cancer in the patient. In another aspect, the method is used to determine the susceptibility of the patient to a therapeutic treatment.

Another embodiment of the invention relates to a kit for use in the diagnostic methods of the present invention. The kit preferably contains any reagent useful for detecting the presence or absence of the Ras (protein) or ras (nucleic acid) mutation according to the present invention in a test sample, and preferably includes an oligonucleotide probe, PCR primers, or an antibody, antigen binding peptide, or aptamer, that binds to the biomarker (i.e., the mutated ras gene, RNA, cDNA, or protein encoded thereby). The kit can include any reagent needed to perform a diagnostic method envisioned herein. The kit can also include reagents for the detection of other cancer biomarkers, such as the previously described Ras mutations, or any other suitable target for cancer diagnosis, even for cancers having causes or contributions unrelated to the Ras mutation described herein.

Yet another embodiment of the invention relates to a method for identifying a compound for preventing or treating cancer, comprising identifying an inhibitor of a target Ras protein or a nucleic acid molecule encoding the target Ras protein, wherein the target Ras protein comprises a mutation at position 76 relative to a wild-type Ras protein. In one aspect, the mutation is a substitution of a non-glutamate amino acid selected from the group consisting of a glycine, a lysine and a glutamine for the glutamate at position 76 in the wild-type protein. In one aspect, the step of identifying comprises identifying an inhibitor of expression or activity of the target Ras protein. In one aspect, the step of detecting is selected from the group consisting of: detecting translation or activity of the target Ras protein in the presence of the putative regulatory compound; and detecting expression of a gene encoding the target Ras protein in the presence of the putative regulatory compound. In one aspect, the method includes the steps of: (a) contacting a host cell with a putative regulatory compound, wherein the host cell expresses the target Ras protein or a biologically active fragment thereof; and (b) detecting whether the putative regulatory compound triggers GTP hydrolysis of the target Ras protein or biologically active fragment thereof, wherein a putative regulatory compound that triggers GTP hydrolysis of the target Ras protein as compared to in the absence of the compound is indicated to be a candidate compound for the prevention or treatment of cancer. In one aspect, the host cell is a tumor cell line.

Another embodiment of the invention relates to a method for identifying a compound for preventing or treating cancer, comprising identifying compound that triggers GTP hydrolysis in a cell expressing a target mutated Ras protein, but not in a cell expressing a wild-type Ras protein, wherein the target mutated Ras protein comprises a mutation at position 76 relative to a wild-type Ras protein.

In one aspect of either of the above-methods of identifying, the putative regulatory compound can be selected from: an aptamer, an siRNA molecule, an antisense nucleic acid molecule, a ribozyme, an antibody or antigen binding fragment thereof, a conformational antagonist, and a small molecule inhibitor.

DETAILED DESCRIPTION OF THE INVENTION

The present invention generally relates to the discovery by the present inventors of a newly discovered mutation in human Ras that is believed to contribute to or cause cancer in certain individuals who have the mutation, which includes multiple variants of this particular mutation. Specifically, the inventors have discovered that a mutation at amino acid number 76 (i.e., encoded by codon 76) in the human Ras sequence (K-, N-, or H-Ras) can be identified in a significant percentage of patient tumors and increases oncogenicity of the tumors. To the best of the present inventors' knowledge, this particular Ras mutation has not been previously identified. The invention also relates to the discovery by the present inventors that when this newly discovered mutation is present in a tumor cell at the same time as a second, previously described, Ras mutation, particularly a codon 12 mutation, the combination of mutations synergizes to increase the oncogenicity of tumors bearing such mutations. In particular, the combination of mutations has a synergistic effect with respect to enhancement of tumor growth, as compared to either mutation alone, which has been demonstrated both in vitro and in vivo. Accordingly, the present invention provides nucleic acid molecules and proteins that utilize these discoveries, as well as a variety of research, diagnostic and therapeutic tools and methods of use based on these discoveries, as described in detail below.

Specifically, K-, N- and H-ras DNA sequences were characterized for the presence of tumor-associated mutations by nested PCR amplification and direct sequencing of exons 2 and 3 from tumors of 149 subjects with pancreas (68% detected with codon 12, 13 or 61 ras mutations), colorectal (40% detected with codon 12, 13 or 61 ras mutations) or non-small cell lung carcinoma (NSCLC) (9% detected with codon 12, 13 or 61 ras mutations) cancers in a Phase 1 immunotherapy trial of whole, heat-killed yeast expressing mutated Ras proteins (also referred to herein as Tarmogens). A new ras mutation at codon 76 was detected in 24 subjects from all 3 cancer types, with 22 being E76G mutations, while 1 tumor harbored an E76K mutation and 1 tumor harbored an E76Q mutation. Double combinations of E76 plus the previously described mutations at codons 12 or 13 were identified in 8 tumors.

More specifically, as shown in Table 1 (see Example 1), 5 of 33 (~15%) of the lung tumors, 12 of 85 colorectal tumors (~14%), and 7 of 31 (~22.5%) of the pancreas tumors, for which full sequencing information in all three Ras genes (exons 2 and 3) was obtained, exhibited mutations at amino acid number 76 (i.e., encoded by codon 76) in the human Ras sequence (Ras E76 mutation). One of the lung colorectal tumors had mutations at amino acid 76 in both K- and H-ras. In the case of the colorectal tumors, 10 of the 12 mutations at amino acid 76 were a mutation from glutamate to glycine (E76G), one mutation was a glutamate to lysine mutation (E76K), and one mutation was a glutamate to glutamine mutation (E76Q). All of the E76 mutations in the lung and pancreas tumors were E76G mutations. Overall, the occurrence of mutations at Ras amino acid 76 in the tumors studied in this Phase I trial was second only to the occurrence of mutations at Ras amino acid 12 (see FIG. 1). Frequencies of the previously known Ras mutations at positions 12, 13 and 61 in this same set of tumor samples are shown in Table 2 (see Example 1). The E76 mutations occurred primarily in the K-ras or H-ras exon 3 genes, although the E76K mutation occurred in exon 3 of the N-ras gene. Also, as mentioned above, double combinations of E76 plus the previously described mutations at codons 12 or 13 were identified in 8 tumors. Together, these data indicated that mutations at codon 76 of the Ras gene were contributing to or causing the cancer in these individuals.

Additional studies by the inventors have demonstrated that indeed, the expression of a codon 76 Ras mutation in murine K-ras in Balb3T3 cells increased colony formation in soft agar by these cells in vitro. Specifically, Ras E76G and E76K mutations were confirmed as transforming in non-clinical studies. Of particular interest, coupling codon 76 and 12 mutations resulted in tumor growth synergy (i.e., the combination of mutations synergized to significantly increase the oncogenicity of tumors containing Ras with these double mutations). Moreover, when various mutant K-ras genes were injected into BALB/c nude mice, the double G12-E76 Ras mutation (specifically a G12V-E76G mutation in this experiment) led to significantly accelerated tumor growth compared to tumor cells bearing any single mutation. Having made these discoveries, the present inventors believe that, without being bound by theory, the E76 mutation may result in an activated Ras oncoprotein.

The previously described mutations at codon 12 or codon 61 block γ-phosphate release from GTP or prevent Ras-GAP protein binding to Ras to trigger GTP hydrolysis, respectively. When the known crystal structure of Ras was examined by the present inventors for the position of amino acid 76, it was seen that this residue is located at the end of the loop designated as Switch 2 or Loop 4 (see FIG. 4). Referring to FIG. 4, the estimated position of amino acids 12, 13, 61 and 76 are highlighted in the protein tertiary structure (e.g. for amino acid positioning within Ras crystal structure see multiple structures in the RSSB Protein Data Bank (PDB), or Franken, S M et al, *Biochemistry* 1993, 32:8411-20). This schematic drawing highlights the change in the Ras protein crystal structure due to a codon 12 mutation in H-Ras (G12D) (left) compared to the wild-type (G12) sequence for that domain (right). In addition, the altered structure of a domain harboring codon 61 mutant form of H-Ras (Q61L) (right) is evident by comparison to the wild-type sequence for that domain (left). The proximal end of Loop 4 harbors amino acid 61, where mutations have been defined prior to the present invention as activating the Ras oncoprotein in animal and human cancers (e.g., see Lu et al., Cancer Res. 2004 Aug. 1; 64(15):5084-8; see also numerous clinical studies—also two colorectal cancer patients in the current trial described in Example 1 have mutations at Ras codon 61). This loop in the Ras protein is involved with binding to GTPase activating proteins (Ras-GAPs) that trigger the hydrolysis of GTP bound to the activated Ras protein, to convert Ras to the inactive GDP-bound form. The inability to trigger GTP hydrolysis maintains the Ras protein in the activated state (GTP-bound) and therefore, signals for cell proliferation are sent constitutively. Thus, the mutation at codon 61 prevents the interacting proteins from turning off the activated state. The mutation at codon 12 interferes with release of the terminal phosphate, so that the protein remains in the activated state. The activated state is thus a conformation of the Ras protein (with GTP bound) that is capable of associating with downstream effector proteins to send the proliferation signal from upstream activators, or in the case of the mutated Ras proteins, to deliver a constitutive activation signal.

The positioning of amino acid 76 at the other 'hinge' of the critical Switch 2/Loop 4 (GAP-binding) domain is consistent with the present inventors' belief that mutations in this amino acid will similarly interfere with Ras function. For instance, a mutation from glutamate to glycine (Ras E76G mutation), for example, will change the Ras sequence from glycine-glutamate-glycine (GEG for single letter code of codons 74-76) to glycine-glycine-glycine (GGG for single letter code of 'mutated' codons 74-76). The introduction of glycines into alpha-helical structures is known to interfere biochemically with the maintenance of the alpha-helical loop structures. Therefore, the change from GEG to GGG is predicted to disrupt the alpha-helix of loop 4/Switch 2, and will interfere with conformational changes needed to promote GTP hydrolysis. Similarly, changing the glutamate to lysine, or glutamate to glutamine at amino acid 76 (E76K or E76Q, respectively) will alter the charge of the amino acid, which also has the potential to disrupt protein structure and function if the negative charge of the glutamate were important for intra- or inter-molecular protein-protein interactions. Thus, the observation by the present inventors that a significant fraction of human tumors possess the Ras E76 mutation can be explained by Ras structure and function studies. The identification of codon 76 ras mutations in human tumors accordingly represents a new target for cancer therapy.

These observations have led the inventors to additionally propose herein that the mutations of interest in the E76-related hinge region can also include mutations at amino acids P73, T74, G75, E76, G77, and F78, and that mutations at these positions will have a similar effect on Ras GTP hydrolysis and therefore, on cell proliferation (tumor growth) as the E76 mutation described herein. Accordingly, mutations at codons 73, 74, 75, 77 and 78 also represent a new targets for cancer therapy.

The inventors' results also indicate that tumors bearing double mutations are more likely to exhibit aggressive growth characteristics. Thus, the genotype of double codon 12 and 76 ras mutations in patient tumors is believed to be prognostic of an accelerated malignant phenotype, which has been indicated by the data provided herein. The identification of combination mutations comprising codon 76 ras mutations, accordingly represents yet another new target for cancer therapy. Moreover, because the inventors' data in Example 1 also indicate that mutations at A59 or Q61 of Ras may also be found in conjunction with G12 or G13 mutations, the inventors propose herein that other combinations of mutations at either G12 or G13 (interfering with the release of the terminal phosphate) with any one or more of A59, Q61, or E76, or indeed, with any one of the other amino acids in the same hinge region as E76 (i.e., P73, T74, G75, E76, G77, F78), also exacerbate signaling of cell proliferation through inhibition of Ras GTP hydrolysis and accordingly will lead to a more aggressive tumor phenotype, with increased metastatic potential. This is based on the inventors' belief that the combination of reducing the ability to release cleaved GTP (impact of mutations at positions 12/13) with inability to signal GTPase activity (impact of mutations at positions 59, 61, 73-78 mutations on either side of the Switch 2/Loop 4 region) will exacerbate the signaling of cell proliferation by an order of magnitude, as is indicated by the data provided with respect to the combination of mutations at G12 and E76. This phenotype could occur via two mutations in the same DNA molecule (the same gene) and/or mutations that occur separately on each of the Ras alleles, although the inventors' data indicate that the combination of mutations occurring on the same DNA molecule leads to more aggressive phenotype, and may potentiate malignant metastasis. Accordingly, the present invention includes nucleic acid molecules having any combination of the mutations at position 12 or 13 with the mutations at positions 59, 61, 73, 74, 75, 76, 77 or 78, with combinations between positions 12 or 13 with positions 59, 61 or 76 being particular embodiments of the invention. Proteins or peptides comprising these combinations, and the uses of the nucleic acid molecules and proteins (and related tools) are all encompassed by the invention, as described in more detail below.

Therefore, one embodiment of the present invention relates to an isolated nucleic acid molecule comprising a nucleic acid sequence encoding Ras (H-Ras, N-Ras or K-Ras), wherein the glutamate at position 76 of the Ras amino acid sequence (E76) is mutated. Also encompassed by the invention are nucleic acid molecules encoding any fragment of Ras comprising the position 76 mutation, which nucleic acid molecule is useful in any screening, diagnostic or therapeutic application. Preferably, the amino acid at position 76 is substituted with another amino acid (an amino acid that is not glutamate, or a "non-glutamate amino acid") that can include, but is not limited to, a glycine substitution, a lysine substitution, or a glutamine substitution. In another embodiment, the invention provides isolated nucleic acid molecules comprising a nucleic acid sequence encoding Ras (H-Ras, N-Ras or K-Ras) containing an E76 mutation (or a portion thereof), and one or more additional mutations at a different position in Ras. A preferred combination of mutations is an E76 mutation and a G12 mutation, although this aspect of the invention is not limited to this combination, as described above. In another embodiment, the invention provides a combination of different nucleic acid molecules, at least one of which encodes Ras containing an E76 mutation (or a portion thereof), and one or more additional nucleic acid molecules containing one or more additional mutations, including, but not limited to, a mutation at G12, a mutation at G13, a mutation at A59 and/or a mutation at Q61. Nucleic acid molecules encoding Ras proteins or peptides comprising the position 76 mutation, alone or in conjunction with such additional mutations, are useful, for example, as probes or primers for research or diagnostic tools, to prepare antisense or siRNA molecules (described below) as diagnostic or therapeutic reagents, and/or to encode Ras proteins and peptides for use as research, diagnostic and/or therapeutic reagents, all described in more detail below.

Another embodiment of the invention relates to an isolated nucleic acid molecule comprising a nucleic acid sequence encoding Ras (H-Ras, N-Ras or K-Ras), wherein the proline at position 73 of Ras (P73), the threonine at position 74 (T74), the glycine at position 75 (G75), the glycine at position 77 (G77), and/or the phenylalanine at position 78 (F78) of the Ras amino acid sequence is mutated. Also encompassed by the invention are nucleic acid molecules encoding any fragment of Ras comprising any one or more of these mutation, which nucleic acid molecule is useful in any screening, diagnostic or therapeutic application. Preferably, the amino acid at any one or more of these positions is substituted with a different amino acid than the one that occurs at this position in the wild-type sequence of Ras.

In another embodiment, the invention provides isolated nucleic acid molecules comprising a nucleic acid sequence encoding Ras proteins (H-ras, N-ras or K-ras) containing any one or more of the mutations at position 59, 61, 73, 74, 75, 76, 77 or 78 (or a portion thereof), and one or more additional mutations at a different position in Ras. A preferred combination of mutations is a G12 mutation and/or a G13 mutation with any one or more of the mutations at positions 59, 61, 73, 74, 75, 76, 77 or 78. In another embodiment, the invention provides a combination of different nucleic acid molecules, at least one of which encodes Ras (or a portion thereof) containing one or more mutations at a position selected from 59, 61, 73, 74, 75, 76, 77 or 78 (and preferably selected from any one of positions 73-78), and one or more additional nucleic acid molecules containing one or more additional mutations, including, but not limited to, a mutation at G12 and a mutation at G13.

Nucleic acid molecules encoding Ras proteins or peptides comprising any of the above-described mutations and combinations thereof are useful, for example, as probes or primers for research or diagnostic tools, to prepare antisense or siRNA molecules (described below) as diagnostic or therapeutic reagents, and/or to encode Ras proteins and peptides for use as research, diagnostic and/or therapeutic reagents, all described in more detail below.

Also included in the present invention are proteins encoded by any of the above-identified nucleic acid molecules, including any fragments of a Ras protein that include the position 76 mutation (or any one or more of the mutations at positions 73, 74, 75, 77 or 78), alone or in combination with other mutations, and that are useful in any research, diagnostic or therapeutic application.

The use of the Ras E76 mutation, as well as the use of a mutation at position 73, 74, 75, 77 or 78 or any of the combinations of Ras mutations described herein, can be further expanded to encompass a variety of research, diagnostic and therapeutic tools, including the development of antibodies that selectively bind to Ras proteins having this particular mutation or mutations; the development of aptamers that selectively bind to Ras proteins having this particular mutation or mutations; the development of siRNA or antisense nucleic acid sequences useful as diagnostic reagents or as therapeutic tools for inhibition of the expression of Ras bearing this particular mutation or mutations; the development of therapeutic molecules, including conformational antagonists, that trigger GTP hydrolysis or otherwise compensate for the deficiencies or hyperactivity of these mutant Ras proteins in this regard; and/or the development of animal models, including transgenic animals and cell lines, that express the these mutation or mutations.

Another embodiment of the present invention relates to the use of the Ras E76 mutation, or a mutation at position 73, 74, 75, 77 or 78 or any of the combinations of Ras mutations described herein, as a marker in a diagnostic or prognostic assay for cancer. For example, biological samples can be obtained from a patient who is to be tested for cancer or a risk of developing cancer, and the expression of a Ras bearing the E76 mutation (or a mutation at position 73, 74, 75, 77 or 78) can be analyzed, either at the gene, RNA or protein level. Patients who express a Ras having this mutation will be predicted to be at a higher risk of having cancer or diagnosed as being more likely to have cancer, as compared a person not having such mutation. Furthermore, patients who express a Ras having a mutation at any one of positions 59, 61, 73, 74, 75, 76, 77 or 78 in addition to a second Ras mutation, and particularly a G12 or G13 mutation (with combinations of mutations at E76 and G12 being of particular interest), will be predicted to be at an even higher risk of having cancer, diagnosed as having a more aggressive cancer, or diagnosed to be more likely to have cancer, as compared to a person not having such a combination of mutations in Ras. In addition, the presence or absence of any of the Ras position 73-78 mutations (and particularly, the E76 mutation) and combinations of these mutations or the position 59 or 61 mutation with other mutations (e.g., a G12 mutation or a G13 mutation) can be used to determine cancer therapy for a patient or to predict the outcome of therapy of a patient. For example, a patient having the Ras E76G mutation may be treated in a particular manner or with particular therapeutic compositions based on the presence of the Ras E76 mutation (e.g., by selection of compounds that effect GTP hydrolysis). Indeed, embodiments of the present invention described below are directed to immunotherapeutic approaches based on the identification of this particular mutation or any of the mutations at positions 73-78 or the combinations of mutations described herein. A patient having a combination of an E76 mutation and another mutation, such as a G12 mutation, may be predicted to have a particularly aggressive tumor and/or may promote metastasis of the primary tumor from the site of origin, and can be treated accordingly, including with immunotherapeutic approaches based on the E76 lesion or on this combination of mutations. Other combinations of the G12 or G13 mutation with the mutations in the Switch2/Loop 4 region, as discussed above, are also predicted to indicate particularly aggressive tumors.

Yet another embodiment of the present invention relates to the use of the Ras E76 mutation (or a mutation at position 73, 74, 75, 77 or 78 or any of the combinations of Ras mutations described herein) as a target for therapeutic approaches for the treatment of cancer in a patient. Such therapeutic approaches can include, but are not limited to, chemotherapeutic approaches and immunotherapeutic approaches. For example, based on the proposed mechanism of action of the Ras E76 mutation as discussed above, one can design or propose chemotherapeutic strategies that, for example, enable the hydrolysis of GTP from the Ras protein or otherwise compensate for the inability of Ras to trigger GTP hydrolysis. One would preferably design a compound that was capable of regulating GTP hydrolysis of a mutated Ras protein, without impacting GTP hydrolysis of wild-type, nonmutated Ras protein (described in more detail below). By way of illustration, a variety of synthetic molecules, aptamers, or conformational antagonists can be developed using the information provided herein to trigger GTP hydrolysis of active Ras proteins. In an immunotherapeutic approach, the Ras E76 mutation (or other mutations at positions 73-78) is used in the production or provision of mutated Ras antigens to stimulate an immune response against tumor cells that express this mutated Ras. Combinations of Ras mutations (e.g., E76 and G12) can be used similarly. The mutated Ras protein or peptide or nucleic acid encoding the same can be used as a target in assays to identify novel small molecule or peptide drugs that are predicted to modify the expression or activity of the Ras protein in a tumor cell, for example. Preferred aspects of this embodiment are described below.

Another embodiment of the present invention relates to a prophylactic or therapeutic vaccine or composition and a method of using the same to protect an animal against a cancer. The vaccine or composition can include an antigen comprising one or more immunogenic portions of Ras comprising the E76 mutation described herein (or one or more immunogenic portions of a Ras comprising a mutation at position 73, 74, 75, 77 or 78), alone or in combination with other immunogenic portions of Ras comprising other mutations, or in combination with other immunogens relevant to the tumor to be treated or prevented. The vaccine or composition can also include an antigen comprising one or more immunogenic portions of Ras comprising any of the combinations of Ras mutations described herein, alone or in combination with other immunogens relevant to the tumor to be treated or prevented. Any pharmaceutically acceptable vehicle for delivering such antigen, including any adjuvant, carrier or other delivery vehicle can be included in the vaccine or composition. In one preferred embodiment, the vehicle is a yeast-based vehicle, which is described in detail below. The Ras antigen can be provided in a composition for treatment of any cancer bearing Ras E76 mutations (or a mutation at position 73, 74, 75, 77 or 78 or any of the combinations of Ras mutations described herein), and also as one element of a multi-epitopic, and/or multiple-antigen based product for treatment of a variety of cancers, which may include all cancers bearing Ras E76 mutations (or a mutation at position 73, 74, 75, 77 or 78 or any of the combinations of Ras mutations described herein). As above, other Ras antigens and/or other cancer antigens or immunogenic portions thereof can be included in the vaccine or composition.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); *Casarett and Doull's Toxicology The Basic Science of Poisons*, C. Klaassen, ed., 6th edition (2001), and Vaccines, S. Plotkin and W. Orenstein, eds., $3^{rd}$ edition (1999).

General Definitions

General reference herein to a "Ras mutation", unless otherwise specified, can refer to a mutation in the nucleic acid sequence of the ras gene or a nucleic acid obtained or derived therefrom (e.g., RNA, DNA), as well as a mutation in the amino acid sequence of the Ras protein or a peptide thereof. Reference to a mutation at a particular position of the nucleic acid sequence or amino acid sequence of Ras can be described by reference to the codon or amino acid position number where the mutation occurs, and such references can be used interchangeably (e.g., reference to "codon 76" or "position 76" or "E76" can all be used to refer to the codon in the ras nucleic acid sequence encoding amino acid 76 of Ras or the actual amino acid residue (glutamate) at position 76, where a mutation is being described in either the nucleic acid or amino acid sequence).

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. In addition, an isolated nucleic acid molecule is not a library of nucleic acid molecules, such as a library of nucleic acid molecules produced from a tumor sample. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence)

additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA, siRNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain or portion of a protein.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule of the present invention, or of a size sufficient to encode an amino acid sequence that serves as an immunogenic epitope, is sufficient for use in producing an antibody or antigen binding peptide, or has a biological activity of a natural encoded protein (e.g., Ras) or mutated protein (e.g., a Ras mutant), or fragment thereof. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to be useful in any of the embodiments of the invention described herein.

An isolated nucleic acid molecule of the present invention can be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (e.g., the introduction of a E76G mutation to a Ras amino acid sequence as discussed herein).

A nucleic acid molecule homologue can be produced using a number of methods known to those skilled in the art (see, for example, Sambrook et al., Molecular Cloning: A Laboratory Manual, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

An oligonucleotide probe, or probe, is a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. Hybridization conditions have been described in detail above.

PCR primers are also nucleic acid sequences, although PCR primers are typically oligonucleotides of fairly short length which are used in polymerase chain reactions. PCR primers and hybridization probes can readily be developed and produced by those of skill in the art, using sequence information from the target sequence. (See, for example, Sambrook et al., supra or Glick et al., supra).

Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure.

RNA interference (RNAi) is an approach for gene inactivation via gene silencing, termed "RNA interference" (RNAi). See, for example, Fire et al., *Nature* 391: 806-811 (1998) and U.S. Pat. No. 6,506,559. RNA interference refers to an event which occurs when an RNA polynucleotide acts through endogenous cellular processes to specifically suppress the expression of a gene whose sequence corresponds to that of the RNA. The silencing of the target gene occurs upon the degradation of mRNA by double strand (ds) RNA by the host animal, sometimes through RNAase III Endonuclease digestion. The digestion results in molecules that are about 21 to 23 nucleotides (or bases) in length (or size) although molecular size may be as large as 30 bases. These short RNA species (short interfering RNA or siRNA) mediate the degradation of corresponding RNA messages and transcripts, possibly via an RNAi nuclease complex, called the RNA-induced silencing complex (RISC), which helps the small dsRNAs recognize complementary mRNAs through base-pairing interactions. Following the siRNA interaction with its substrate, the mRNA is targeted for degradation, perhaps by enzymes that are present in the RISC. This type of mechanism appears to be useful to the organisms in inhibiting viral infections, transposon jumping, and similar phenomena, and to regulate the expression of endogenous genes. RNAi activity has been so far documented in plants, insects, nematodes and vertebrates among other organisms. For general background information, see, for example, Schutz et al., *Virology* 344(1): 151-7 (2006); Leonard et al., *Gene Ther.* 13(6):532-40 (2006); Colbere-Garapin et al., *Microbes Infect.* 7(4):767-75 (2005); Wall, *Theriogenology* 57(1):189-201 (2002); El-Bashir, et al., *Nature* 411: 494-498 (2001); Fire, A., et al. *Science* 391: 806-811 (1998); Gitlin et al., *Nature* 418: 430-434 (2002); Gitlin, et al., *J. Virol.* 79:1027-1035 (2005); Kahana, et al., *J. Gen. Virol.* 85, 3213-3217 (2004); Kronke et al., *J. Virol.* 78: 3436-3446 (2004); Leonard et al., *J. Virol.* 79:1645-1654 (2005); and Yokota, et al., *EMBO Rep.* 4: 602-608 (2003).

A ribozyme is an RNA segment that is able to perform biological catalysis (e.g., by breaking or forming covalent bonds). More specifically, ribozymes are antisense RNA molecules that function by binding to the target RNA moiety and inactivate it by cleaving the phosphodiester backbone at a specific cutting site. Such nucleic acid-based agents can be introduced into host cells or tissues and used to inhibit the expression and/or function of mutated Ras proteins.

According to the invention, a recombinant nucleic acid molecule comprises a recombinant vector and a nucleic acid sequence of interest. A recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule may be used to delete, inactivate, or replace an endogenous gene or portion of a gene within the host cell (i.e., used for targeted gene disruption or knock-out technology). Such a vector may also be known in the art, in one aspect, as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to associate with the target gene such that the target gene and the insert may undergo homologous recombination, whereby the endogenous target gene is deleted, inactivated, attenuated (i.e., by at least a portion of the endogenous target gene being mutated or deleted), or replaced.

Typically, a recombinant nucleic acid molecule includes at least one nucleic acid molecule of the present invention operatively linked to one or more expression control sequences. According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those that are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as bacteria and yeast, or into plant cells. In microbial and plant systems, the term "transformation" is used to describe an inherited change due to the acquisition of exogenous nucleic acids by the microorganism or plant and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, and transformation of microbial cells or plant cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, Anal. Biochem. 138, 267-284; Meinkoth et al., ibid., is incorporated by reference herein in its entirety.

Low stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). Moderate stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). High stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). Very high stringency hybridization and washing conditions, as referred to herein, refer to conditions which permit isolation of nucleic acid molecules having at least about 95% nucleic acid sequence identity with the nucleic acid molecule being used to probe in the hybridization reaction (i.e., conditions permitting about 5% or less mismatch of nucleotides). One of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10°C less than for DNA:RNA hybrids. In particular embodiments, stringent hybridization conditions for DNA:DNA hybrids include hybridization at an ionic strength of 6×SSC (0.9 M Na$^+$) at a temperature of between about 20°C and about 35°C (lower stringency), more preferably, between about 28°C and about 40°C (more stringent), and even more preferably, between about 35°C and about 45°C (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30°C and about 45°C, more preferably, between about 38°C and about 50°C, and even more preferably, between about 45°C and about 55°C, with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25°C below the calculated $T_m$ of a particular hybrid, and wash conditions typically include a combination of salt and temperature conditions that are approximately 12-20°C below the calculated $T_m$ of the particular hybrid. One example of hybridization conditions suitable for use with DNA:DNA hybrids includes a 2-24 hour hybridization in 6×SSC (50% formamide) at about 42°C, followed by washing steps that include one or more washes at room temperature in about 2×SSC, followed by additional washes at higher temperatures and lower ionic strength (e.g., at least one wash as about 37°C in about 0.1×-0.5×SSC, followed by at least one wash at about 68°C in about 0.1×-0.5×SSC).

Reference to an isolated protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can include an agonist of a protein or an antagonist of a protein. A homologue can have enhanced, decreased, changed, or substantially similar properties as compared to the naturally occurring protein or peptide. It is noted that homologues can include synthetically produced homologues, naturally occurring allelic variants of a given protein or domain, or homologous sequences from organisms other than the organism from which the reference sequence was derived. Homologues can be the result of natural allelic variation or natural mutation. Homologues can be produced using techniques known in the art for the production of proteins including, but not limited to, direct modifications to the isolated, or synthesized naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide or, for example, complexing a protein or peptide with another compound or tethering the protein, such as by a glycerophosphatidyl inositol (GPI) anchor. Such modifications can be considered to be mutations, for example, if the modification is different than the post-translational modification that occurs in the natural, wild-type protein or peptide.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. 157:105 (1982)), or on the basis of the ability to assume similar polypeptide secondary structure (Chou and Fasman, Adv. Enzymol. 47: 45 (1978)), or tertiary or quaternary structures.

The general use herein of the term "antigen" refers: to any portion of a protein (peptide, partial protein, full-length protein), wherein the protein is naturally occurring or synthetically derived, to fusion proteins or chimeric proteins, to a cellular composition (whole cell, cell lysate or disrupted cells), to an organism (whole organism, lysate or disrupted cells), to a carbohydrate (such as those expressed on cancer cells), or to another molecule, or any portion thereof. An antigen elicits an antigen-specific immune response (e.g., a humoral and/or a cell-mediated immune response) against the same or similar antigens that are encountered within the cells and tissues of an individual to which the antigen is administered. Alternatively, an antigen can act as a toleragen.

When referring to stimulation of an immune response, the term "antigen" can be used interchangeably with the term "immunogen". An immunogen, as used herein, describes an antigen which elicits a humoral and/or cell-mediated immune response (i.e., is antigenic), such that administration of the immunogen to an animal (e.g., via a vaccine of the present invention) mounts an antigen-specific immune response against the same or similar antigens that are encountered within the tissues of the animal.

A "toleragen" is used to describe an antigen that is provided in a form, amount, or route of administration such that there is a reduced or changed immune response to the antigen, and preferably substantial non-responsiveness, anergy, other inactivation, or deletion of immune system cells in response to contact with the toleragen or a cell expressing or presenting such toleragen.

A "vaccinating antigen" can be an immunogen or a toleragen, but is an antigen used in a vaccine (prophylactic or therapeutic), where a biological response (elicitation of an immune response, tolerance) is to be elicited against the vaccinating antigen.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal For example, a single protein can contain multiple different immunogenic domains Immunogenic domains need not be linear sequences within a protein, such as in the case of a humoral immune response.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions). An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms).

"Vaccination" or "immunization" refers to the elicitation (induction) of an immune response against an antigen or immunogenic or toleragenic portion thereof, as a result of administration of the antigen, alone or together with an adjuvant. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a composition (vaccine) of the present invention can be any detectable change in any facet of the immune response (e.g., cell-mediated response, humoral response, cytokine production), as compared to in the absence of the administration of the composition.

A Tarmogen (targeted molecular immunogen) generally refers to a yeast vehicle expressing one or more heterologous antigens extracellularly (on its surface or as a secreted antigen), intracellularly (internally or cytosolically) or both extracellularly and intracellularly. Tarmogens have been generally described in the art. See, e.g., U.S. Pat. No. 5,830,463.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the antigen are any two amino acid residues that are not naturally found flanking the antigen.

According to the present invention, reference to a "heterologous" protein or "heterologous" antigen, including a heterologous fusion protein, in connection with a yeast vehicle of the invention means that the protein or antigen is not a protein or antigen that is naturally expressed by the yeast, although a fusion protein may include yeast sequences or proteins or portions thereof that are naturally expressed by yeast (e.g., an Aga protein as described herein). For example, a fusion protein of a tumor cell Ras protein and a yeast Aga protein is considered to be a heterologous protein with respect to the yeast vehicle for the purposes of the present invention, since such a fusion protein is not naturally expressed by a yeast.

Any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. The heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

The term, "disease" refers to any deviation from the normal health of an animal and includes a state when disease symptoms are present, as well as conditions in which a deviation (e.g., infection, gene mutation, genetic defect, etc.) has occurred, but symptoms are not yet manifested.

An "individual" is a vertebrate, preferably a mammal, more preferably a human. Mammals include, but are not limited to, farm animals, sport animals, pets, primates, mice and rats. The term "individual" can be used interchangeably with the term "animal", "subject" or "patient".

While the following descriptions of aspects of the invention are described in particular with regard to the Ras mutation identified at codon 76 and/or with regard to combinations of Ras mutations including a mutation at codon 76, all aspects of the invention below can also be applied to Ras having a mutation at any one or more of positions 73, 74, 75, 77 or 78, or to Ras including any of the combinations of Ras mutations described above and particularly, any combination of a mutation at position 12 and/or 13 with a mutation at position 59, 61, 73, 74, 75, 76, 77, and/or 78.

Nucleic Acid Molecules and Proteins of the Invention

According to the present invention, a Ras protein or Ras-encoding nucleic acid molecule useful in various aspects of the present invention can include wild-type or mutant Ras proteins, or one or more portions thereof (e.g., domains or portions thereof useful in any research, diagnostic, screening, or therapeutic method), as well as nucleic acid ('sense') molecules encoding such proteins or portions thereof (e.g., domains or portions thereof useful in any research, diagnostic, screening, or therapeutic method) or the hybridizing ('anti-sense') strand of nucleic acids to said domains or proteins. The present invention is particularly directed to mutant Ras proteins and nucleic acid molecules encoding such proteins or fragments thereof, wherein the amino acid sequence of the mutant Ras protein or fragment thereof contains a sequence including position 76, wherein there is a mutation at position 76, and particularly, wherein there is a substitution of a non-glutamate amino acid for the glutamate that naturally exists at this position. According to the present invention, reference to a "non-glutamate" amino acid can refer to the substitution of any of the other 20 amino acids commonly found in proteins, which are well known to those of skill in the art. In particularly preferred embodiments, the non-glutamate amino acid is a glycine (E76G), a lysine E76K), or a glutamine (E76Q), although other substitutions at this position, including any other non-glutamate amino acid, are expressly encompassed by the invention.

A Ras-encoding nucleic acid molecule can include or be derived from all or a portion of a ras gene selected from: K-ras, N-ras or H-ras genes. In one aspect, the Ras-encoding nucleic acid molecule encodes a Ras protein with the single mutation at position 76. In another aspect, the Ras-encoding nucleic acid molecule encodes a Ras protein comprising one or more further mutations in addition to the mutation at position 76, including, but not limited to, mutations at positions 12, 13, 59 and/or 61, the positions being relative to a wild-type K-, H- or N-Ras amino acid sequence. In other embodiments, various other mutants of Ras and nucleic acid molecules encoding such mutants are useful in the present invention (including mutant Ras comprising mutations at position 12, 13, 59 and/or 61 with respect to a wild-type Ras amino acid sequence), and can be combined with a separate E76 protein or peptide mutant of Ras or a separate nucleic acid molecule encoding such mutant. In some embodiments, the Ras-encoding nucleic acid molecule encodes a Ras protein with the single mutation at position 73, 74, 75, 77 or 78. In some embodiments, the Ras-encoding nucleic acid molecule encodes a Ras protein comprising any combination of two or more mutations at positions 12, 13, 59, 61, 73, 74, 75, 76, 77 or 78, with combinations of at least one mutation at position 12 or position 13 with at least one mutation at position 59, 61, 73, 74, 75, 76, 77 or 78 being preferred. Again, all positions are relative to a wild-type K-, H- or N-Ras amino acid sequence.

In another aspect, a Ras protein useful in the invention (which can be encoded by a nucleic acid molecule useful in the invention encoding a Ras protein) includes fragments of at least, but not limited to, between 5 and 17 or between 5 and 50, or more (5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 . . . etc.) contiguous amino acid residues of a Ras protein containing amino acid positions 12, 13, 59, 61, 73, 74, 75, 76, 77 and/or 78 relative to the wild-type Ras amino acid sequence, wherein the amino acid residue at positions 12, 13, 59, 61, 73, 74, 75, 76, 77 and/or 78 is mutated, preferably by substitution with an amino acid other than the amino acid occurring at this position in the wild-type or non-tumorigenic, form of Ras, with respect to the wild-type Ras sequence. Typically, the Ras protein has a maximum length of the full-length wild-type or mutated ras protein, which in the case of SEQ ID NOs:2-13 described herein, ranges from 188 to 189 to 193, although the maximum size Ras protein is not limited to these lengths.

In one embodiment, a preferred fragment of a Ras protein includes between about 5 and 9 amino acids of the natural Ras amino acid sequence (the wild-type sequence, or the sequence that is associated with cellular, non-oncogenic Ras) flanking either side of the mutation at position 12, 13, 59, 61, 73, 74, 75, 76, 77 and/or 78 (e.g., an 11 amino acid fragment of Ras comprising the amino acid at position 76 flanked by five amino acids on either side of position 76, wherein the amino acid position at position 76 is mutated with respect to a wild-type, non-tumorigenic, Ras; or a 17 amino acid fragment of Ras comprising the amino acid at position 76 flanked by eight amino acids on either side of position 76, wherein the amino acid at position 76 is mutated with respect to the wild-type Ras sequence). In one embodiment, a Ras protein useful in the invention includes a fragment of at least 5 contiguous amino acids, or at least 10 contiguous amino acids, or at least 15, or at least 20, or at least 25, or at least 30, or at least 35, or at least 40, or at least 50, or at least 60, or at least 75, or at least 100, or at least 125, or at least 150, or at least 175 contiguous amino acids, and up to the full-length size of the Ras protein, including any intervening size fragment of Ras of at least 5 amino acids, in whole number increments (5, 6, 7, 8, 9, 10, 11, 12, 13, 14, 15, 16, 17, 18, 19, 20, . . . 39, 40, 41, . . . 46, 47, 48 . . . etc.). Several of such fragments of the same or different lengths having the same or different mutations can be combined in a single chimeric protein, in one embodiment. Examples of such proteins are described in the Examples.

Preferably, the fragment of a nucleic acid molecule encoding the mutant Ras protein or peptide is of a size sufficient to serve as a primer or probe for the identification or amplification of a Ras nucleic acid molecule (e.g., a Ras gene or Ras RNA molecule) that has the same mutation or mutations. A fragment of a Ras protein or peptide is preferably of a size sufficient to at least serve as a T cell epitope (in the context of class I or class II MHC) or as an antibody epitope, although in some embodiments, Ras proteins having other functional qualities may be useful, such as a Ras protein that is associated with GTP, Ras protein that can induce cellular signaling related to gene expression, cellular proliferation and/or motility, or Ras protein that can act as a target in an assay, by way of example. Accordingly, the fragment (nucleic acid or protein) comprises enough of the naturally occurring Ras nucleotide or amino acid sequence flanking the site of the particular mutation, respectively, to be useful for these purposes and in any research, diagnostic, screening, or therapeutic composition or method or use described herein.

Reference to positions with regard to wild-type Ras proteins herein are generally made with reference to the position in mammalian wild-type Ras proteins, or at least with regard to the position in human or murine K-Ras, H-Ras or N-Ras. It is noted that the positions referenced above also correspond to any of the sequences for human or murine K-Ras, H-Ras or N-Ras, since human and mouse amino acid sequences are identical in this region of the protein and since K-Ras, H-Ras and N-Ras are identical in this region. For amino acid sequences that might differ in other animal species, one of skill in the art will readily be able to determine the corresponding sequence positions, such as by simple alignment with the human or murine sequences. Such a fragment can be any length, from at least about 5 contiguous amino acid residues of a Ras protein up to the full-length of the Ras protein, in whole number increments (e.g., 5, 6, 7, 8, 9, 10, 11, 12, 13, 14, 15, 16, 17, 18, 19, 20 . . . 45, 46, 47, etc.).

The nucleotide and amino acid sequence for a variety of Ras family members are well known in the art. SEQ ID NO:2 is the nucleic acid sequence encoding human K-ras (also known in GenBank Accession No. NM_033360). SEQ ID NO:2 encodes human K-ras, represented herein as SEQ ID NO:3. SEQ ID NO:4 is the nucleic acid sequence encoding murine K-ras (also known in GenBank Accession No. NM_021284). SEQ ID NO:4 encodes murine K-ras, represented herein as SEQ ID NO:5. SEQ ID NO:6 is the nucleic acid sequence encoding human H-ras (also known in GenBank Accession No. NM_005343). SEQ ID NO:6 encodes human H-ras, represented herein as SEQ ID NO:7. SEQ ID NO:8 is the nucleic acid sequence encoding murine H-ras (also known in GenBank Accession No. NM_008284). SEQ ID NO:8 encodes murine H-ras, represented herein as SEQ ID NO:9. SEQ ID NO:10 is the nucleic acid sequence encoding human N-ras (also known in GenBank Accession No. NM_002524). SEQ ID NO:10 encodes human N-ras, represented herein as SEQ ID NO:11. SEQ ID NO:12 is the nucleic acid sequence encoding murine N-ras (also known in GenBank Accession No. NM_010937). SEQ ID NO:12 encodes human N-ras, represented herein as SEQ ID NO:13. SEQ ID NOs:2-13 are representative of "wild-type" Ras sequences.

As discussed above, Ras is an example of an oncogene in which several mutations are known to occur at particular positions and be associated with the development of one or more types of cancer. The present invention reports the discovery of a new mutation that has not previously been known or described for Ras, as well as a combination of this mutation with a known mutation that synergize to significantly increase the oncogenicity of a tumor bearing such combination of mutations. Therefore, one can construct fusion proteins useful in the present invention (described in more detail below) that comprise, consist essentially or, or consist of peptides containing this mutated residue and also other particular residues that are known to be mutated in certain cancers, wherein each domain contains a different mutation at that site and/or contains a mutation at a different site, in order to cover several or all known mutations at that site or in the protein. For example, with regard to Ras, one may provide two or more immunogenic domains comprising at least 4 amino acids on either side of and including position 76 (but not limited to 4 amino acids, as shorter or longer stretches of flanking amino acids can be included), wherein each domain has a different substitution for the glutamate that normally occurs in the non-mutated Ras protein at position 76. One of the substitutions at this position is preferably a glycine substitution, a lysine substitution or a glutamine substitution. In one example, the protein or peptide comprises fragments of at least 5-9 contiguous amino acid residues of a wild-type Ras protein, and up to the entire Ras protein, in whole number increments, containing amino acid positions 12, 13, 59, 61, 73, 74, 75, 76, 77 and/or 78 relative to the wild-type Ras protein, wherein the amino acid residues at positions 12, 13, 59, 61, 73, 74, 75, 76, 77 and/or 78 are mutated with respect to the wild-type Ras protein. Preferably, the protein or peptide comprises at least a mutation at position 76, and more preferably, the mutation is a substitution of a glycine, lysine or glutamine for the glutamate that normally resides at that position.

In one aspect, a fusion protein construct useful in the present invention consists of at least one peptide that is fused in frame with another mutated tumor antigen, wherein the peptide is selected from the group consisting of: (a) a peptide comprising at least from positions 4-20 or at least from positions 8-16 of SEQ ID NO:3 (or any size peptide in between or larger), wherein the amino acid residue at position 12 with respect to SEQ ID NO:3 is mutated as compared to SEQ ID NO:3; (b) a peptide comprising at least from positions 5-21 or at least from positions 9-17 of SEQ ID NO:3 (or any size peptide in between or larger), wherein the amino acid residue at position 13 with respect to SEQ ID NO:3 is mutated as compared to SEQ ID NO:3; (c) a peptide comprising at least from positions 51-67 or at least from positions 55-63 of SEQ ID NO:3 (or any size peptide in between or larger), wherein the amino acid residue at position 59 with respect to SEQ ID NO:3 is mutated as compared to SEQ ID NO:3; (d) a peptide comprising at least from positions 53-69 or at least from positions 57-65 of SEQ ID NO:3 (or any size peptide in between or larger), wherein the amino acid residue at position 61 with respect to SEQ ID NO:3 is mutated as compared to SEQ ID NO:3; (e) a peptide comprising at least from positions 65-81 or at least from positions 69-77 of SEQ ID NO:3 (or any size peptide in between or larger), wherein the amino acid residue at position 73 with respect to SEQ ID NO:3 is mutated as compared to SEQ ID NO:3; (f) a peptide comprising at least from positions 66-82 or at least from positions 70-78 of SEQ ID NO:3 (or any size peptide in between or larger), wherein the amino acid residue at position 74 with respect to SEQ ID NO:3 is mutated as compared to SEQ ID NO:3; (g) a peptide comprising at least from positions 67-83 or at least from positions 71-79 of SEQ ID NO:3 (or any size peptide in between or larger), wherein the amino acid residue at position 75 with respect to SEQ ID NO:3 is mutated as compared to SEQ ID NO:3; (h) a peptide comprising at least from positions 69-84 or at least from positions 73-81 of SEQ ID NO:3 (or any size peptide in between or larger), wherein the amino acid residue at position 77 with respect to SEQ ID NO:3 is mutated as compared to SEQ ID NO:3; (i) a peptide comprising at least from positions 70-85 or at least from positions 74-82 of SEQ ID NO:3 (or any size peptide in between or larger), wherein the amino acid residue at position 78 with respect to SEQ ID NO:3 is mutated as compared to SEQ ID NO:3; and/or the most preferred embodiment of (j) a peptide comprising at least from positions 68-84 or at least from positions 72-80 of SEQ ID NO:3 (or any size peptide in between or larger), wherein the amino acid residue at position 76 with respect to SEQ ID NO:3 is mutated as compared to SEQ ID NO:3. It is noted that these positions also correspond to any of SEQ ID NOs: 5, 7, 9, 11 or 13, since human and mouse amino acid sequences are identical in this region of the protein and since K-Ras, H-Ras and N-Ras proteins are identical in this region. The fragments are not limited to those mentioned above, which are exemplary, as long as the fragment is at least about 5 amino acids in length, includes the desired mutation, and is useful, or is encoded by a nucleic acid molecule that is useful, in a research, diagnostic, screening, or therapeutic method as described herein.

In one embodiment, a fusion protein construct useful in the present invention comprises the fusion protein represented herein as SEQ ID NO:14. In another embodiment, a fusion protein construct useful in the present invention comprises the fusion protein represented herein as SEQ ID NO:15.

Accordingly, the present invention includes any nucleic acid molecule that encodes, hybridizes to, or is the complement of a nucleic acid molecule that encodes any of the Ras proteins or fragments thereof described herein, and includes nucleic acid molecules encoding any of the fusion proteins described herein. The invention also includes antisense RNA and DNA molecules based on nucleic acid sequences of the invention, ribozymes based on nucleic acid sequences of the invention, RNAi based on the nucleic acid sequences of the invention, and/or aptamers based on the tertiary Ras protein structure of the invention, which may be prepared by any method known in the art. These include techniques for chemically synthesizing polynucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Antisense cDNA constructs that synthesize antisense RNA constitutively or inducibly, depending on the promoter used, can be introduced stably into host cells. Such nucleic acid-based agents can be introduced into host cells or tissues and used to inhibit the expression and/or function of mutated Ras proteins.

Another embodiment of the present invention includes a recombinant nucleic acid molecule comprising a recombinant vector and a nucleic acid sequence derived from a ras gene and/or encoding a Ras protein or peptide or fragment thereof as described herein. Typically, a recombinant nucleic acid molecule includes at least one nucleic acid molecule of the present invention operatively linked to one or more expression control sequences. Various types of recombinant vectors which can be used in the invention have been described above.

One or more recombinant molecules of the present invention can be used to produce an encoded product (e.g., a mutated Ras protein or portion thereof). In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

In one embodiment of the invention, a preferred host cell is a yeast cell. Nucleic acid molecules transformed into yeast vehicles of the present invention can include nucleic acid sequences encoding one or more proteins, and/or on or more portions thereof. Such nucleic acid molecules can comprise partial or entire coding regions, regulatory regions, or combinations thereof. One advantage of yeast strains is their ability to carry a number of nucleic acid molecules and of being capable of producing a number of heterologous proteins. A preferred number of antigens to be produced by a yeast vehicle of the present invention is any number of antigens that can be reasonably produced by a yeast vehicle, and typically ranges from at least one to at least about 5 or more, with from about 2 to about 5 compounds being more preferred. Preferred yeast hosts are discussed in detail below.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Kozak sequences, Shine-Dalgarno sequences), modification of nucleic acid molecules to correspond to the codon usage of the host cell, and deletion of sequences that destabilize transcripts.

Fusion Proteins

As discussed above, one may construct fusion proteins for use in various embodiments of the invention, including fusion proteins that contain at least one Ras peptide or protein containing the mutated residue at position 76 (or the mutated residue at position 73, 74, 75, 77 or 78 or any of the combinations described herein) (as noted above, position 76 is denoted with respect to the wild-type mammalian, and particularly human or murine, Ras amino acid sequence), and that may also include other Ras peptides or proteins containing mutations at other residues that are known to be mutated in certain cancers. Other antigens than Ras, or portions thereof, including other cancer antigens and including various mutants of other proteins associated with cancer, may also be included in such fusions. Also encompassed by the invention are nucleic acid molecules encoding such fusion proteins.

In one aspect, the Ras-based proteins and peptides of the invention, including the combinations of different Ras proteins and peptides and/or other proteins and peptides discussed above can be included in a fusion protein that has been designed to stabilize the expression of the heterologous protein in a yeast vehicle and/or prevent posttranslational modification of the expressed heterologous protein. Such fusion proteins are generally described in PCT Publication No. WO 2004/058157 A2, which is incorporated herein by reference in its entirety. These fusion proteins are most typically expressed as recombinant proteins by a yeast vehicle (e.g., by an intact yeast or yeast spheroplast, which can optionally be further processed to a yeast cytoplast, yeast ghost, or yeast membrane extract or fraction thereof, described below), although it is an embodiment of the invention that one or more such fusion proteins could be loaded into a yeast vehicle or otherwise complexed or mixed with a yeast vehicle as described below to form a vaccine or composition useful in the present invention.

One such fusion protein useful in the present invention is a fusion protein that includes: (a) at least one Ras antigen (including a peptide or protein) including the mutation at position 76 as described herein; and (b) a synthetic peptide. In one embodiment, a fusion protein useful in the present invention comprises the fusion protein represented herein by SEQ ID NO:14. In another embodiment, a fusion protein useful in the present invention comprises the fusion protein represented herein by SEQ ID NO:15.

In one embodiment, the synthetic peptide is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but is more preferably at least 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-$X_2$-$X_3$-$X_4$-$X_5$-$X_6$, wherein M is methionine; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine, lysine or arginine. In one embodiment, the $X_6$ residue is a proline. An exemplary synthetic sequence that enhances the stability of expression of an antigen in a yeast cell and/or prevents post-translational modification of the protein in the yeast includes the sequence M-A-D-E-A-P (SEQ ID NO:1). The MADEAP sequence can be used with other antigens in addition to the antigen. In addition to the enhanced stability of the expression product, this fusion partner does not appear to negatively impact the immune response against the vaccinating antigen in the construct. In addition, the synthetic fusion peptides can be designed to provide an epitope that can be recognized by a selection agent, such as an antibody.

In another embodiment of the invention, the nucleic acids that encode the translation start site of a synthetic peptide used in the invention are A-C-C-A-T-G-G, in accordance with Kozak translation sequence rules, where the ATG in this sequence is the initial translation start site and encodes the methionine of M-A-D-E-A-P (SEQ ID NO:1). It is to be understood that various embodiments of the invention as described herein may also be combined. For example, in one aspect of the invention, when the synthetic peptide is MA-D-E-A-P (SEQ ID NO:1), the nucleic acids encoding the start site for this peptide can be A-C-C-A-T-G-G. Various other combinations of embodiments of the invention will be apparent to those of skill in the art.

In one aspect of the invention, the yeast vehicle is manipulated such that the antigen is expressed or provided by delivery or translocation of an expressed antigen product, partially or wholly, on the surface of the yeast vehicle (extracellular expression). One method for accomplishing this aspect of the invention is to use a spacer arm for positioning one or more antigen(s) on the surface of the yeast vehicle. One way to use a spacer arm is to create a fusion protein of the antigen(s) of interest with a protein that targets the antigen(s) to the yeast cell wall. For example, one protein that can be used is a yeast protein (e.g., cell wall protein 2 (cwp2), Aga2, Pir4 or Flo1 protein) that enables the antigen(s) to be targeted to the yeast cell wall such that the antigen is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s).

Another method for positioning the target antigen(s) to be exposed on the yeast surface is to use signal sequences such as glycosylphosphatidyl inositol (GPI) to anchor the target to the yeast cell wall. Alternatively, positioning can be accomplished by appending signal sequences that target the antigen(s) of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length.

In another embodiment, the yeast protein stabilizes the expression of the fusion protein in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

In another aspect of the invention, other sequences can be used to target, retain and/or stabilize the protein to other parts of the yeast vehicle, for example, in the cytosol or the mitochondria. Examples of suitable yeast protein that can be used for any of the embodiments above include, but are not limited to, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Antibodies and Antigen-Binding Peptides

One embodiment of the invention relates to an antibody or antigen binding peptide that selectively binds to a Ras protein or peptide having the E76 mutation described herein, including, but not limited to, an E76G mutation, an E76K mutation and/or an E76Q mutation. Other embodiments of the invention relate to an antibody or antigen binding peptide that selectively binds to a Ras protein having a mutation at any one or more of positions 73, 74, 75, 77 or 78, or to Ras including any of the combinations of Ras mutations described above and particularly, any combination of a mutation at position 12 and/or 13 with a mutation at position 59, 61, 73, 74, 75, 76, 77, and/or 78. Antibodies are characterized in that they comprise immunoglobulin domains and as such, they are members of the immunoglobulin superfamily of proteins. An antibody of the invention includes polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$^2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the VH and/or VL domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (Nature 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The invention also extends to non-antibody polypeptides, sometimes referred to as binding partners, that have been designed to bind specifically to, and either activate or inhibit as appropriate, a mutated Ras protein of the invention. Examples of the design of such polypeptides, which possess a prescribed ligand specificity are given in Beste et al. (Proc. Natl. Acad. Sci. 96:1898-1903, 1999), incorporated herein by reference in its entirety.

Small Molecules, Conformational Antagonists, and Other Compounds

The invention also includes small molecule compounds (e.g., products of drug discovery using the mutated Ras discovered by the inventors) such as conformational antagonists or activators of GTP hydrolysis. In one embodiment, such compounds may be mimics or modified forms of Ras-GAP that are capable of interacting with mutated Ras proteins to trigger GTP hydrolysis. In another embodiment, such compounds may interact directly with Ras-GAP to adapt the endogenous Ras-GAP protein to trigger GTP hydrolysis in Ras mutants, such as those described herein. Preferably, such compounds do not trigger GTP hydrolysis of wild-type (non-mutated, or non-tumorigenic) Ras, so that the compounds are more useful as tumor-specific compounds.

Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety. Candidate compounds initially identified by drug design methods can be screened for the ability to modulate GTP hydrolysis or serve as a conformational antagonist of a mutant Ras protein described herein.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Compositions and Vaccines

As discussed above, one embodiment of the invention relates to compositions or vaccines that include the mutated Ras proteins, nucleic acid molecules encoding the same, or any of the therapeutic nucleic acids (e.g., aptamers, ribozymes, RNAi) or peptides or small molecules (e.g., conformational antagonists, activators of GTP hydrolysis) as discussed above. The present invention includes an embodiment where the mutated Ras proteins described herein can be used in a "conventional" composition or vaccine or in conjunction with a yeast-based vaccine (described below U.S. Pat. Nos. 5,830,463 and 7,083,787, as well as U.S. Patent Publication Nos. 2004-0156858 A1 and 2006-0110755 A1). Either type of composition or vaccine can include, in addition to any of the mutated Ras proteins described herein (e.g., a Ras protein or peptide having a mutation at position 76, and preferably, an E76G, E76K or E76Q mutation, or a combination of the Ras E76 mutation with another mutation, such as a G12 mutation), a pharmaceutically acceptable carrier. As used herein, a pharmaceutically acceptable carrier refers to any substance or vehicle suitable for delivering a mutated Ras protein useful in a method of the present invention to a suitable in vivo or ex vivo site. Such a carrier can include, but is not limited to, an adjuvant, an excipient, or any other type of delivery vehicle or carrier.

According to the present invention, adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

Therapeutic compositions, including vaccines, of the present invention can also contain one or more pharmaceutically acceptable excipients. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a composition (or in some embodiments, a yeast vehicle or dendritic cell comprising the yeast vehicle) in a form that, upon arrival of the composition at a target cell, tissue, or site in the body, the composition is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to, water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

One component of a therapeutic composition or vaccine of the present invention includes at least one antigen for vaccinating an animal, and particularly, at least one antigen comprising at least a portion of a Ras protein containing the mutation at position 76 as described herein. The composition or vaccine can include, one, two, a few, several or a plurality of antigens, including one or more immunogenic domains of one or more antigens, as desired. According to the present invention, an antigen suitable for use in the present composition or vaccine can include two or more immunogenic domains or epitopes from the same antigen, two or more antigens immunogenic domains, or epitopes from the same cell, tissue or organism, or two or more different antigens, immunogenic domains, or epitopes from different cells, tissues or organisms. Preferably, the antigen is heterologous to the yeast strain (i.e., is not protein that is naturally produced by the yeast strain in the absence of genetic or biological manipulation). Preferred mutated Ras proteins and preferred fusion proteins for use in a conventional vaccine or composition or with a yeast vehicle of the present invention have been described above.

In one embodiment of the present invention, a composition or vaccine can also include biological response modifier compounds, or the ability to produce such modifiers (i.e., by transfection with nucleic acid molecules encoding such modifiers), although such modifiers are not necessary to achieve a robust immune response when a yeast vehicle is used (discussed below). Biological response modifiers are compounds that can modulate immune responses. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cellular compared to humoral immunity, or vice versa.). There are a number of techniques known to those skilled in the art to measure stimulation or suppression of immune responses, as well as to differentiate cellular immune responses from humoral immune responses.

Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), transforming growth factor beta (TGF-β) steroids, prostaglandins and leukotrienes. Other suitable biological response modifiers include, but are not limited to, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®), anti-CD4, anti-CD25, anti-PD-1, anti-PD-L1, anti-PD-L2 or agents that block FOXP3 (e.g., to abrogate the activity/kill CD4+/CD25+ T regulatory cells); Flt3 ligand, imiquimod (Aldara™), GM-CSF, sargramostim (Leukine®), Toll-like receptor (TLR)-7 agonists, or TLR-9 agonists (e.g., agents that increase the number of, or increase the activation state, of dendritic cells, macrophages and other professional antigen-presenting cells). Such biological response modifiers are well known in the art and are publicly available.

Yeast-Based Vaccines or Compositions

One aspect of the invention relates to a composition or yeast-based vaccine comprising: (a) a yeast vehicle; and (b) an antigen comprising at least one of the mutated Ras proteins or peptides described herein (e.g., the Ras protein having a mutation at position 76, or a protein or combination of proteins including the E76 mutation and another Ras mutation, such as a G12 mutation), or multiple epitopes or antigens or a fusion protein described herein, expressed by the yeast vehicle. As discussed above, in addition to the E76 mutation, mutations at any one or more of positions 73, 74, 75, 77 or 78, or any of the combinations of Ras mutations described above and particularly, any combination of a mutation at position 12 and/or 13 with a mutation at position 59, 61, 73, 74, 75, 76, 77, and/or 78, are encompassed by the invention.

According to the present invention, a yeast vehicle is any yeast cell (e.g., a whole or intact cell) or a derivative thereof (see below) that can be used in conjunction with an antigen in a vaccine or therapeutic composition of the invention, or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a yeast cell wall preparation, or a subcellular yeast membrane extract or fraction thereof (also referred to as a yeast membrane particle, and previously as a subcellular yeast particle).

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen was expressed recombinantly by the yeast prior to preparation of the yeast membrane particles, the antigen of interest. Antigens can be carried inside the membrane, on either surface of the membrane, or combinations thereof (i.e., the antigen can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired (e.g., protective) immune response against the infectious agent.

Any yeast strain can be used to produce a yeast vehicle of the present invention. Yeast are unicellular microorganisms that belong to one of three classes: Ascomycetes, Basidiomycetes and Fungi Imperfecti. One major consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain is done to minimize any adverse effects to the individual to whom the yeast vehicle is administered. However, pathogenic yeast may be used if the pathogenicity of the yeast can be negated by any means known to one of skill in the art (e.g., mutant strains). While pathogenic yeast strains, or nonpathogenic mutants thereof, have been used in the past as adjuvants or as biological response modifiers, and can be used in accordance with the present invention, nonpathogenic yeast strains are preferred.

Preferred genera of yeast strains include *Saccharomyces, Candida* (which can be pathogenic), *Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe*. *S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) to be expressed at high levels. In addition, any mutant yeast strains can be used in the present invention, including those that exhibit reduced post-translational modifications of expressed target antigens, such as mutations in the enzymes that extend N-linked glycosylation.

In one embodiment, a preferred yeast vehicle of the present invention is capable of fusing with the cell type to which the yeast vehicle and antigen is being delivered, such as a dendritic cell or macrophage, thereby effecting particularly efficient delivery of the yeast vehicle, and in many embodiments, the antigen, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. It has been previously shown that yeast vehicles of the present invention are readily taken up by dendritic cells (as well as other cells, such as macrophages).

According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

In one aspect, a yeast cell or yeast spheroplast used to prepare the yeast vehicle is transfected with a recombinant nucleic acid molecule encoding the antigen(s) such that the antigen is recombinantly expressed by the yeast cell or yeast spheroplast. In this aspect, the yeast cell or yeast spheroplast that recombinantly expresses the antigen(s) is used to produce a yeast vehicle comprising a yeast cytoplast, a yeast ghost, or a yeast membrane particle or yeast cell wall particle, or fraction thereof.

In general, the yeast vehicle and antigen(s) can be associated by any technique described herein. In one aspect, the yeast vehicle was loaded intracellularly with the antigen(s). In another aspect, the antigen(s) was covalently or non-covalently attached to the yeast vehicle. In yet another aspect, the yeast vehicle and the antigen(s) were associated by mixing. In another aspect, and in the preferred embodiment, the antigen(s) is expressed recombinantly by the yeast vehicle or by the yeast cell or yeast spheroplast from which the yeast vehicle was derived.

Expression of an antigen in a yeast vehicle of the present invention is accomplished using techniques known to those skilled in the art. Briefly, a nucleic acid molecule encoding at least one desired antigen is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Preferred promoters for expression in Saccharomyces cerevisiae include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL 10), cytochrome $c_1$ (CYC1), Sec7 protein (SEC7) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), as well as the CUP1 promoter and the TEF2 promoter, being even more preferred. Likewise, a number of upstream activation sequences (UASs), also referred to as enhancers, are known. Preferred upstream activation sequences for expression in Saccharomyces cerevisiae include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in Saccharomyces cerevisiae include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Optimization concerns and methods for extracellular expression of antigens by yeast have been discussed in detail previously herein.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In some aspects of the invention, and particularly when it is desired to have sufficient surface expression or provision of an antigen in embodiments where induction of a humoral immune response is desired, the yeast are grown in a media maintained at a neutral pH. As used herein, the general use of the term "neutral pH" refers to a pH range between about pH 5.5 and about pH 8, preferably between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. Preferably, yeast are grown in a media maintained at a pH level of at least 5.5, namely the pH of the culture media is not allowed to drop below pH 5.5. The use of a neutral pH in culturing yeast promotes several biological effects that are desirable characteristics for using the yeast as vehicles for immunomodulation.

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen. Subsequently, the yeast vehicle, which now contains the antigen intracellularly, can be administered to the patient or loaded into a carrier such as a dendritic cell (described below). As used herein, a peptide comprises an amino acid sequence of less than or equal to about 30-50 amino acids, while a protein comprises an amino acid sequence of more than about 30-50 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism, by the loading of a mammalian tumor cell, or portions thereof, for example.

In another embodiment of the present invention, an antigen is physically attached to the yeast vehicle. Physical attachment of the antigen to the yeast vehicle can be accomplished by any method suitable in the art, including covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen are associated with each other by a more passive, non-specific or non-covalent binding mechanism, such as by gently mixing the yeast vehicle and the antigen together in a buffer or other suitable formulation (e.g., admixture).

In one embodiment of the invention, the yeast vehicle and the antigen are both loaded intracellularly into a carrier such as a dendritic cell or macrophage to form the therapeutic composition or vaccine of the present invention. Alternatively, an antigen of the invention (i.e., a Ras fusion protein of the invention) can be loaded into a dendritic cell in the absence of the yeast vehicle.

Various forms in which the loading of both components can be accomplished are discussed in detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by a dendritic cell.

In one embodiment, intact yeast (with or without expression of heterologous antigens) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune response. For example, enzymatic treatment, chemical treatment or physical force (e.g., mechanical shearing or sonication) can be used to break up the yeast into parts that are used as an adjuvant.

Therapeutic Methods of the Invention

One embodiment of the invention relates to the use of any of the agents described herein related to the mutated Ras of the invention (e.g., a Ras having at least a mutation at codon 76, or the combination of the codon 76 mutation with another Ras mutation such as a codon 12 mutation) in the preparation of a medicament or composition or vaccine to protect an animal against a cancer. As discussed above, in addition to the E76 mutation, mutations at any one or more of positions 73, 74, 75, 77 or 78, or any of the combinations of Ras mutations described above and particularly, any combination of a mutation at position 12 and/or 13 with a mutation at position 59, 61, 73, 74, 75, 76, 77, and/or 78, are encompassed by the invention. Other embodiments of the invention relate to a method to protect an animal against a cancer, comprising administering to an animal that has or is at risk of developing a cancer, a vaccine or therapeutic composition described herein to reduce or prevent at least one symptom of the cancer in the animal.

In one aspect, the vaccine or compositions comprise any of the vaccines or compositions described above that contain at least the antigen comprising at least a mutated Ras protein or peptide comprising the mutation at position 76 or an antigen or antigen(s) including a combination of the position 76 mutation with another Ras mutation, such as a position 12 mutation, and more preferably, that comprise the various peptides, proteins, chimeric constructs and/or fusion proteins described above. Other Ras mutations and combinations thereof that can be used in a vaccine or composition are described above. Other therapeutic compositions useful in this method of the invention include a composition comprising a compound or agent that targets the mutated Ras proteins identified by the inventors and inhibits the expression of such proteins by tumors, or initiates or upregulates GTP hydrolysis of Ras proteins to override or compensate for the effect of mutated Ras proteins on GTP hydrolysis. Such compounds or agents can include, but are not limited to, various inhibitory nucleic acids, such as ribozymes, RNAi, or aptamers, and/or various peptide and synthetic or small molecule compounds (e.g., products of drug discovery using the mutated Ras discovered by the inventors) such as conformational antagonists or activators of GTP hydrolysis. Such compounds or agents and methods to identify the same are discussed elsewhere herein. In one aspect of the invention, full-length mutated Ras products (e.g., nucleic acid molecules and proteins) are not administered to an individual in connection with therapeutic methods and uses of the invention; rather, peptides and fragments of such Ras products, or other tools associated with such Ras products (e.g., aptamers, RNAi, etc.) are selected. In the context of a composition for the elicitation of an immune response, particularly in the context of expression by a yeast vehicle of the invention, full-length Ras may be used, although immunogenic portions and multi-domain fusion proteins are preferred.

The vaccine or composition also comprises a pharmaceutically acceptable carrier or excipient and in one embodiment (e.g., wherein the composition is a vaccine), includes the yeast vehicle described herein. In one aspect, fusion proteins included in the vaccine comprise at least two or more cancer antigens. In another aspect, such a fusion protein comprises at least one or more immunogenic domains of one or more cancer antigens.

In another aspect, the cancer antigen is an antigen associated with a cancer including, but not limited to, melanomas, squamous cell carcinoma, breast cancers, head and neck carcinomas, thyroid carcinomas, soft tissue sarcomas, bone sarcomas, testicular cancers, prostatic cancers, pancreatic cancers, ovarian cancers, bladder cancers, skin cancers, brain cancers, angiosarcomas, hemangiosarcomas, mast cell tumors, primary hepatic cancers, lung cancers (including non-small cell lung carcinomas), pancreatic cancers, gastrointestinal cancers (including colorectal cancers), renal cell carcinomas, hematopoietic neoplasias and metastatic cancers thereof.

In all aspects, at least one antigen comprising, consisting essentially of or consisting of a peptide of Ras comprising the mutation at position 76, a combination of the position 76 mutation with at least one additional Ras mutation, such as a position 12 mutation, a Ras comprising a mutation at position 73, 74, 75, 77 or 78, a Ras comprising any of the combinations of mutations described herein, or a nucleic acid agent or other agent making use of such mutations, as described above, is included in the vaccine or composition.

The present invention includes the delivery of a composition or vaccine of the invention to an animal. The administration process can be performed ex vivo or in vivo. Ex vivo administration refers to performing part of the regulatory step outside of the patient, such as administering a composition of the present invention to a population of cells (dendritic cells) removed from a patient under conditions such that a yeast vehicle and antigen are loaded into the cell, and returning the cells to the patient. The therapeutic composition of the present invention can be returned to a patient, or administered to a patient, by any suitable mode of administration.

Administration of a vaccine or composition can be systemic, mucosal and/or proximal to the location of the target site (e.g., near a tumor). The preferred routes of administration will be apparent to those of skill in the art, depending on the type of condition to be prevented or treated, the antigen used, and/or the target cell population or tissue. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189:11277-11281, 1992, which is incorporated herein by reference in its entirety). For example, in one embodiment, a composition or vaccine of the invention can be formulated into a composition suitable for nebulized delivery using a suitable inhalation device or nebulizer. Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products. Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes.

According to the present invention, an effective administration protocol (i.e., administering a vaccine or therapeutic composition in an effective manner) comprises suitable dose parameters and modes of administration that result in elicitation of an immune response in an animal that has a disease or condition or that is at risk of contracting a disease or condition, in the case of administration of a vaccine (therapeutic or prophylactic), preferably so that the animal is protected from the disease. When the composition comprises a different therapeutic compound or agent as described herein, an effective administration protocol comprises suitable dose parameters and modes of administration that result in the alleviation or detectable improvement in at least one symptom or indicator of the disease or condition in the patient, such as a reduction in tumor size or levels, or prevention of disease when the patient is at risk of contracting the disease or condition. Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that is capable of eliciting an antigen-specific immune response or eliciting an improvement in at least one symptom or indicator of disease, in an animal when administered one or more times over a suitable time period. Doses can vary depending upon the disease or condition being treated. For example, in one embodiment, when an antigen is delivered with a yeast vehicle, a single dose of a yeast vehicle of the present invention is from about $1\times10^5$ to about $5\times10^7$ yeast cell equivalents per kilogram body weight of the organism being administered the composition. In a preferred embodiment, the yeast cells per dose are not adjusted for weight of the organism. In this embodiment, a single dose of a yeast vehicle of the present invention is from about $1\times10^4$ to about $1\times10^9$ yeast cells per dose. More preferably, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). This range of doses can be effectively used in any organism of any size, including mice, monkeys, humans, etc. When the vaccine is administered by loading the yeast vehicle and antigen into dendritic cells, a preferred single dose of a vaccine of the present invention is from about $0.5\times10^6$ to about $40\times10^6$ dendritic cells per individual per administration. Preferably, a single dose is from about $1\times10^6$ to about $20\times10^6$ dendritic cells per individual, and more preferably from about $1\times10^6$ to about $10\times10^6$ dendritic cells per individual.

A preferred single dose of a nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 μm in diameter) and are propelled into skin cells or muscle with a "gene gun."

An appropriate single dose of a nucleic acid:liposome complex is from about 0.1 μg to about 100 μg per kg body weight of the patient to which the complex is being administered. In another embodiment, an appropriate single dose is from about 1 μg to about 10 μg per kg body weight. In another embodiment, an appropriate single dose of nucleic acid:lipid complex is at least about 0.1 μg of nucleic acid, more preferably at least about 1 μg of nucleic acid, even more preferably at least about 10 μg of nucleic acid, even more preferably at least about 50 μg of nucleic acid, and even more preferably at least about 100 μg of nucleic acid.

When the composition comprises a protein, small molecule (i.e., the products of drug design) or antibody, a preferred single dose of such a compound typically comprises between about 0.01 microgram×kilogram$^{-1}$ and about 10 milligram×kilogram$^{-1}$ body weight of an animal. A more preferred single dose of such an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. Another particularly preferred single dose of an agent comprises between about 0.1 microgram×kilogram$^{-1}$ and about 10 microgram×kilogram$^{-1}$ body weight of an animal, if the agent is delivered parenterally.

"Boosters" of a therapeutic composition that is a vaccine are preferably administered when the immune response against the antigen has waned or as needed to provide an immune response or induce a memory response against a particular antigen or antigen(s). Boosters can be administered from about 2 weeks to several years after the original administration. In one embodiment, an administration schedule is one in which from about $1\times10^5$ to about $5\times10^7$ yeast cell equivalents of a composition per kg body weight of the organism is administered from about one to about 4 times over a time period of from about 1 month to about 6 months. Additional dosing of other therapeutic compositions described herein can be determined by the clinician based on the reevaluation of the patient after administration and assessment of the status of the disease or condition or symptoms or indicators thereof.

In one embodiment of the invention, a patient identified as having a Ras mutation as described herein is administered, separately or in conjunction with another therapy described herein, gene therapy to deliver wild-type or "healthy" (non-mutated) Ras to the patient. Methods of administering a nucleic acid molecule in a gene therapy protocol are known in the art.

Methods and uses directed to therapeutic compositions and vaccines of the invention are primarily intended for use in the prevention and/or treatment of a disease or condition. The term "protecting" can be generically used to convey prevention and/or treatment. A therapeutic composition or vaccine of the present invention, when administered to an individual, can: prevent a disease from occurring; cure the disease; delay the onset of the disease; and/or alleviate (reduce, delay, diminish) disease symptoms, signs or causes (e.g., reduce one or more symptoms of the disease; reduce the occurrence of the disease; increase survival of the individual that has or develops the disease; and/or reduce the severity of the disease). As such, the invention includes both preventing disease occurrence (prophylactic treatment or prophylactic vaccine) and treating an animal that has a disease or that is experiencing symptoms of a disease (therapeutic treatment or a therapeutic vaccine). In one embodiment, the methods of the invention are effective to elicit an immune response in the individual by inducing a beneficial or protective immune response that may, in some instances, additionally suppress (e.g., reduce, inhibit or block) an overactive or harmful immune response. In another aspect, the methods of the invention are effective to result in at least one detectable improvement or benefit in at least one symptom or indicator of the disease or condition, which for cancer, can include, but is not limited to, reduction in tumor burden, e.g., reduction in tumor size, reduction in tumor levels, reduction in tumor growth rate, and/or reduction in metastases and/or delay of the onset of the disease, and/or increased survival of the patient.

Diagnostic and Prognostic Methods of the Invention

Another embodiment of the invention relates to the use of the mutated Ras proteins or ras nucleic acid molecules of the invention, and portions thereof, as a biomarker in a diagnostic or prognostic assay or kit for cancer. In a preferred embodiment, the invention relates to the detection of nucleic acids (genes or RNA) encoding the mutated Ras proteins in a diagnostic or prognostic assay for cancer. In one embodiment, the method includes determining the presence and/or level of the E76 mutant marker (also referred to herein generically as a biomarker) in a nucleic acid or protein sample. The E76 mutation can include any mutation at E76 as described herein, and preferably includes the E76G mutation, the E76K mutation, or the E76Q mutation, although it is to be understood that other tumors may have different mutations at this position of Ras as compared to the wild-type protein or gene. The biomarker can be detected by detecting the mutated Ras protein, but is more preferably detected by detecting a nucleic acid molecule encoding such mutated Ras protein (RNA or DNA). In another embodiment, the method includes additionally detecting (concurrently or sequentially) the presence and/or level of another mutant biomarker for Ras, including the previously known mutations at positions (codons) 12, 13, 59 or 61 of Ras. In one embodiment, the method includes detecting the presence and/or level of both an E76 mutation and a G12 mutation in a single patient sample (nucleic acid or protein). In another embodiment, the method can include determining the presence and/or level of any one or more of positions 73, 74, 75, 77 or 78, or any of the combinations of Ras mutations described above and particularly, any combination of a mutation at position 12 and/or 13 with a mutation at position 59, 61, 73, 74, 75, 76, 77, and/or 78. Aspects below will be described with respect to the E76 mutation for the sake of simplicity, but are to be extended to encompass any of these mutations or combinations thereof.

The first step of this method of the present invention includes detecting the presence of the mutated ras gene (comprising the mutation resulting in the E76 Ras mutation) and/or the expression or biological activity of the E76 Ras in a test sample from a patient (also called a patient sample). Suitable methods of obtaining a patient sample are known to a person of skill in the art. A patient sample can include any bodily fluid or tissue from a patient that may contain tumor cells or proteins of tumor cells. More specifically, according to the present invention, the term "test sample" or "patient sample" can be used generally to refer to a sample of any type which contains cells or products that have been secreted from or is contained within cells to be evaluated by the present method, including but not limited to, a sample of isolated cells, a tissue sample, a bodily fluid sample, or, for example, a sample of nucleic acids obtained from a cell sample isolated from the patient.

According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch.

A bodily fluid sample, like the tissue sample, contains the cells to be evaluated for marker expression or biological activity and/or may contain a soluble biomarker that is secreted by cells, and is a fluid obtained by any method suitable for the particular bodily fluid to be sampled. Bodily fluids suitable for sampling include, but are not limited to, blood, mucous, seminal fluid, saliva, breast milk, bile and urine.

In general, the sample type (i.e., cell, tissue or bodily fluid) is selected based on the accessibility and structure of the organ or tissue to be evaluated for tumor cell presence or growth and/or on what type of cancer is to be evaluated. For example, if the organ/tissue to be evaluated is the breast, the sample can be a sample of epithelial cells from a biopsy (i.e., a cell sample) or a breast tissue sample from a biopsy (a tissue sample). The sample that is most useful in the present invention will be cells, tissues or bodily fluids (and components thereof, such as DNA) isolated from a patient by a biopsy or surgery or routine laboratory fluid collection.

Once a sample is obtained from the patient, the sample is evaluated to detect the presence of the mutated ras gene, or to detect the expression or biological activity of the E76 Ras, alone or in combination with other mutations, such as other Ras or ras mutations, and particularly, a G12 mutation (e.g., by detection of mRNA encoding the mutated gene product or by detection of mutated Ras protein) of the present invention in the cells of the sample.

For example, the presence and/or level of the ras biomarker can be determined by conventional methods such as gene or RNA detection methods (e.g., DNA sequencing, oligonucleotide hybridization, PCR amplification with primers specific to the mutation), or protein detection methods (e.g., immunoassays or biochemical assays to determine the level of the gene product). In general, the nucleic acid sequence of the ras gene or RNA in a patient sample can be detected by any suitable method or technique of measuring or detecting gene sequence or expression. Such methods include, but are not limited to, PCR, reverse transcriptase-PCR (RT-PCR), in situ PCR, in situ hybridization, Southern blot, Northern blot, sequence analysis, microarray analysis, detection of a reporter gene, or other DNA/RNA hybridization platforms. Expression can be evaluated simply for the presence of the mutated ras sequence(s) and/or compared to samples isolated from healthy individuals or another negative control.

For example, a patient tumor biopsy sample from an embedded paraffin block may be sectioned and stained with hematoxylin, after which the pathological cells from the sample may be isolated by laser capture microdissection. The genomic DNA from the isolated cells is then used as a template for a PCR reaction to amplify the DNA fragment harboring the specified ras sequence in exon 3 using primers that flank the sequence of interest. Alternatively, the sections from the tumor biopsy may be analyzed by in situ PCR, such that amplification is dependent on hybridization with primers that bind to the mutated sequence, and elongated with labeled nucleotides, such that an amplified sequence is specifically detected within the tumor cells. As yet another alternative, the sections may be probed with oligonucleotides that hybridize specifically with one or more E76 mutations, but not with wild-type ras sequences.

When the Ras E76 mutant protein (or combination Ras mutations as described herein) is detected, protein expression can be detected in suitable tissues, such as tumor tissue and cell material obtained by biopsy. For example, the patient tumor biopsy sample, which can be immobilized, can be contacted with an antibody, an antibody fragment, or an aptamer, that selectively binds to the Ras protein to be detected and determining whether the antibody, fragment thereof or aptamer has bound to the Ras protein. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry. In a particular immunoassay, binding to the Ras protein is determined using a first monoclonal antibody that binds specifically to the mutated Ras protein and a second antibody that binds to the first antibody.

In the diagnostic/prognostic methods of the invention, if the E76 Ras or ras mutation (or combination of Ras or ras mutations described herein) is detected (either by detection of the nucleic acid or the protein), such detection of the mutation is considered to be indicative of the presence of tumor cells or the predisposition to develop tumor cells in the patient, as this mutation is not expected to be present in "healthy" individuals (i.e., individuals who do not have and do not appear to be predisposed to cancer caused by or contributed to by this Ras mutation). If desired, however, one can compare the detection of the Ras or ras mutation to the "Ras status" (i.e., the sequence of Ras proteins or genes) in a healthy or normal individual, if desired.

While detection of the E76 mutation is sufficient to conclude a positive diagnosis of the presence of tumor cells or the predisposition to develop tumor cells in the patient, the detection of the combination of E76 with another Ras or ras mutation, and particularly, a G12 mutation, in the tumor sample, is believed to be indicative not only of the presence of tumor cells or the predisposition to develop tumor cells, but additionally of a tumor that is predicted to be more aggressive (e.g., display faster or higher volume tumor growth, increased invasiveness, increased propensity for metastatic growth, increased prognosis for a poor outcome), as compared to detection of only the E76 mutation, detection of only the other Ras mutation (e.g., a G12 mutation), and/or detection of no mutation.

According to the present invention, a "baseline level" is a control level, and in some embodiments (but not all embodiments, depending on the method), a normal level, of biomarker (e.g., Ras or ras) expression or activity against which a test level of biomarker expression or biological activity (i.e., in the test sample) can be compared. The term "negative control" used in reference to a baseline level of biomarker expression or biological activity typically refers to a baseline level established in a sample from the patient or from a population of individuals that is believed to be normal (i.e., non-tumorous, non-cancerous, not undergoing neoplastic transformation, not exhibiting the presence of tumor cells or inappropriate cell growth). In one embodiment, a baseline level or control can be established from uninvolved tissue from the patient being tested (i.e., tissue that is believed to be unaffected by cancer), so that the tumor status (tumor burden, growth, volume, etc.) of a patient can be monitored over time and/or so that the efficacy of a given therapeutic protocol can be evaluated over time. Methods for detecting Ras biomarker expression or biological activity are described in detail above. A "positive control" can include any control that confirms the positive detection of the biomarker, such as a level of biomarker expression or activity established in a confirmed tumor, or any other positive indicator of the parameter being evaluated with respect to the biomarker.

When a baseline or control is used, it will be appreciated by those of skill in the art that a baseline or control need not be established for each assay as the assay is performed but rather, a baseline or control can be established by referring to a form of stored information regarding a previously determined baseline level of biomarker expression for a given control sample, such as a baseline level established by any of the above-described methods. Such a form of stored information can include, for example, but is not limited to, a reference chart, listing or electronic file of population or individual data regarding "healthy" (negative control) or tumor positive (including staged tumors) biomarker expression; a medical chart for the patient recording data from previous evaluations; or any other source of data regarding baseline biomarker expression that is useful for the patient to be diagnosed.

After the presence or absence of the mutated Ras proteins or gene or RNA encoding the same is detected in the sample to be evaluated for tumor cells, the final step of making a diagnosis, monitoring, or staging of the patient can be performed, and a treatment or prevention protocol or further screening protocol can be prescribed. Additionally, if the presence of the Ras mutation is detected, the patient can be evaluated by additional cancer diagnostic methods to confirm the initial diagnosis.

In one embodiment of the invention, the diagnostic method can be used to determine a diagnosis for a patient, a prognosis for a patient, and also to determine the appropriate therapy protocol and predict the patient's success or outcome with a given cancer protocol. For example, if a patient is suspected of having a cancer or being at risk of developing a cancer, the method can be used to determine whether or not the patient has a Ras mutation that is associated with cancer and thus diagnose a cancer. In addition, if the patient is believed to have a tumor, then identification of the Ras mutation, as compared to the identification of a different mutation or at least the non-identification of a Ras mutation, may indicate to the clinician how aggressive the patient tumor is likely to be, thus allowing for a more specific prognosis of the cancer. As discussed above, without being bound by theory, the present inventors believe that detection of the combination of a Ras E76 mutation in combination with a G12 mutation is predictive of a more aggressive tumor, and accordingly, the prognosis for the patient may be poorer than for a patient without such combination, and/or a patient with such combination may be treated more aggressively than a patient without such combination of mutations. Finally, identification of a Ras mutation or combination of mutations in the patient tumor can be used to develop a specific cancer therapy protocol based on the knowledge of how this particular mutation effects cellular activity, and can also be used to predict the response or susceptibility of the patient to a particular type of therapy.

The present invention also includes a kit that utilizes the diagnostic methods of the present invention. The kit preferably contains any reagent useful for detecting the presence or absence of the Ras (protein) or ras (nucleic acid) mutation according to the present invention in a test sample, and preferably includes an oligonucleotide probe, PCR primers, or an antibody, antigen binding peptide, or aptamer, that binds to the biomarker (i.e., the mutated ras gene, RNA, cDNA, or protein encoded thereby). The kit can include any reagent needed to perform a diagnostic method envisioned herein. The kit can also include reagents for the detection of other cancer biomarkers, such as the previously described Ras mutations, or any other suitable target for cancer diagnosis, even for cancers having causes or contributions unrelated to the Ras mutation described herein. The reagents (e.g., probe, antibody, aptamer) can be conjugated to another unit, for example a marker or immobilized to a solid carrier (substrate). In one embodiment, the kit can contain a reagent for detecting a control biomarker characteristic of a cell type in the test sample. The reagent may be present in free form or immobilized to a substrate such as a plastic dish, microarray plate, a test tube, a test rod and so on. The kit can also include suitable reagents for the detection of the reagent and/or for the labeling of positive or negative controls, wash solutions, dilution buffers and the like. The kit can also include a set of written instructions for using the kit and interpreting the results. In one embodiment, the kit is formulated to be a high-throughput assay.

More specifically, according to the present invention, a reagent for detecting biomarker presence, expression or biological activity can be any suitable reagent that can be used in a method for detection of Ras biomarker presence, expression or biological activity as described previously herein. Such reagents include, but are not limited to: a probe that hybridizes under stringent hybridization conditions to a nucleic acid molecule encoding the biomarker or a fragment thereof; primers for amplification of nucleic acids encoding the biomarker or a fragment thereof; an aptamer that specifically binds to a conformationally distinct site on the target molecule (i.e., that can distinguish Ras having an E76 mutation, including a particular E76 mutation, such as E76G, E76K or E76Q, from Ras not having such mutation); and/or an antibody, antigen-binding fragment thereof or other antigen-binding peptide that selectively binds to the biomarker. Antibodies (including, but not limited to, polyclonal and monoclonal antibodies, divalent and monovalent antibodies, bi- or multi-specific antibodies, serum containing such antibodies, antibodies that have been purified to varying degrees, and any functional equivalents of whole antibodies) that selectively bind to a mutated Ras protein in the sample can also be produced using information available in the art (described above).

In one embodiment, a reagent for detecting a control biomarker that is characteristic of the cell type being sampled can generally be any type of reagent that can be used in a method of detecting the presence of a known marker (at the nucleic acid or protein level) in a sample, such as by a method for detecting the presence of a biomarker described previously herein. Specifically, the reagent is characterized in that it identifies a specific marker of the cell type being analyzed that positively identifies the cell type. For example, in a breast tumor assay, it is desirable to screen breast epithelial cells for the level of the biomarker expression and/or biological activity. Therefore, the reagent for detecting a control marker identifies a marker that is characteristic of an epithelial cell and preferably, a breast epithelial cell, so that the cell is distinguished from other cell types, such as a fibroblast. Such a reagent increases the accuracy and specificity of the assay of the present invention. Such a reagent for detecting a control marker include, but is not limited to: a probe that hybridizes under stringent hybridization conditions to a nucleic acid molecule encoding a protein marker; PCR primers which amplify such a nucleic acid molecule; an aptamer that specifically binds to a conformationally distinct site on the target molecule; and/or an antibody, antigen binding fragment thereof, or antigen binding peptide that selectively binds to the control marker in the sample. Nucleic acid and amino acid sequences for many cell markers are known in the art and can be used to produce such reagents for detection.

The reagent for detecting a Ras biomarker and/or a control marker of the assay kit of the present invention can be conjugated to a detectable tag or detectable label. Such a tag can be any suitable tag which allows for detection of the reagents used to detect the biomarker or control marker and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™) fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the reagent for detecting of the assay kit of the present invention can be immobilized on a substrate. Such a substrate can include any suitable substrate for immobilization of a detection reagent such as would be used in any of the previously described methods of detection. Briefly, a substrate suitable for immobilization of a reagent for detecting includes any solid support, such as any solid organic, biopolymer or inorganic support that can form a bond with the reagent for detecting without significantly effecting the activity and/or ability of the detection reagent to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand.

Screening Methods of the Invention

One embodiment of the present invention relates to methods for identifying compounds that are useful for protecting a patient from cancer that carries a mutant Ras gene or expresses a Ras protein having the E76 mutation described herein, or a combination of the E76 mutation with another Ras mutation, such as G12. The method includes using the Ras E76 protein or peptide, or a nucleic acid molecule encoding such protein or peptide, as a target in an assay for screening and selecting a chemical compound and/or a biological compound having activity as an anti-tumor therapeutic, based on the ability of the compound to down-regulate expression of the mutated ras gene, to inhibit activity of its gene product, or to reverse or compensate for a biological activity of the mutated Ras protein, such as a compound that triggers GTP hydrolysis of Ras despite the presence of the mutation identified herein. In one embodiment, the method includes using as a target a Ras protein or peptide, or a nucleic acid molecule encoding such protein or peptide, wherein the Ras protein or peptide has a mutation at any one or more of positions 73, 74, 75, 77 or 78, or any of the combinations of Ras mutations described above and particularly, any combination of a mutation at position 12 and/or 13 with a mutation at position 59, 61, 73, 74, 75, 76, 77, and/or 78.

For example, a candidate compound for identification includes a compound that triggers GTPase activity, so that the bound GTP in the mutant Ras is hydrolyzed to GDP despite the presence of the mutation, whereby 'constitutive' Ras activity is turned off, thus quenching the unregulated signals for cell proliferation. Reference herein to inhibiting a target can refer to one or both of inhibiting expression of a target gene and inhibiting the translation and/or activity of its corresponding expression product (protein). Compounds that modify the biological activity of a target, such as the above-mentioned compounds that trigger or initiate hydrolysis of GTP of mutated Ras of the invention are also encompassed by the method of identification. Such compounds can be referred to herein as therapeutic compounds.

In one embodiment, compounds to be identified include compounds that regulate, adapt or mimic Ras-GAP, wherein the regulated, adapted, or mimicked Ras-GAP has the ability to enable the hydrolysis of GTP associated with any of the mutant Ras proteins described herein (e.g., a Ras E76 mutant, any Ras 73-78 mutant, or any of the combination mutants described herein), but does not enable the hydrolysis of GTP associated with wild-type Ras. In this aspect, the novel mutations described herein are used to identify compounds that can restore the function of the Ras GTP hydrolysis pathway in cells (e.g., tumor cells) that harbor one or more Ras mutation described herein, thereby arresting uncontrolled proliferation and metastases of such cells, while leaving "normal" cells (non-cancerous cells) alone. Such a strategy allows for the identification of compounds that target tumor cells but do not cause problems by interrupting the normal, cellular functions of Ras in non-tumor cells. In this embodiment, compounds are identified by selecting compounds that restore GTP hydrolysis to cells expressing (naturally or by recombinant methods) a mutated Ras target, but do not cause GTP hydrolysis in cells that express non-mutated (wild-type) Ras.

In one aspect of this embodiment, therapeutic compounds are identified by exposing a target protein (e.g., E76G Ras) of the present invention (or a cell expressing the protein naturally or recombinantly) to a candidate compound and measuring the ability of the compound to inhibit (reduce, decrease, block) a biological activity of the protein or more particularly, the ability of the protein to contribute to unrestrained cellular growth or proliferation of a cell. In one embodiment, a candidate compound is identified by its ability to initiate or trigger GTP hydrolysis and effectively override or compensate for the presence of the mutant Ras of the present invention. Methods for measuring GTP hydrolysis and GTPase activity are well known in the art.

In another aspect of this embodiment, a cell line that naturally expresses the mutant ras gene or has been transfected with the gene or other recombinant nucleic acid molecule encoding mutated Ras protein is incubated with various compounds, also referred to as candidate compounds, test compounds, or putative regulatory compounds. A reduction of the expression of mutated ras gene or a modification of the activities of its encoded product may be used to identify a therapeutic compound. For example, one can contact the cell expressing mutant Ras with the candidate compound and identify compounds that trigger the GTPase activity as discussed above. Such compounds may be identified by their ability to bind to Ras and activate GTPase under conditions where endogenous Ras-GAP are blocked from binding to Ras by the Ras mutations, and/or may allow release of the γ-phosphate from Ras GTP when hydrolysis is initiated. In other words, the assay attempts to detect compounds that overcome the effects of the Ras mutation or combination of mutations. Alternatively, a variety of similar cell-free assays can be used to identify such therapeutic compounds. Therapeutic compounds identified in this manner can then be re-tested, if desired, in other assays to confirm their activities. Preferably, a compound is selected that does not also trigger GTP hydrolysis in cells that express wild-type Ras (that do not express a mutated Ras).

In one embodiment of the invention, inhibitors of uncontrolled cell growth are identified by exposing a target gene or portion thereof (i.e., a mutated E76G ras gene) to a test compound; measuring the expression of a target (E76G Ras); and selecting a compound that down-regulates (reduces, decreases, inhibits, blocks) the expression or modifies the activity of the target. For example, the putative inhibitor can be exposed to a cell that expresses the target gene (endogenously or recombinantly). A preferred cell to use in an assay includes a mammalian cell that either naturally expresses the target gene or has been transformed with a recombinant form of the target gene, such as a recombinant nucleic acid molecule comprising a nucleic acid sequence encoding the target protein or a useful fragment thereof. Methods to determine expression levels of a gene are well known in the art. Methods for the design and identification of nucleic acid molecules that inhibit the expression of genes or the biological activities of the proteins encoded thereby are well known in the art.

In one embodiment of the invention, therapeutic compounds are identified by exposing a target (e.g., E76G Ras-GTP) to a candidate compound; measuring the binding of the candidate compound to the target; and selecting a compound that binds to the target at a desired concentration, affinity, or avidity. In a preferred embodiment, the assay is performed under conditions conducive to promoting the interaction or binding of the compound to the target. One of skill in the art can determine such conditions based on the target and the compound being used in the assay. In one embodiment, a BIAcore machine can be used to determine the binding constant of a complex between the target protein (a protein encoded by the target gene) and a natural ligand in the presence and absence of the candidate compound. For example, the target protein or a ligand binding fragment thereof can be immobilized on a substrate. A natural or synthetic ligand is contacted with the substrate to form a complex. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Contacting a candidate compound at various concentrations with the complex and monitoring the response function (e.g., the change in the refractive index with respect to time) allows the complex dissociation constant to be determined in the presence of the test compound and indicates whether the candidate compound is either an inhibitor or an agonist of the complex. Alternatively, the candidate compound can be contacted with the immobilized target protein at the same time as the ligand to see if the candidate compound inhibits or stabilizes the binding of the ligand to the target protein.

Compounds to be screened in the methods of the invention include known organic compounds such as products of peptide libraries, nucleic acid molecules (e.g., RNAi, ribozymes, aptamers, anti-sense), antibodies, and products of chemical combinatorial libraries. Compounds may also be identified using rational drug design relying on the structure of the product of a gene, alone or in complex with another component (e.g., mutant Ras complexed with GTP). Such methods are known to those of skill in the art and involve the use of three-dimensional imaging software programs. FIG. 4 illustrates the three-dimensional conformational changes that occur in Ras as a result of two known Ras mutations, for example. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

As used herein, the term "test compound", "putative inhibitory compound" or "putative regulatory compound" refers to compounds having an unknown or previously unappreciated regulatory activity in a particular process. As such, the term "identify" with regard to methods to identify compounds is intended to include all compounds, the usefulness of which as a regulatory compound for the purposes of inhibiting cell growth is determined by a method of the present invention.

The conditions under which a cell, cell lysate, nucleic acid molecule or protein of the present invention is exposed to or contacted with a putative regulatory compound, such as by mixing, are any suitable culture or assay conditions. In the case of a cell-based assay, the conditions include an effective medium in which the cell can be cultured or in which the cell lysate can be evaluated in the presence and absence of a putative regulatory compound. Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Cells are contacted with a putative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of the particular cell type used in the assay, and the chemical composition of the putative regulatory compound (i.e., size, charge etc.) being tested. A preferred amount of putative regulatory compound(s) can comprise between about 1 nM to about 10 mM of putative regulatory compound(s) per well of a 96-well plate.

As used herein, the term "expression", when used in connection with detecting the expression of a target of the present invention, can refer to detecting transcription of the target gene and/or to detecting translation of the target protein encoded by the target gene. To detect expression of a target refers to the act of actively determining whether a target is expressed or not. This can include determining whether the target expression is upregulated as compared to a control, downregulated as compared to a control, or unchanged as compared to a control. Therefore, the step of detecting expression does not require that expression of the target actually is upregulated or downregulated, but rather, can also include detecting that the expression of the target has not changed (i.e., detecting no expression of the target or no change in expression of the target). Expression of transcripts and/or proteins is measured by any of a variety of known methods in the art. For RNA expression, methods include but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

In a preferred embodiment, the expression of the target gene is measured by the polymerase chain reaction. In another embodiment, the expression of the target gene is measured using polyacrylamide gel analysis, chromatography or spectroscopy.

In another preferred embodiment, the expression of the target gene is measured by measuring the production of the encoded protein (measuring translation of the protein). Measurement of translation of a protein includes any suitable method for detecting and/or measuring proteins from a cell or cell extract. Such methods include, but are not limited to, immunoblot (e.g., Western blot), enzyme-linked immunosorbant assay (ELISA), radioimmunoassay (RIA), immunoprecipitation, immunohistochemistry, immunofluorescence, fluorescence activated cell sorting (FACS) and immunofluorescence microscopy. Particularly preferred methods for detection of proteins include any single-cell assay, including immunohistochemistry and immunofluorescence assays. For example, one can use a detection agent, such as an antibody that specifically recognizes (selectively binds to) the protein encoded by the gene. Such methods are well known in the art.

Candidate compounds identified or designed by the above-described methods can be synthesized using techniques known in the art, and depending on the type of compound. Synthesis techniques for the production of non-protein compounds, including organic and inorganic compounds are well known in the art. For example, for smaller peptides, chemical synthesis methods are preferred. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol*. 289:3-13; Wade et al., 1993, *Australas Biotechnol*. 3(6):332-336; Wong et al., 1991, *Experientia* 47(11-12):1123-1129; Carey et al., 1991, *Ciba Found Symp*. 158:187-203; Plaue et al., 1990, *Biologicals* 18(3):147-157; Bodanszky, 1985, *Int. J. Pept. Protein Res*. 25(5):449-474; or H. Dugas a C. Penney, BIOORGANIC CHEMISTRY, (1981) at pages 54-92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture. A compound that is a protein or peptide can also be produced using recombinant DNA technology and methods standard in the art, particularly if larger quantities of a protein are desired.

Any compound identified by these methods can be used in the preparation of a medicament for the treatment or prevention of cancer, or in other methods or uses described herein.

The following experimental results are provided for purposes of illustration and are not intended to limit the scope of the invention.

EXAMPLES

Example 1

The following example describes the identification of a new Ras mutation in tumors evaluated during a Phase 1 immunotherapy trial of whole, heat-killed yeast expressing mutated Ras proteins (Tarmogens).

Materials and Methods

Used in Examples 1 and 2

Patients. 149 patients with pancreatic cancer, colorectal cancer or non-small-cell lung cancer were enrolled in a phase I trial (GlobeImmune, Inc.) of targeted molecular immunotherapy with whole, heat-killed yeast expressing mutated Ras proteins (Tarmogens). Biopsy samples of patient tumors were genotyped for ras mutations to identify subjects with product-related mutations to be enrolled in the immunotherapy trial.

Tissue samples and genomic DNA isolation. Tumor sample of each patient was received as either paraffin embedded block or slides mounted with sections cut from paraffin block. Tumor cells were isolated by LCM (laser capture microscopy) or microscopic scalpel scraping from stained (HistoGene Staining Solution, Arcturus, Calif.) 6-8 µm thick sections, then genomic DNA from these isolated tumor cells was extracted by SDS-proteinase K treatment and RNase A digestion, followed by isopropanol precipitation.

PCR and ras sequencing. Nested PCR was performed for exons 2 and 3 of K-, N-, and H-ras genes using platinum Taq DNA polymerase high fidelity kit (Invitrogen, CA). The 25 µL of external PCR reaction mixture includes 100 ng template DNA, 1× PCR buffer, 50-100 pmol MgSO4, 5 nmol of dNTPs, 10 pmol of each external primer and 2.5 units of high fidelity Taq DNA polymerase. Thermal cycling was initiated with denaturation at 94° C. for 5 min followed by 35 three-step cycles at 94° C. for 30 s, 55° C. for 30 s and 68° C. for 50 s, and followed by a final incubation for 10 min at 68° C. The internal PCR reactions were performed in a total of 50 µL mixtures with 1 µL of the external PCR products as template and 20 pmol of each internal primer. The following primers were used:

K-ras exon 2 external forward primer:

```
5'-AGGTGAGTTTGTATTAAAAG-3';    (SEQ ID NO: 16)
```

K-ras exon 2 external reverse primer:

```
5'-TCATGAAAATGGTCAGAG-3';    (SEQ ID NO: 17)
```

K-ras exon 2 internal forward primer:

```
                                   (SEQ ID NO: 18)
5'-TAATACGACTCACTATAGGGTGTGTGACATGTTCTAAT-3';
```

K-ras exon 2 internal reverse primer

```
                                   (SEQ ID NO: 19)
5'-ATTTAGGTGACACTATAGAAGAATGGTCCTGCACCAGTAA-3';
```

K-ras exon 3 external forward primer:

```
5'-TGAGTTGTATATAACACC-3';    (SEQ ID NO: 20)
```

K-ras exon 3 external reverse primer:

```
5'-GGCATTAGCAAAGACTCA-3';    (SEQ ID NO: 21)
```

K-ras exon 3 internal forward primer:

```
                                   (SEQ ID NO: 22)
5'-TAATACGACTCACTATAGGG TGCACTGTAATAATCCAG-3';
```

K-ras exon 3 internal reverse primer:

```
                                   (SEQ ID NO: 23)
5'-ATTTAGGTGACACTATAGAA ATTACTCCTTAATGTCAGC-3';
```

N-ras exon 2 external forward primer:

```
5'- ATGGAAGGTCACACTAGGG-3';    (SEQ ID NO: 24)
```

N-ras exon 2 external reverse primer:

```
5'- AAGATGATCCGACAAGTG-3';    (SEQ ID NO: 25)
```

N-ras exon 2 internal forward primer:

```
                                   (SEQ ID NO: 26)
5'-TAATACGACTCACTATAGGGAGTACTGTAGATGTGGCTCG-3';
```

N-ras exon 2 internal reverse primer:

```
                                   (SEQ ID NO: 27)
5'- ATTTAGGTGACACTATAGAAGAGACAGGATCAGGTCAGCG-3';
```

N-ras exon 3 external forward primer:

```
5'- TGGCAATAGCATTGCATTC-3';    (SEQ ID NO: 28)
```

N-ras exon 3 external reverse primer:

```
5'- GGTAACCTCATTTCCCCA-3';    (SEQ ID NO: 29)
```

N-ras exon 3 internal forward primer:

```
                                   (SEQ ID NO: 30)
5'- TAATACGACTCACTATAGGGTTGAACTTCCCTCCCTCCCTG-3';
```

N-ras exon 3 internal reverse primer:

```
                                   (SEQ ID NO: 31)
5'- ATTTAGGTGACACTATAGAATTCAGAACACAAAGATCA-3';
```

H-ras exon 2 external forward primer:

```
5'- TTGGCAGGTGGGGCAGGAGA-3',    (SEQ ID NO: 32)
```

H-ras exon 2 external reverse primer:

```
5'-CCTATCCTGGCTGTGTCC-3',    (SEQ ID NO: 33)
```

H-ras exon 2 internal forward primer:

```
                                   (SEQ ID NO: 34)
5'- TAATACGACTCACTATAGGGAGGAGACCCTGTAGGAG-3',
```

H-ras exon 2 internal reverse primer:

(SEQ ID NO: 35)
5'- ATTTAGGTGACACTATAGAACTCGCCCGCAGCAGCTGC-3',

H-ras exon 3 external forward primer:

5'-ACCAGGGAGAGGCTGGC-3', (SEQ ID NO: 36)

H-ras exon 3 external reverse primer:

5'-CTCCCGGGCCAGCCTCAC-3', (SEQ ID NO: 37)

H-ras exon 3 internal forward primer:

(SEQ ID NO: 38)
5'TAATACGACTCACTATAGGGTGAACTCCCCCCACGGAAGG-3', and

H-ras exon 3 internal reverse primer (SEQ ID NO: 39)
5'-ATTTAGGTGACACTATAGAAGTTCACCTGTACTGGTGGA-3'.

All the forward internal primers were supplemented with T7 primer sequence at the 5' end, and all the reverse internal primers were supplemented with SP6 primer sequence at the 5' end. Internal PCR products were purified with QIA quick gel extraction kit (Qiagen, CA) after eletrophoresis through 1.5% agrose. The purified DNA was sent to CU Cancer Center DNA Sequencing & Analysis Core for two strand sequencing using T7 and SP6 primers.

Construction of mouse K-ras gene expression vectors. Total RNA was isolated from E9 mouse lung epithelial cell line using Trizol reagent from Invitrogen (Invitrogen, CA). cDNA of mouse K-ras gene was reverse transcribed from 2.5 μg of total RNA using m-kras reverse primer:

5'-GCTCGGCTGCGGCCGCTCACTACAT-AACTGTACACCTTGTCCT-3' (SEQ ID NO:40) and SuperScript™ III Reverse Transcriptase kit (Invitrogen, CA) according to the manufacturer's instructions. One-tenth of the reacted aliquots was subsequently amplified by PCR with m-kras forward primer:

5'-GGAATTCACCATGGGCACTGAG-TATAAACTTGTGGTG-3' (SEQ ID NO:41) and m-kras reverse primer which are designed to cover the entire coding region of mouse K-ras cDNA. Thermal cycling was initiated with incubation for 5 min at 94° C. followed by 35 three-step cycles at 94° C. for 25 s, 55° C. for 25 s, and 68° C. for 30 s. PCR product was cloned to pGEM-T Vector (Promega, Wis.) according to the manufacturer's instruction. This mouse k-ras gene contains Q61R mutation, then wild type mouse k-ras and mouse k-ras containing G12V, E76G, E76K and G12VE76G mutations were made by site-directed mutagenesis and cloned into mammalian expression vector pUP at EcoRI and NotI sites. m-kras forward, reverse and the following primers were used:

(SEQ ID NO: 42)
rasQ61
5'-TACTCCTCTTGACCTGCTGT-3', (SEQ ID NO: 43)
rasG76
5'-AAGAAAGCCCCCCCCAGTTCTC-3';

(SEQ ID NO: 44)
rasV12
5'ACGGAATTCACCATGACTGAGTATAAACTTGTGGTGGTTGGAGCTGTTGGCGTAG-3', (SEQ ID NO: 45)
rasK76
5'-AAGAAAGCCCTTCCCAGTTCTC-3'.

Cell culture and transfection. BALB3T3 cells were cultured in DMEM containing 10% new born calf serum, 50 U/ml penicillin, and 50 μg/ml streptomycin. The WT, G12V, E76G, E76K, and G12V+E76G k-ras expression plasmids were transfected into BALB3T3 cells using Effectene Transfection Reagent kit (Qiagen, CA). Transfected cells were selected with G418 and purified by selecting clones from culture plate (wild type) or from soft agar (G12V, E76G, E76K, G12V+E76G). The expression of the transfected wild-type K-ras (WT) or mutated K-ras genes was confirmed by RT-PCR and immunoblot of Ras protein. Total RNA was isolated from each transfected cell clone using Trizol reagent and cDNA of ras gene was reverse amplified using SuperScript™ III Reverse Transcriptase kit (Invitrogen, CA) and m-kras reverse primer, then the exogenous ras gene was amplified by PCR using m-kras reverse primer and forward primer in pUP vector promoter 5'-TTGGGTCGCGGTTCT-TGT-3' (SEQ ID NO:46). Total protein was extracted using RIPA lysis buffer (Upstate, N.Y.) from each transfected cell clone, and proteins were resolved on 12% SDS-PAGE gels (Invitrogen, CA) followed by transferring to nitrocellulose membrane and blotted with anti-Ras antibody (Oncogene, Mass.) and anti-GAPDH antibody (Abcam, Mass.), respectively.

Soft agar assay. $5 \times 10^4$ cells were suspended in DMEM containing 0.35% low-melting agarose (SeaPlaque agarose, Cambres BioScience Rockland Inc, me) and 10% new born calf serum (NBCS) overlaid onto a bottom 0.5% low-melting agarose layer containing 10% NBCS. Following 2-4 weeks growth, the colonies were observed or selected into liquid DMEM medium containing 10% NBCS.

Tumorigenicity assay. Each transfectant clone was grown, harvested, and suspended in PBS.

$5 \times 10^6$ cells were injected subcutaneously into 4-6-week-old Balb/c nude mice. Injected cells were monitored twice a week over a period of 30 days, tumors were measured and tumor volume was calculated as $3.142 \times (length) \times (width)^2 / 6$.

Results

In this study, K-, N- and H-ras DNA sequences were characterized for the presence of tumor-associated mutations by nested PCR amplification and direct sequencing from tumors of 149 subjects with pancreas (68% harboring mutations), colorectal (40% with mutations) or NSCLC (9% with mutations) cancers in a phase 1 immunotherapy trial of whole, heat-killed yeast expressing mutated Ras proteins (Tarmogens). A new ras mutation at codon 76 was detected in 24 subjects from all 3 cancer types, with 22 being E76G, while 1 tumor each harbored E76K or E76Q mutations. Double combinations of E76 plus mutations at codons 12 or 13 were identified in 8 tumors. See Tables 1 and 2 and FIG. 1.

TABLE 1

Summary of Mutations at Codon 76

| | Colorectal (85) | | | Lung (33) | | | Pancreas (31) | | | Total |
|---|---|---|---|---|---|---|---|---|---|---|
| | K-ras | N-ras | H-ras | K-ras | N-ras | H-ras | K-ras | N-ras | H-ras | (149) |
| E76G | 2* | | 3* | 3 | | 1 | 2 | | | |
| Possible E76G# | 5 | | 1 | | | 1 | 4 | | 1 | |
| E76K | | 1 | | | | | | | | |
| E76Q | 1 | | | | | | | | | |
| Total | 8* | 1 | 4* | 3 | 0 | 2 | 6 | 0 | 1 | 24 |

*One sample has E76G in both K and H-ras;
weaker signal for E76 mutation detected, likely due to low abundance of tumor cells in biopsy sample.

TABLE 2

Summary of hot spot ras mutations (codons 12, 13 and 61)

| | | | Mutations | | | | | | | | | | | | | |
|---|---|---|---|---|---|---|---|---|---|---|---|---|---|---|---|---|
| Cancer type | # samples screened per cancer | # subjects with ras mutations (% per cancer) | Codon 12 | | | | | | | Codon13 | | Codon 61 | | | | |
| | | | Total | G12V | G12C | G12D | G12R | G12S | G12A | Total | G13D | Total | Q61R | Q61L | Q61H | Q61P |
| Colorectal | 85 | 34 (40%) | 29 (85.3%) | 10 | 4 | 10 | 0 | 3 | 2 | 3 | 3 | 2 | 0 | 1 | 1 | 0 |
| Lung | 33 | 3 (9.1%) | 2 (66.7%) | 0 | 2 | 0 | 0 | 0 | 0 | 0 | 0 | 1 | 0 | 0 | 0 | 1 |
| Pancreas | 31 | 21 (67.7%) | 19 (95%) | 6 | 0 | 10 | 3 | 0 | 0 | 0 | 0 | 2 | 1 | 0 | 1 | 0 |
| Total | 149 | 58 (38.9%) | 50 (86.2%) | 17 | 6 | 20 | 3 | 3 | 2 | 3 | 3 | 5 | 1 | 1 | 2 | 1 |

Example 2

The following Example demonstrates that Ras E76 mutations are transforming, and further, that Ras E76 mutations synergize with Ras G12 mutations to increase the oncogenicity of a tumor.

Figure 2A:
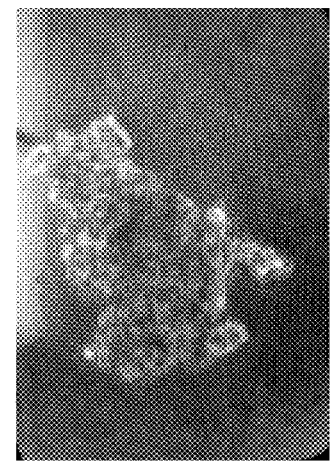
FIGS. 2A and 2B are digital images of a soft agar assay of cell growth showing exemplary negative (FIG. 2A, untransfected BALB/3T3 mouse cells) and positive (FIG. 2B, G12V+E76G Ras-transfected BALB/3T3 mouse cell clone) colony formation in soft agar. Cancer ("transformed") epithelial cells are capable of growing in soft agar, whereas untransformed cells do not grow in soft agar.
Figure 2B:
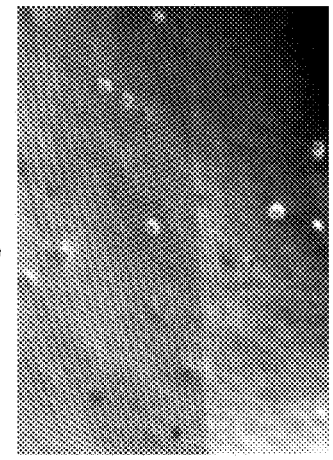

Ras E76G and E76K mutations were confirmed as transforming in non-clinical studies. Of particular interest, coupling codon 76 and 12 mutations resulted in tumor growth synergy. G12V, E76G and E76K single mutations or double G12V-E76G mutations were introduced into the mouse K-ras gene and then transfected into BALB/3T3 fibroblasts. Cells transfected with ras harboring G12V or E76K alone, or the G12V-E76G double mutation formed colonies in soft agar (see FIGS. 2A and 2B and Table 3).

TABLE 3

E76 as a Transforming Mutation

| Clone (K-ras genotype transfected BALB/3T3 cells) | mRNA transcript of transfected ras gene (by RT-PCR) | Exogenous Ras protein expression (western blot) | Colony formation in soft agar |
|---|---|---|---|
| wild-type (WT) | + | + | − |
| G12V | + | + | ++++ |
| G12V + E76G | + | + | +++++ |
| E76G | + | + | − |
| E76K | + | + | ++ |

TABLE 3-continued

E76 as a Transforming Mutation

| Clone (K-ras genotype transfected BALB/3T3 cells) | mRNA transcript of transfected ras gene (by RT-PCR) | Exogenous Ras protein expression (western blot) | Colony formation in soft agar |
|---|---|---|---|
| pUP (empty vector) | − | − | − |
| Balb3T3 (untransfected) | − | − | − |

Figure 3A:
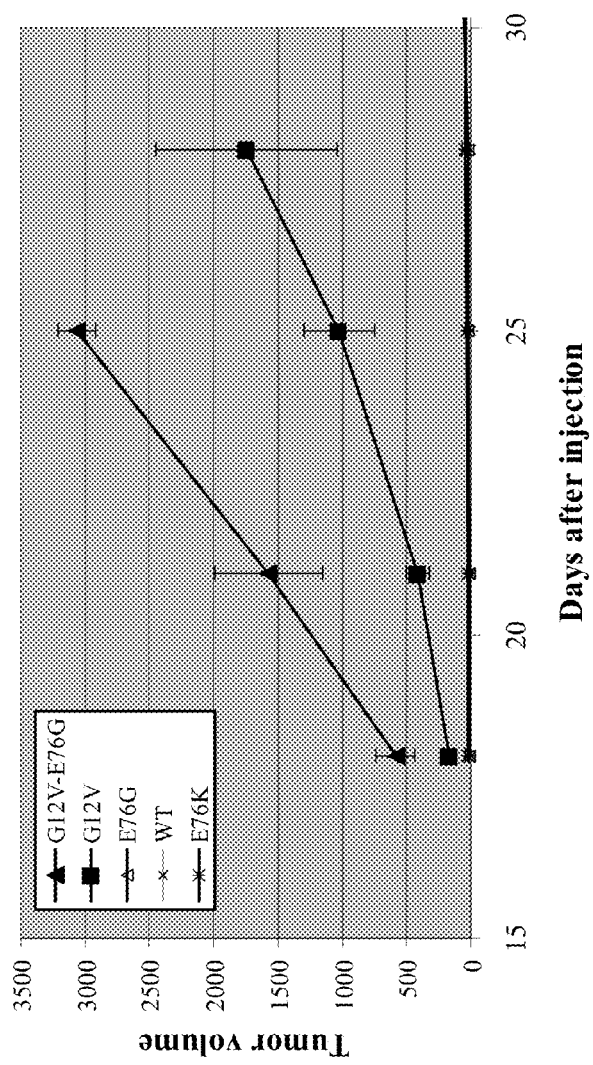
FIGS. 3A and 3B are graphs showing two separate experiments demonstrating oncogenic synergy in the growth of tumors carrying Ras mutations at both codon 12 and codon 76 in Balb/c nude mice.
Figure 3B:
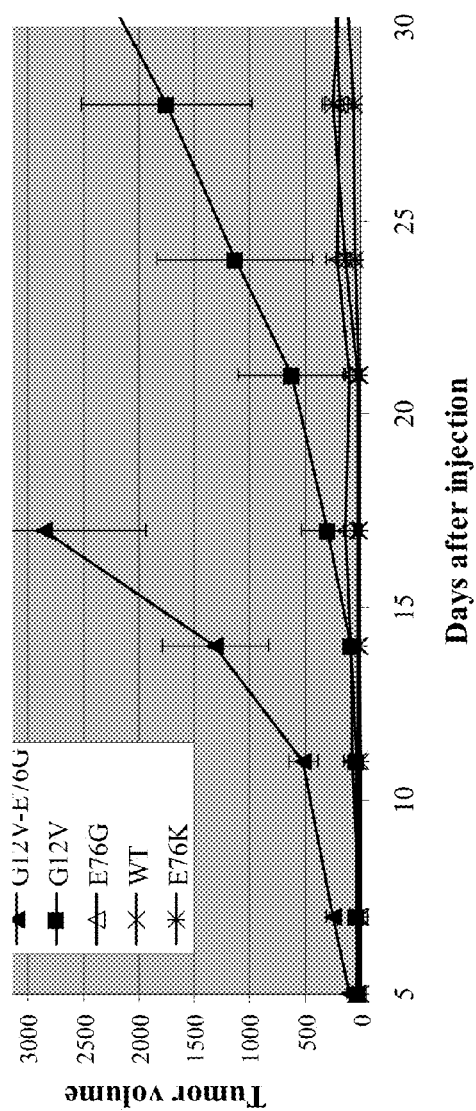
Figure 3C:
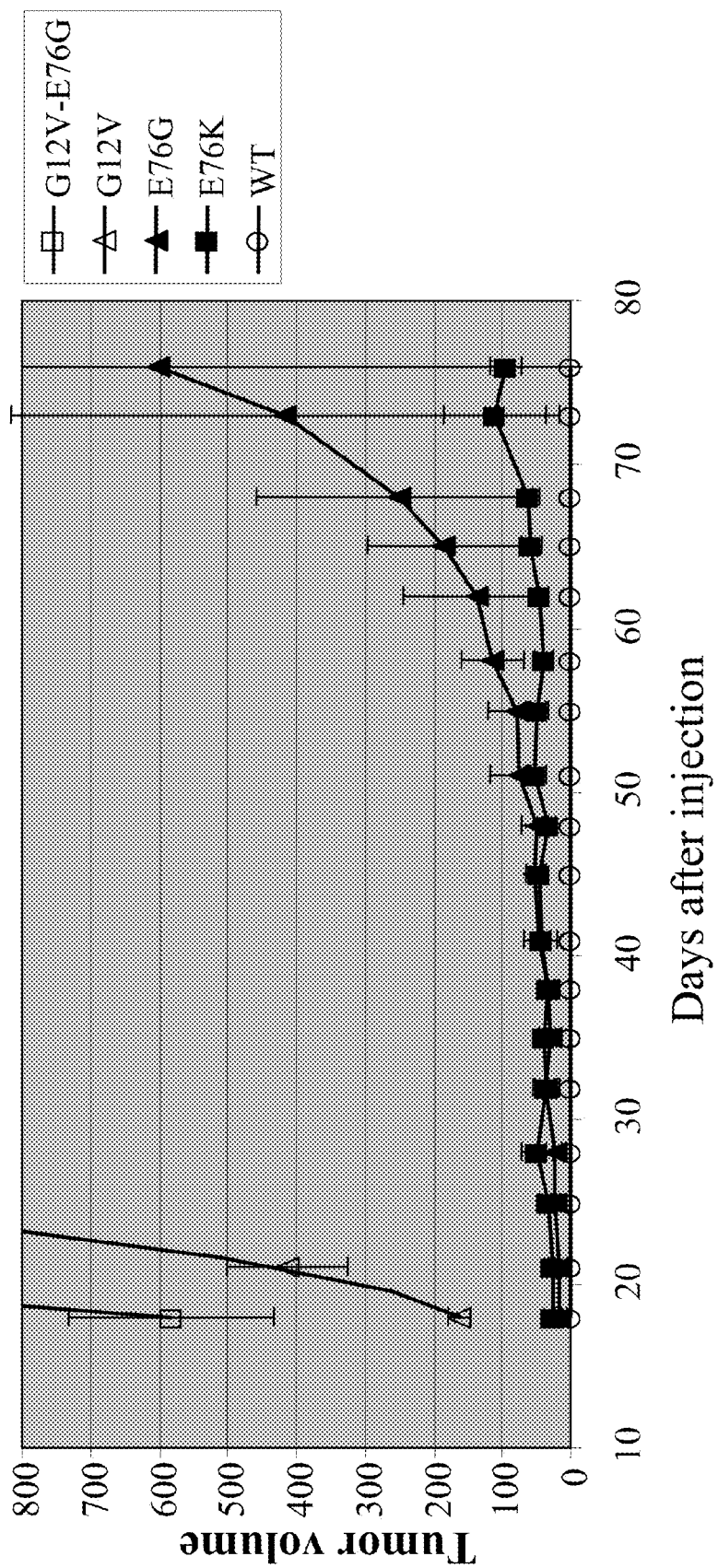
FIG. 3C is an expanded detail of the study in FIG. 3A to show the growth of individual E76 mutant-transfected cells relative to untransfected (wild-type) BALB/3T3 cells.

The BALB/3T3 cells transfected with wild-type or mutant K-ras genes were injected subcutaneously (s.c.) into BALB/c nude mice. FIGS. 3A and 3B are repeats of the assay. Bars indicate standard deviations of 3 mice per group. FIG. 3C is an expanded detail of the study shown in FIG. 3A to show the growth of individual E76 mutant-transfected cells relative to untransfected (wild-type) BALB/3T3 cells.

The cells bearing single E76G or E76K mutations in K-Ras resulted in detectable growth in the nude mice by comparison to the cells transfected with wild-type K-Ras, although tumor growth with single E76 mutations was significantly lower than cells transfected to express G12V mutated K-Ras (see FIG. 3C). Cells transfected with Ras harboring the double G12V+E76G Ras mutation led to accelerated tumor growth compared to cells bearing any single mutation (see FIGS. 3A-3C).

Example 3

The following experiment describes a yeast-based vaccine comprising a yeast vehicle and fusion protein comprising a Ras E76 mutation.

*Saccharomyces cerevisiae* was engineered to express a multi-domain mutant Ras fusion protein under the control of the copper-inducible promoter, CUP1. The fusion protein is a single polypeptide with the following sequence elements fused in frame from N- to C-terminus (the amino acid sequence of the fusion protein being represented herein by SEQ ID NO:14): 1) the sequence MADEAP (SEQ ID NO:1) to confer stability of the nascent yeast-expressed heterologous protein during cell culturing (positions 1 to 6 of SEQ ID NO:14); 2) a fragment of Ras containing the amino acid position 12 with respect to a wild-type Ras protein, wherein the glycine at position 12 is substituted with a cysteine (positions 7-52 of SEQ ID NO:14; with the position 12 mutation being at position 17 of SEQ ID NO:14); 3) a fragment of Ras containing the amino acid position 61 with respect to a wild-type Ras protein, wherein the glycine at position 61 is substituted with an arginine (positions 53-91 of SEQ ID NO:14; with the position 61 mutation being at position 66 of SEQ ID NO:14); 4) a fragment of Ras containing the amino acid position 12 with respect to a wild-type Ras protein, wherein the glycine at position 12 is substituted with an aspartate (positions 92-137 of SEQ ID NO:14; with the position 12 mutation being at position 102 of SEQ ID NO:14); 5) a fragment of Ras containing the amino acid position 12 with respect to a wild-type Ras protein, wherein the glycine at position 12 is substituted with a valine (positions 138-183 of SEQ ID NO:14; with the position 12 mutation being at position 148 of SEQ ID NO:14); 6) a fragment of Ras containing the amino acid position 12 with respect to a wild-type Ras protein, wherein the glycine at position 12 is substituted with an arginine (positions 184-229 of SEQ ID NO:14; with the position 12 mutation being at position 194 of SEQ ID NO:14); and 7) a fragment of Ras containing the amino acid position 76 with respect to a wild-type Ras protein, wherein the glutamate at position 76 is substituted with a glycine (positions 230-275 of SEQ ID NO:14; with the position 76 mutation being at position 258 of SEQ ID NO:14).

Growth and induction of the yeast expressing the Ras fusion protein was performed, and the expression of the protein was detected.

These yeast were administered to A/J mice in which 25-50 lung tumors were spontaneously induced by urethane exposure, which triggers mutations in Ras at codon 61 (80-90% of tumors) and codon 12 (~10% of tumors), or tumors that emerge independent of Ras mutations (<10% tumors). Administration of the vaccines was performed by subcutaneous administration at 2 or 5 weeks after urethane induction. The vaccine reduced tumor burden in the mice in a statistically significant manner, as compared to mice receiving no vaccine, indicating that the yeast vaccine is capable of eliciting an anti-tumor immune response that targets tumors harboring at least one of the mutations encoded by the fusion protein construct.

In a further experiment to test for the induction of an immune response to Ras harboring a mutation at position 76, these yeast are administered to mice in which tumors have been initiated or are to be initiated, wherein the tumor cells have been engineered to express Ras comprising an E76G mutation or naturally express Ras comprising an E76G mutation. The effect of the vaccine on reduction of tumor burden is evaluated. In addition, T cells from the mice are isolated and tested for their ability to kill target cells expressing a Ras comprising the E76G mutation (in a CTL assay), and/or to proliferate in response to Ras comprising the E76G mutation presented by an antigen presenting cell. It is expected that tumor burden is reduced in the mice as compared to in the absence of administration of the vaccine. Similarly, T cells isolated from these mice are expected to be able to kill targets expressing the mutated Ras protein and/or to proliferate in response to the mutated Ras protein, in an antigen-specific manner.

Example 4

The following experiment describes a yeast-based vaccine comprising a yeast vehicle and fusion protein comprising a Ras E76 mutation.

A *Saccharomyces cerevisiae* was engineered to express a double-domain mutant Ras fusion protein under the control of a promoter. The fusion protein is a single polypeptide with the following sequence elements fused in frame from N- to C-terminus (the amino acid sequence of the fusion protein being represented herein by SEQ ID NO:15): 1) the sequence MADEAP (SEQ ID NO:1) to confer stability of the nascent yeast-expressed heterologous protein during cell culturing (positions 1 to 6 of SEQ ID NO:15); 2) a fragment of Ras containing the amino acid position 12 with respect to a wild-type Ras protein, wherein the glycine at position 12 is substituted with an arginine (positions 7-52 of SEQ ID NO:15; with the position 12 mutation being at position 17 of SEQ ID NO:15); and 7) a fragment of Ras containing the amino acid position 76 with respect to a wild-type Ras protein, wherein the glutamate at position 76 is substituted with a glycine (positions 53-98 of SEQ ID NO:15; with the position 76 mutation being at position 81 of SEQ ID NO:15).

Growth and induction of the yeast expressing the Ras fusion protein was performed, and the expression of the protein was detected.

In an experiment to test for the induction of an immune response to Ras harboring a mutation at position 76, these yeast are administered to mice in which tumors have been initiated or are to be initiated, wherein the tumor cells have been engineered to express Ras comprising an E76G mutation or naturally express Ras comprising an E76G mutation. The effect of the vaccine on reduction of tumor burden is evaluated. In addition, T cells from the mice are isolated and tested for their ability to kill target cells expressing a Ras comprising the E76G mutation (in a CTL assay), and/or to proliferate in response to Ras comprising the E76G mutation presented by an antigen presenting cell. It is expected that tumor burden is reduced in the mice as compared to in the absence of administration of the vaccine. Similarly, T cells isolated from these mice are expected to be able to kill targets expressing the mutated Ras protein and/or to proliferate in response to the mutated Ras protein, in an antigen-specific manner.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A composition comprising:
   a) a whole, heat-killed yeast; and
   b) a mutated Ras protein comprising at least 11 contiguous amino acids of a wild-type Ras protein having an amino acid sequence of SEQ ID NO:3, SEQ ID NO:5, SEQ ID NO:7, SEQ ID NO:9, SEQ ID NO:11 or SEQ ID NO:13 that contains amino acid position 76 with respect to the wild-type Ras protein except that the amino acid at position 76 is mutated as compared to the wild-type Ras protein;
   wherein the protein is expressed by the yeast.

2. The composition of claim 1, wherein the amino acid at position 76 is mutated from a glutamate to a non-glutamate amino acid residue selected from the group consisting of: glycine, lysine, and glutamine.

3. A composition comprising:
   a) a yeast vehicle; and
   b) a protein comprising:
      (i) a mutant Ras protein or immunogenic domain thereof, wherein the protein or immunogenic domain thereof contains the amino acid position 76 with respect to a wild-type Ras protein, and wherein the amino acid at position 76 is mutated as compared to the wild-type Ras protein; and
      (ii) at least one additional mutant Ras protein or immunogenic domain thereof, wherein the at least one additional mutant Ras protein or immunogenic domain thereof comprises an amino acid sequence selected from the group consisting of: (a) an amino acid sequence comprising at least from positions 8-16 of a Ras protein, wherein the amino acid residue at position 12 with respect to the wild-type Ras protein is mutated; (b) an amino acid sequence comprising at least from positions 9-17 of a Ras protein, wherein the amino acid residue at position 13 with respect to the wild-type Ras protein is mutated; (c) an amino acid sequence comprising at least from positions 55-63 of a Ras protein, wherein the amino acid residue at position 59 with respect to the wild-type Ras protein is mutated; (d) an amino acid sequence comprising at least from positions 57-65 of a Ras protein, wherein the amino acid residue at position 61 with respect to the wild-type Ras protein is mutated; (e) an amino acid sequence comprising at least from positions 69-77 of a Ras protein, wherein the amino acid residue at position 73 with respect to the wild-type Ras protein is mutated; (f) an amino acid sequence comprising at least from positions 70-78 of a Ras protein, wherein the amino acid residue at position 74 with respect to the wild-type Ras protein is mutated; (g) an amino acid sequence comprising at least from positions 71-79 of a Ras protein, wherein the amino acid residue at position 75 with respect to the wild-type Ras protein is mutated; (h) an amino acid sequence comprising at least from positions 73-81 of a Ras protein, wherein the amino acid residue at position 77 with respect to the wild-type Ras protein is mutated; and (i) an amino acid sequence comprising at least from positions 74-82 of a Ras protein, wherein the amino acid residue at position 78 with respect to the wild-type Ras protein is mutated;
   wherein the protein is expressed by the yeast vehicle.

4. A composition comprising:
   a) a yeast vehicle; and
   b) a protein comprising:
      (i) a mutant Ras protein or immunogenic domain thereof, wherein the protein or immunogenic domain thereof contains the amino acid position 76 with respect to a wild-type Ras protein, and wherein the amino acid at position 76 is mutated as compared to the wild-type Ras protein; and
      (ii) a second mutant Ras protein or immunogenic domain thereof, wherein the second protein or immunogenic domain thereof contains the amino acid position 12 with respect to a wild-type Ras protein, and wherein the amino acid at position 12 is mutated as compared to the wild-type Ras protein;
   wherein the protein is expressed by the yeast vehicle.

5. The composition of claim 4, wherein the amino acid at position 12 is mutated from a glycine to an amino acid selected from the group consisting of valine, cysteine, aspartate, arginine, serine, and alanine.

6. A composition comprising:
   a) a yeast vehicle; and
   b) a protein comprising:
      (i) a mutant Ras protein or immunogenic domain thereof, wherein the protein or immunogenic domain thereof contains the amino acid position 76 with respect to a wild-type Ras protein, and wherein the amino acid at position 76 is mutated as compared to the wild-type Ras protein; and
      (ii) a second mutant Ras protein or immunogenic domain thereof, wherein the second protein or immunogenic domain thereof contains the amino acid position 13 with respect to a wild-type Ras protein, and wherein the amino acid at position 13 is mutated as compared to the wild-type Ras protein;
   wherein the protein is expressed by the yeast vehicle.

7. A composition comprising:
   a) a yeast vehicle; and
   b) a protein comprising the following proteins, fused in frame:
      i) a mutant Ras protein or immunogenic domain thereof, wherein the protein or immunogenic domain contains the amino acid position 12 with respect to a wild-type Ras protein, and wherein the glycine at position 12 is substituted with a cysteine;
      ii) a mutant Ras protein or immunogenic domain thereof, wherein the protein or immunogenic domain contains the amino acid position 61 with respect to a wild-type Ras protein, and wherein the glutamine at position 61 is substituted with an arginine;
      iii) a mutant Ras protein or immunogenic domain thereof, wherein the protein or immunogenic domain contains the amino acid position 12 with respect to a wild-type Ras protein, and wherein the glycine at position 12 is substituted with an aspartate;
      iv) a mutant Ras protein or immunogenic domain thereof, wherein the protein or immunogenic domain contains the amino acid position 12 with respect to a wild-type Ras protein, and wherein the glycine at position 12 is substituted with a valine;
      v) a mutant Ras protein or immunogenic domain thereof, wherein the protein or immunogenic domain contains the amino acid position 12 with respect to a wild-type Ras protein, and wherein the glycine at position 12 is substituted with an arginine; and
      vi) a mutant Ras protein or immunogenic domain thereof, wherein the protein or immunogenic domain contains the amino acid position 76 with respect to a wild-type Ras protein, and wherein the glutamate at position 76 is substituted with a glycine
   wherein the protein is expressed by the yeast vehicle.

8. The composition of claim 4, wherein the protein comprises the following proteins, fused in frame:
  i) a mutant Ras protein or immunogenic domain thereof, wherein the protein or immunogenic domain contains the amino acid position 12 with respect to a wild-type Ras protein, and wherein the glycine at position 12 is substituted with an arginine;
  ii) a mutant Ras protein or immunogenic domain thereof, wherein the protein or immunogenic domain contains the amino acid position 76 with respect to a wild-type Ras protein, and wherein the glutamate at position 76 is substituted with a glycine.

9. The composition of claim 7, wherein the protein comprises the amino acid sequence of SEQ ID NO:14.

10. The composition of claim 8, wherein the protein comprises the amino acid sequence of SEQ ID NO:15.

11. The composition of claim 3, wherein the protein comprises at least one additional cancer antigen or immunogenic domain thereof.

12. The composition of claim 3, wherein the yeast vehicle is a whole yeast.

13. The composition of claim 12, wherein the whole yeast is killed.

14. The composition of claim 12, wherein the whole yeast is heat-killed.

15. The composition of claim 3, wherein the yeast vehicle is from *Saccharomyces*.

16. The composition of claim 3, wherein the yeast vehicle is from *Saccharomyces cerevisiae*.

17. The composition of claim 4, wherein the yeast vehicle is a whole, heat-killed yeast.

18. The composition of claim 4, wherein the yeast vehicle is from *Saccharomyces cerevisiae*.

19. The composition of claim 7, wherein the yeast vehicle is a whole, heat-killed yeast.

20. The composition of claim 7, wherein the yeast vehicle is from *Saccharomyces cerevisiae*.

* * * * *